US005807988A

United States Patent [19]
Kinet et al.

[11] Patent Number: 5,807,988
[45] Date of Patent: Sep. 15, 1998

[54] ISOLATION, CHARACTERIZATION, AND USE OF THE HUMAN AND SUBUNIT OF THE HIGH AFFINITY RECEPTOR FOR IMMUNOGLOBULIN E

[75] Inventors: Jean-Pierre Kinet; Marie-Helene Jouvin, both of Bethesda, Md.

[73] Assignee: The United States of America as represented by the Department of Health and Human Services, Washington, D.C.

[21] Appl. No.: 201,879

[22] Filed: Feb. 24, 1994

Related U.S. Application Data

[63] Continuation-in-part of Ser. No. 869,933, Apr. 16, 1992.
[51] Int. Cl.$^6$ .......................... C07K 14/705; C07K 19/00; C12N 15/62
[52] U.S. Cl. ..................... 530/350; 435/69.1; 435/69.7; 530/324; 530/327; 536/23.4
[58] Field of Search ................................... 435/69.1, 69.7; 530/324–327, 350; 536/23.4

[56] References Cited

FOREIGN PATENT DOCUMENTS

90/04640 5/1990 WIPO .

OTHER PUBLICATIONS

Hutchcroft et al., "FcϵRI–Mediated Tyrosine Phosphorylation And Activation Of The 72–kDa Protein–Tyrosine Kinase, PTK72, In RBL–2H3 Rat Tumor Mast Cells", *Proc. Natl. Acad. Sci. USA*, vol. 89:9107–9111, (1992).

Blank et al., "Complete Structure and Expression in Transfected Cells of High Affinity IgE Receptor", *Nature*, vol. 337:187–189, (1989).

Kinet et al., "A cDNA Presumptively Coding for the α Subunit Of The Receptor With High Affinity For Immunoglobulin E", *Biochemistry*, vol. 26:4605–4610, (1987).

Benhamou et al., "Protein–Tyrosine Kinase p 72$^{syk}$ in High Affinity IgE Receptor Signaling", *The Journal of Biological Chemistry*, vol. 268:23318–23324, (1993).

Benhamou et al., "Tyrosine Phosphorylation Coupled To IgE Receptor–Mediated Signal Transduction And Histamine Release", *Proc. Natl. Acad. Sci. USA*, vol. 87:5327–5330, (1990).

Le Coniat et al., "The Human Genes For the α and γ Subunits of The Mast Cell Receptor for Immunoglobulin E Are Located on Human Chromosome Band 1q23", *Immunogenetics*, vol. 32:183–186, (1990).

Letourneur et al., "Characterization Of the Family of Dimers Associated With Vc Receptors (fcϵRI and FcγRIII)", *The Journal Of Immunology*, vol. 147:2652–2656, (1991).

Letourneur et al., "T–cell And Basophil Activation Through The Cytoplasmic Tail Of T–Cell–Receptor ζFamily Proteins", *Immunology*, vol. 88:8905–8909, (1991).

Li et al., "FcϵRI–Mediated Tyrosine Phosphorylation Of Multiple Proteins, Including Phospholipase Cγ1 And The Receptor $_{2β\gamma}$Complex, In RBL–2H3 Rat Basophilic Leukemia Cells", *Molecular and Cellular Biology*, vol. 12:3176–3182, (1992).

Miller et al., "Cloning and Characterization Of Complementary DNA For Human Tryptase", *J. Clin. Invest.*, vol. 84:118–1195, (1898).

Miller et al., "Expression of High–Affinity Binding of Human Immunoglobulin E By Transfected Cells", *Science*, vol. 244:334–337, (1989).

Paolini et al., "Phosphorylation/Dephosphorylation Of High–Affinity IgE Receptors: A Mechanism For Coupling/ Uncoupling A Large Signaling Complex", *Proc. Natl. Acad. Sci. USA*, vol. 89:10733–10737, (1992).

RA et al., "Complete Structure Of The Mouse Mast Cell Receptor For IgE (FcϵRI) And Surface Expression Of Chimeric Receptors (Rat–Mouse–Human) On Transfected Cells", *The Journal Of Biological Chemistry*, Bol. 264:15323–15327, (1989).

RA et al., "A Macrophage FcγReceptor and The Mast Cell Receptor For IgE Share An Identical Subunit", *Nature*, vol. 341:752–754, (1989).

Samelson et al., "Tyrosine Kinases And Tyroshine–Based Activation Motifs", *The Journal Of Biological Chemistry*, vol. 267:24913–24916, (1992).

Shimizu et al., "Human And Rat Mast Cell High–Affinity Immunoglobulin E Receptors: Characterization of Putative α–Chain Gene Products", *Proc. Natl. Sci. USA*, vol. 85:1907–1911, (1988).

Tepler et al., "The Gene For The Rat Mast Cell High Affinity IgE Receptor α Chain",*J. Biol. Chem.*, vol. 264:5912–5915, (1989).

Varin–Blank et al., "Surface Expression Of Mutated Subunits Of The High Affinity Mast Cell Receptor For IgE", *The Journal Of Biological Chemistry*, vol. 265:15685–15694, (1990).

Weiss, "T Cell Antigen Receptor Signal Transduction: A Tale of Tails and Cytoplasmic Protein–Tyrosine Kinases", *Cell*, vol. 73:209–212, (1993).

(List continued on next page.)

*Primary Examiner*—John Ulm
*Attorney, Agent, or Firm*—Klarquist Sparkman Campbell Leigh & Whinston, LLP

[57] ABSTRACT

The present invention relates to nucleic acid sequences, encoding amino acid sequences of the β, and subunit of the human high affinity receptor for immunoglobulin E, and for amino acid sequences of the subunit. A segment of the amino acid sequence containing an antigen recognition activation motif (ARAM) that exhibits different functions than other ARAMS, including that of the ARAM-γ subunit of FcϵRI. The invention further relates to a method of producing the receptor by expressing cDNA for its a, β, and γ subunits in a host cell simultaneously. Aspects of the invention are methods and compositions to inhibit the function of the human beta subunit, thereby treating or preventing allergic reactions.

6 Claims, 29 Drawing Sheets

OTHER PUBLICATIONS

Kinet et al., "Isolation and Characterization of cDNAs Coding For The β Subunit Of The High–Affinity Receptor For Immunoglobulin E", *Proc. Natl. Acad. Sci. USA,* vol. 85:6483–6487, (1988).

Kuester et al., "Characterization and Expression Of The Gene For The Human Fc Receptor γ Subunit", *The Journal Of Biological Chemistry,* vol. 265:6448–6452, (1990).

Alber et al., "Structure–Function Relationships In The Mast Cell High Affinity Receptor For IgE", *The Journal Of Biological Chemistry,* vol. 266:22613–22620, (1991).

Kuester et al., "The Gene and cDNA For The Human High Affinity Immunoglobulin E Receptor β Chain And Expression Of The Complete Human Receptor", *The Journal of Biological Chemistry,* vol. 267:12782–12787, (1992).

Maekawa et al., "Determination Of The Sequence Coding For The β Subunit Of The Human–Affinity IgE Receptor", *FEBS Letters,* vol. 302:161–165, (1992).

FIG. 2A

```
AAGCTTTTCA AAGGTGCAAT TGGATAACTT CTGCCATGAG AAATGGCTGA ATTGGACAC    60
AAGTGGGGAC AATTCCAGAA GAAGGGCACA TCTCTTTCTT TTCCTGCAGTT CTTTCTCACC  120
TTCTCAACTC CTACTAAAAT GTCTCATTTT CAGGTTCTGT AAATCCTGCT AGTCTCAGGC   180
AAAATTATGC TCCAGGAGTC TCAAATTTTC TTATTTCATA TTAGTCTTTA TTTAGTAGAC   240
TTCTCAATTT TTCTATTCAT CACAAGTAAA AGCCTGTTGA TCTTAATCAG CCAAGAAACT   300
TATCTGTCTG GCAAATGACT TATGTATAAA GAGAATCATC AATGTCATGA GGTAACCCAT   360
TTCAACTGCC TATTCAGAGC ATGCAGTAAG AGGAAATCCA CCAAGTCTCA ATATAATAAT   420
ATTCTTTATT CCTGGACAGC TCGGTTAATG AAAAAATGGA CACAGAAAGT AATAGGAGAG   480
CAAATCTTGC TCTCCCACAG GAGCCTTCCA GGTAGGTACA AGGTATTATT TTTTTCTACC   540
```

FIG. 2B

```
CTCAGTCACT TGTGGCAGGG GAAGTCATAG TCACGGTGCT TAGGAGATGA AACTTTATTG    600
ATTTAGGCAT GGATCCATCT AGTTAATTA ATATATTGGG TATGAGGAAG CTACTTGCTG    660
TACTTTCCAT GTGGTTCTCT CTCCCTGGAG AGGAACATTT TTACTCAGCT TGCAAACTGG   720
AAATAGATTT TCTCACATTA GAAGCTCATT TTCTGGGTAT GAGACAGGAG AGTTCATACT   780
GTGTATGTAG ATCTCTGGCT TCTGGGTCTG ACATGTGCTG AGGGACACAT ATCCTTCACA   840
CATGCTTTTA TAAATACTTG ATAAAGTAAC CTGCTTCTTG ATTGGTCTTT ATAATCCATA   900
AGCTGTGGGA TGCTTCTCTG AAGATGAAAA TAGTAATAGA GTCCCATCTA GCTATTCAAA   960
GCCATTCCTT CATTGTATTC TGTGCACATG AAGTTGGGGT TTGTTACTGA CAAAATATAT  1020
TCAGATACAT TTCTATGTTA AAAGGATTGT GAGATGCATA GGTAAATGTG TTTATTTCA   1080
GTTTTACTTG TCAACATAGA TGAATGAGAA AGAACTTGAA AGTAACACTG GATTAAGAAT  1140
```

FIG. 2C

```
AGGAAAATTT GGCATGGATT TTGCTCCATT TTGTCCCATC TAATCACTTG GATAGTGTTC  1200
AGGTGTTCTT GGTCAGTTAC TTGGATGCTC TGAGCTTTAG TTTCTTGGTG ATTACAATGA  1260
AGATTTGAAT TACAGGATGG CTTTGAAAAA ATAAACAAAA CTCCCCTTTC TGTCTGTCGA  1320
GAATGTTGCA CAGGGAGTTA CAGAATGTTC TCATGACTGA ATTGCTTTTA AATTTCACAG  1380
TGTGCCTGCA TTTGAAGTCT TGGAAATATC TCCCCAGGAA GTATCTTCAG GCAGACTATT  1440
GAAGTCGGCC TCATCCCCAC CACTGCATAC ATGGCTGACA GTTTTGAAAA AAGAGCAGGA  1500
GTTCCTGGGG GTGAGTGAGC CTCCTCCAAC TTTGACTAGA GTAAGGGTTG GGTCTAGAAA  1560
AGAATATTGA GTTGCATCAA CTGTTTTCCC ACTTGGATTC ATGAGAGGTG TTAGGTCCTT  1620
TAAAAAACAT GGTAGATAAA GAGTTGACAC TAACTGGGTC CTTTGGGAA GAGCCAGAAG  1680
CATTCCTCA TAAAGACTTT AAATTGCTAG GACGAGAATG GCCAACAGGA GTGAAGGATT  1740
CATAACTTTA TCTTTACTTA GATGTAAAGA ACAATTACTG ATGTTCAACA TGACTACATA  1800
CATAAAGGCG CATGGAGAAA AGTATTGGCC TTCCATGCAT TAGGTAGTGC TTGTATCAAT  1860
TCTTATAGTG GCTAGGGTAT CCTGGAAAAT CTTACGTGTG GATCATTTCT CAGGACAGTC  1920
TAGGACACTA ACGCAGTTTC TCATGTTTGG CTTCTATTAT TAAAAAATGA TACAATCTCG  1980
```

FIG. 2D

```
GGAAAATTT TTTGATTTTC ATGAAATTCA TGTGTTTTTC TATAGGTAAC ACAAATTCTG   2040
ACTGCTATGA TATGCCTTTG TTTTGGAACA GTTGTCTGCT CTGTACTTGA TATTTCACAC   2100
ATTGAGGGAG ACATTTTTTC ATCATTTAAA GCAGGTTATC CATTCTGGGG AGCCATATTT   2160
GTGAGTATAT ATCTATAATT GTTTCTGAAA TAACACTGAA CATAGGTTTT TCTCTTTCTC   2220
AGATCTAACC AGTTGTTTAT TCCCAGTATT AAGATGATAT TTATAATTCT TAATTATAAA   2280
TATATGTGAG CATATATAAC ATAGATATGC TCATTAACAA CAACAAAAGA TTCTTTTTAC   2340
AATTAACGGT GGGTTAAACA TTTAGCCCAC AGTTTTATCC CATGAGAAAC CTGAATCTAA   2400
TACAAGTTAA ATGACTTGCC TAAGGGCCAC TTGACTAATA GTAATTGAAC CTAAACTTTC   2460
AGAATCCAAC TCCAGGAACA TACTTCTAGC ACTATTCATC AATAAAGTTA TATGATAAAT   2520
ACATACAACT TTATCTGTCA ACTAAAAATA ACAACAGAGG CTGGGCATGG TGGCTCACAC   2580
CCGTAATCCC AGCACTTTGG GAGGCTGAGG CAGGTGGATC ACCTGAGGTC AGGAGTTTGA   2640
```

FIG. 2E

```
GACCAGCCTG ACCAACATGG TGAAACCTCA TCTCTACTAA ATATAAAAAA TTAGCTGAGT    2700
GTGATAGTGC ATACCTGTAA TCCAGCTACT TAAGAGGCTG AGGCAGGAGG CTTGTTTGAA   2760
CCTGGAAGGC AGAGGTTGCA GTGAGCTGAG ATTGTGCCAT TGCACTCCAG CCTGGGCAAT   2820
AAGTGCGAAC TCTGTCTCAA AATAATAATA ATAATATAAT AAAATAAAGT TGTCTTCATG   2880
AAAAATGAGG AAAGAGATTG CTGGGGTGAG AAACATTAAG ATCAATGGGC ATATGGTGAC   2940
CTTCTATGCC CTAGAAACTC TTTTANGGTA TTTCTCCCTG GTATCTCTTT TACNCATCGT   3000
TCTATCTGGA AAAATAGGTG GATGAGTGAG ATAATAACGG TATATACTTT TTAAAGGTCT   3060
AATTGACATA TATAAATTGC AAGTATTTCA GATGTCAATT TGCTAACCTT GACACACATA   3120
GACACACATG AAAACATCAC CACATTAATA CAATGTATGT ATCCATCATT CCAAAAGCTT   3180
CCCTGTGTAT CTTGTAACT CTTTCTTCCT CCCTCCACTC CTTGTCCTCT CGTTCCCAAG    3240
AAAACATTGA TCTGCTTCCT GTGAATATAA ATTAACTTAC ATTTTTTAGA GCTTTATATA   3300
AGTATGTTCT CTTTACTGTT TGTCTTCCTT CGCTGCACAG TTATTTGAG ATTCTTCAAG    3360
```

FIG. 2F

```
AGTATGTCTCT  CTTTACTGTT  TGTCTTCCTT  CGCTGCACAG  TTATTTGAG  ATTCTTCAAG   3360
TTTTTCTT    ATATCGATAC  TTCATTCACA  AGAATATATT  TTAATTCTAG  ACTATGTCAC   3420
ATTGACTTTG  TCGTCTGCTA  AATCCTTAGT  GCTCAGATGA  CTTGTTCAGG  ACTCTCCTTG   3480
AACCTGTACC  TCTGTTANAT  TGAAACTGT   CTCTACTGTC  TTTTTATTTC  AAACACAGCT   3540
TATTAGGTGT  CTCTCAACCC  ATCAAACNCA  CAATCTGAGT  CTTTAGGAGA  TTGCTTTGAA   3600
TTTGTGCTAT  TGACTTATAT  NTATATNAAA  TNTGTAAATG  TTTGGTAAAA  ATATCATCAT   3660
GTACNTTTC   ATAATTACGC  TATNTNCACA  TGATATATGT  CAGACTCTGG  AAATATGCAT   3720
GCCACAGACA  CGTGTTTCTT  GCCTAAAGGG  GCTGATGGAA  GACNCACATA  CNAATAGACG   3780
ATTGCAGTAG  AATGAGAGTG  GTGGTCTAAN  CAGTACACATGT CCTGATGTTG  CTCGGACAGT  3840
TACTACNCCA  AGAGTACCCC  CTGCCATTGTC  AGGGTTAGCA  TCTCCTGGAA  GCCCTCATGTA 3900
AATGAAGAAT  TTCATGCTCC  ATCCAGGACC  TAATGAATAA  GAATCTGCAT  TTTAGCAAGA  3960
CCCTCATATG  ATTCATATAC  ACTTTTTTTT  TTTTTTTTA   GATGGAGTCT  CACTCTTGTC  4020
```

FIG. 2G

```
GCCCAGGCTG GAGTGCAATG GCATGATCTT GGCTCACTGC AACCTCTGCC TCCCGGGTTC    4080
AAGTGATTCT CCTGTCTCAG CCTCCCTAGT AGCTGGGACT ACAGGTGCAT GCCACAGTGG    4140
CTGGCTAATT TTTGTATTTT TAGTAGAGAC AGGGTTTCAC CATTTTGGTC AGGCTGGTCT    4200
TGAACTCATG ACCTCCGGTG ATTCCCCCGC CTCGGCTTCC CAAAGTGCTG GGATTACAGA    4260
CATGAGCCAC CACACCCGCC TTATTCGTAT ACNCATTTAA TTCTGAGAAG CACTCTATAG    4320
AAAATAAGAA TAAGAAAATA TTGGGCTCAC AGTGACATT AATAAGTAAC TTTATCGAGT    4380
ACCCCAAATT TTACCTATGT TTGGAAGATG GGGTTAAAAG ACAGTTTCT GACACATTGA AAACAAGAAC    4440
TCATTGTGGC TTTTTTTCC TCCTTTTTGA ACAGTTTCT ATTCTGGAA TGTTGTCAAT    4500
TATATCTGAA AGGAGAAATG CAACATATCT GGTGAGTTGC CCGTTTCTGT CTTTGTCCAT    4560
CCTTGAAAAG ATAAGAAGAA CAGAGTTTTA AGAGTCTTAA GGGAAACACA TCTTTGTCTC    4620
CTATATTACT TGTGAATGTG GATATATGAT TTTGTTTCAA TCTATTTTGT GTCCTAAGGC    4680
```

FIG. 2H

| | | | | | 4740 |
|---|---|---|---|---|---|
| TTTTGCAAC | AGAAGTTGGA | TATATCATTA | GAAACATAAA | TTGTACCATT | TAACATACAT |
| GAAGTTTATG | TTTACCTTGA | CGTCTCTCTA | AAAAGTGTCC | TACACCGGCA | TTGTCCTTGT | 4800 |
| AGGCATATTC | ACATGATCAA | ATAAAATAAT | TAGTTTTCAA | TTAAGGAGAA | TATTTGAGGA | 4860 |
| AAGACCCGTAC | GTGTTCATGT | GGTTCCTGAA | GGCAGTCCAG | TGAGAAAGTA | ATATATGCTT | 4920 |
| CATTAAACAA | TGCGGACATT | TTCAGGGTTT | CCCTTTTTAA | CCAAAATTTG | GAAGCAATGT | 4980 |
| GGAATTACT | GGATGCATCC | AGCCCTGAAA | TGAAGATAGG | TTTATTGAAT | GTGCCAGCAA | 5040 |
| GTGCAGGCCC | AGGTCTGAGT | GTTCTTCATT | ATTATCAGT | GAGAGGAAGC | CTGGGAGCAA | 5100 |
| ACACTGCCAG | CAGCATAGCT | GGGGAACGG | GAATTACCAT | CCTGATCATC | AACCTGAAGA | 5160 |
| AGAGCTTGGC | CTATATCCAC | ATCCACAGTT | GCCAGAAATT | TTTGAGACC | AAGTGCTTTA | 5220 |
| TGGCTTCCTT | TTCCACTGTA | TGTATTTTTT | TTGTGTGGG | AAGACTAAGA | TTCTGGTCC | 5280 |
| TAATGTAAGT | AAGAAGCCCT | CTTCTCCCTGT | TCCATGAACA | CCATCCTTTT | CTGTAACTTC | 5340 |

FIG. 21

```
TATTACACAG TATAGTGGTT CTGTAAGTTC ACACAGCCCA GGGAGATGCT GGCTGCCCAC  5400
TCCCCTCAAC CCAGGCAAAT TCCCTCGGGGT TAAAGTTATC TACTGCAAGT GACGATCTCT  5460
GGGTTTTCT GTGCCTGTGT TTGTGTGTGT GTGTGTGTGT GTATGTGTCA  5520
CTTTAAAAGG ACTGGTCAGA ATGAAAACAG GAGATGCTAT AAGAAAATAA  5580
ACTTTGGGG CGAATACCAA TGTGACTCTT TTTGTTTGTC ATTTGTTGCT GTTCAATAGG  5640
AAATTGTAGT GATGATGCTG TTTCTCACCA TTCTGGGACT TGGTAGTGCT GTGTCACTCA  5700
CAATCTGTGG AGCTGGGGAA GAACTCAAAG GAAACAAGGT AGATAGAAGC CCGATATAAA  5760
ATCTTGAATG ACAGGTTAAC GAATTGGAGC TTTATTCCTT AAAATATGGC CTGGGTTTTC  5820
TGAAACATTT CTTCCAGAAA ATAGTTTCTC CAAGTTTTAT TACTTTGGTT TACAAATCTC  5880
ACATTAAAT CACATTTTAT ACCATAAGTA GCACACATTT CATAATATTC CTCTGAATGA  5940
GGGTTGGGAT AATAGGACTG ATATGTTAGA AATGCCTTAA AGTGTGTGGA GCATGAGAGA  6000
TGGATGTACA GAAGGCTTGT GAGGAAACCA CCCAGGTATC TGGCCTTGTT TTCTGCCCCA  6060
```

FIG. 2J

```
GAACTAGCCG CCTATTCCTG TTTCTGTTTT ATTCCTTTGT TTCTTGACTT TTCCTTTCCA    6120
ACTTGCTCTA AAACCTCAGT TTTCTTCCT TTCTGATTCA TGACTACCAA ATGTTTCAC    6180
TTGCCTCACC CGTCCATTAC ACCTTTGATA AGAACCACCA GACCTTGTGC TCATGTACTT    6240
GCCCATGTCT GATGGAAGAA ACATACTCTC TCCATCTGTC CACTTCCCTG AGGCATTCAA    6300
GTCTAGCCAC CTTTAAAAT CACTCTCCTC CAGGCTGGGC ACGGTGTCAC GCCTGTAATC    6360
TCAGCACTTT GTGAGGCTGA GGAGGGCGGA TCACTTGAAG TCAGGAGTTC AAAACCAGCC    6420
TGGCCAAATG GCAAAACCAA ATCTTCTTCA ATTATAACCA AATCTTAAAC CAAATCTCTA    6480
CTAAAAAATA CAACAAAACA AAACAACAAC GAAAAGGAAA CATTAGCCCA    6540
GCGTGGTGGC AGGTACCTGA GGTTCCAGAT ACTGGGAGG CTGAAGCAGG AGAATCGCTT    6600
GAGCCCAAGA GATGGAGGTT GCAGTGAGCC GAGATCATGC CACTGCACCA CAGCCAGGGT    6660
GACAGAGCCA TACTTCCCAG CACATTGGGA GGCCAAAGCT GAAGAATAAT TTGAGGTGAG    6720
```

FIG. 2K

```
GATTGGAGA CCAGCCTGGC CAACATGGTG AAACTCCGTC TGTACTAAAA ATATAAACT     6780
TAGTGGGGCA TGGGGCACA CACCTGTAAT TTCAGCTACT TAGGAGGCTG AGGCAGGAGA    6840
ATTGCTTGAA CCCGGGAGGC GGAAGTTGCA GTGAGCCAAG ATCGTGGCCA CTGCACTCCA   6900
GCCTGGGTGA CATAGTGAGA TTCTGTCTCA AAAAAAATAA AAGAAATTTA AAAAATCACT   6960
CTCTTCCAAA GATAGATAAA TAAGACAGCA GATATACTAA GGAATAACCT CACCAACTTG   7020
TCATTGACTG ACATGATTTC CTTGGCCCCA CTTGGCCAGC TAGTCTGGTT TGGTTTTCTG   7080
GAAATGAAAG AAATAATCAG AGTTAATGA CAGAGAGCGT GAGACCCAGA AAGACAAAAG    7140
TAGATGAGGT AAGTCTCTTG AGCGAGACTT CTAGGGATGG GAAATTGTGT GTGATTGATA   7200
TGAAATGATT TTTCCCTTAT CAGGTTCCAG AGGATCGTGT TTATGAAGAA TTAAACATAT   7260
ATTCAGCTAC TTACAGTGAG TTGGAAGACC CAGGGGAAAT GTCTCCTCCC ATTGATTTAT   7320
AAGAATCACG TGTCCAGAAC ACTCTGATTC ACAGCCAAGG ATCCAGAAGG CCAAGGTTTT   7380
```

FIG. 2L

```
GTTAAGGGGC TACTGGAAAA ATTTCTATTC TCTCCACAGC CTGCTGGTTT TACATTAGAT  7440
TTATTCGCCT GATAAGAATA TTTTGTTTCT GCTGCTTCTG TCCACCTTAA TATGCTCCTT  7500
CTATTGTAG ATATGATAGA CTCCTATTTT TCTTGTTTTA TATTATGACC ACACACATCT   7560
CTGCTGGAAA GTCAACATGT AGTAAGCAAG ATTAACTGT TTGATTATAA CTGTGCAAAT    7620
ACAGAAAAAA AGAAGGCTGG CTGAAAGTTG AGTTAAACTT TGACAGTTG ATAATATTTG    7680
GTTCTTAGGG TTTTTTTTTT TTTTAGCATT CTTAATAGTT ACAGTTGGGC ATGATTGTA    7740
CCATCCACCC ATACCCACAC AGTCACAGTC ACACACACAT ATGTATTACT TACACTATAT   7800
ATAACTTCCT ATGCAAATAT TTTACCACCA GTCAATAATA CATTTTGCC AAGACATGAA    7860
GTTTTATAAA GATCTGTATA ATTGCCTGAA TCACCAGCAC ATTCACTGAC ATGATATAT    7920
TTGCAGATTG ACAAGTAGGA AGTGGGGAAC TTTTATTAAG TTACTCGTTG TCTGGGGAGG   7980
TAAATAGGTT AAAAACAGGG AAATTATAAG TGCAGAGATT AACATTCAC AAATGTTTAG    8040
TGAAACATTT GTCAAAAAAG AAGACTAAAT TAAGACCTGA GCTGAAATAA AGTGACGTGG   8100
```

FIG. 2M

```
AAATGGAAAT AATGGTTATA TCTAAAACAT GTAGAAAAAG AGTAACTGGT AGATTTTGTT  8160
AACAAATTAA AGAATAAAGT TAGACAAGCA ACTGGTTGAC TAATACATTA AGCGTTTGAG  8220
TCTAAGATGA AAGGAGAACA CTGGTTATGT TGATAGAATG ATAAAAAGGG TCGGGCGCGG  8280
AGGCTCACGC CTGTAATCCC AGCCCTTTGG GAGGCCGAGG TGGGCAGATC ACGAAGTCAG  8340
TAGTTTGAGA CCAGCCTGGC CAACATAGTG AAACCCCGTC TCTACTAAAA ATACAAAAAA  8400
AAAATTAGCT GGGTGTGGTG GCAGTCACCT GTAGTCCCAG CTACTTGGGA GGATGAGGCA  8460
GGAGAATCGC TTGAACCTGG GAGGCGGAGG TTGCAGTGAG CCGAGATCGC ACCAGTGCAC  8520
TCCAGCCTTG GTGACAATGG GAGACTCCAT CTCAAAAAAA AAAAAAAAAA AAAAAAGATA  8580
AAAAGTCAGA AATCTGAAAA GTGGAGGAAG AGTACAAATA GACCTAAATT AAGTCTCATT  8640
TTTGGCTTTT GATTTGGGG AGACAAAGGG AAATGCAGCC ATAGAGGGCC TGATGACATC  8700
CAATACATGA GTTCTGGTAA AGATAAAATT TGATACACGG TTTGGTGTCA TTATAAGAGA  8760
```

FIG. 2N

```
AATCATTATT AAATGAAGCA AGTTAACACT CTAAGAGAAT TATTTGAGA TAGAAGTGAA    8820
GCTAAGCTAA ACTTCACATG CCTATAATTG GAGGGAAAAA CTAAGGATAA AATCTAGCCT   8880
AGAAGATACA ATAATTAGTC ATAAACATGC ATTGTGAAAC TGTAGAGAGC AGGTAGCCCA   8940
AAATAGAGAA AGATTAGATA AAGAGAAAAT AAGTATCCAT CAGAGACAGT ATCTCTAGGC   9000
TTGGGCAAGA GAAAAGTCCA CAGTGATAAG CAACTCCACC TAAGGCATGA ATATGCGGCA   9060
GAGAAAACAG CAATAGTGAA TGAATGCAAA AGGTGCTGAG CAAATTCCAC ACATGAGTAT   9120
TGTGCATGAG TAAATGAATA AAACATTTGC AAAGACCTTT AGAGAAAGAG AATGGGAGCA   9180
TATGTGCGAA ATAAGATAGT TGATTATGAA TAGAAGGTAG TAGTTTATGT CAAGCTAAGA   9240
AAAAATCTG TTTATAAAAG AAGGAAAAGA TAGTTTATGT TTTTAGCCTA AGTATAAGAG   9300
TCCTACAGAT GGACTGAAAA AAATCAGTCT GAGAGTATTA GTCACAATTA ATGAAATAAT   9360
TACATTTAT GTATTGAGGA TGCCAAGATT AAAAGGTGAC AGGTAGATGT TAATTCCCT    9420
```

FIG. 20

| | | | | | |
|---|---|---|---|---|---|
| AGATTGTGAA | AGTGATCACG | ACAATCACAC | AACAAATAAT | TAAGTGACTT | GGTATGCTTT | 9480 |
| ATTAATTGT | AGGGCCTGAG | GTTTTCCATT | CTCATTTTTC | TAAAATACAA | TTTTGTTTCT | 9540 |
| CCAAATTTGA | CAGCAGAATA | AAAACCCTAC | CCTTTCACTG | TGTATCATGC | TAAGCTGCAT | 9600 |
| CTCTACTCTT | GATCATCTGT | AGTATTAAT | CACATCACTT | CCATGGCATG | GATGTTCACA | 9660 |
| TACAGACTCT | TAACCCTGGT | TTACCAGGAC | CTCTAGGAGT | GGATCCAATC | TATATCTTTA | 9720 |
| CAGTTGTATA | GTATATGATA | TCTCTTTTAT | TTCACTCAAT | TTATATTTTC | ATCATTGACT | 9780 |
| ACATATTTCT | TATACACAAC | ACACAATTA | TGAATTTTTT | CTCAAGATCA | TTCTGAGAGT | 9840 |
| TGCCCCACCC | TACCTGCCTT | TTATAGTACG | CCCACCTCAG | GCAGACACAG | AGCACAATGC | 9900 |
| TGGGTTCTC | TTCACACTAT | CACTGCCCCA | AATTGTCTTT | CTAAATTTCA | ACTTCAATGT | 9960 |
| CATCTTCTCC | ATGAAGACCA | CTGAATGAAC | ACCTTTTCAT | CCAGCCCTAA | TTTCTTGCTC | 10020 |
| CATAACTACT | CTATCCCACG | ATGCAGTATT | GTATCATTAA | TTATTAGTGT | GCTTGTGACC | 10080 |
| TCCTTATGTA | TTCTCAATTA | CCTGTATTTG | TGCAATAAAT | TGGAATAATG | TAACTTGATT | 10140 |

FIG. 2P

```
TCTTATCTGT GTTTGTGTTG GCATGCAAGA TTTAGGTACT TATCAAGATA ATGGGGAATT    10200
AAGGCATCAA TAAAATGATG CCAAAGACCA AGAGCAGTTT CTGAAGTCCT CCTTTTCATC    10260
AGCTCTTTAT CAAACAGAAC ACTCTATAAA CAACCCATAG CCAGAAAACA GGATGTAGGA    10320
ACAATCACCA GCACACTCTA TAAACAACCC ATAGCCAGAA AACAGAATGT AAGGACAATC    10380
ACCAGCCATC TTTGTCAAT AATTGATGGA ATAGAGTTGA AAGGAACTGG AGCATGAGTC     10440
ATATTTGACC AGTCAGTCCT CACTCTTATT TACTTGCTAT GTAAACTTGA GAAAGCTTTT    10500
TTCTCTTTGT GAACCTCAGG TTTTACATCT GAAAATGAGA AATTTGGAAC AAAAGATTCC    10560
TAACTGGTCT TTCTGTTCCC ATATTCTGTG ATTTTTCAAT ATTTAGGATT TTTGGTAATC    10620
ACAATTACTT AGTTTGTGGT TGAGATAGCA ACACCAATCA GAACTATTTG GTGGACATAT    10680
TTTCAAAGGA GTAGCTCTCC ACTTTGGGTA AAGAAGTGAT GCNGGTCGTG GTGGCTCACG    10740
```

FIG. 2Q

```
CCTGTAATCC CAGCACTTTA GGGAGGCCAA GGCGGGTGGA TCACGAGGTC AGGAGATCGA    10800
GACCATCCTG GCTAACACGG TGAAACCCCG TCTCTACTAA AAAATACAAA AAATTAGCCA    10860
GGCGTGGTGG CGGGCCCTG TAGTCCCACG TACTCGGGAG GCTGAGGCAG GAGAATGGCA    10920
TGAACCAGGG AGGCGGAGCT TGCCGTGAGC CGAGATAGCG CCACTGCAGT CCCTCCTGGG    10980
CAAAGAGAGCA AGACTGCGTC TCAAAAAAAA AAAAAAAAAA AAAAAAAGAA GTGTGTGGAG    11040
TAGCAGGACA CCTGCAACAA TAATATATTTT CTAAATCCCT CTGAAAAATG CTAATCAAAG    11100
GGTTTTTTTC CTAAAAATTG TCTTAGAAAT AAAATTCCC CTTTGGGAGA CCGAGGCTGG    11160
CAGATCACGA GGTCAGGAGA TAGAGACCAC GGTGAAACCC CGTCTCTACT AAAAATACTA    11220
AAAATTAGCC GGGGNTGGT GGTGGGTACA CCTGTAGTCC CAGCTACTTG GAGGCTGAGG    11280
CTGGAGAATC ACCTGAAC                                                  11298
```

FIG. 7A

```
human  MDTES NRRAN LA--L PQEPS SVPAF EVLEI SPQEV SSGRL
         ^^^^^    ^^^     ^^^   ^^^^  ^^^^^ ^^^^^
rat    MDTEn ksRAd LAlpn PQEsp SaPdi ELLEa sPp-a kalp-
         ^^^^^  . ^^^  ^  ^^^  .^ .^  ^^^^   .  :  :  .   ---
mouse  MDTEn rsRAd LAlpn PQEsS SaPdi ELLEa SP--- --a--   .
         ^^^^^    ^^^    ^^^   ^^^^  ^^^^^

LKSAS SPPLH TWLTV LKKEQ EFLGV TQILT AMICL CFGTV VC
                        ^^^^^       ^^^^^ ^^^^^ ^^
eKpAS pPPqq TWqsf LKKEl EFLGV TQvLv qlICL CFGTV VC
^ ^^^   ^^    ^  ^^^^  ^^^^^ ^^ ^^   ^^^ ^^^^^ ^^
-K-A- aPPkq TWrTf LKKEl EFLGa TQILv qlICL CFGTi VC
      ^^    ^  ^ ^^^^  ^^^ ^ ^^^^^   ^^^ ^^^ ^ ^^

SVL DISHI EGDIF SSFKA GYPFW GAIFF SISGM LSIIS
              ^^^^  ^^^^^       ^^^^^ ^^^^^
stL qtSdf ddevl llyrA GYPFW GAvlF vlSGf LSImS
^ ^  ^ ^   ^^ ^ ^^ ^ ^^^^^ ^^ ^^ ^ ^^  ^^ ^
SVL yvSdf deevl llykl GYPFW GAvlF vlSGf LSIIS
^^^  ^^^   ^^ ^ ^^  ^ ^^^^^ ^^ ^^ ^ ^^  ^^^^^
```

*FIG. 7B*

```
ERRNA TYLVR GSLGA NTASS IAGGT GITIL IINLK KSLAY IHIH

ERkNt lYLVR GSLGA NivSS IAaGl GIaIL IlNLs nnsAY mn-y
^^^^.  ^^^^ ^^^^^ ^..^^ ^^.^   ^^.^^ ^^^^.  ..  ^^ ^^  .
ERkNt lYLVR GSLGA NivSS IAaGT GIamL IlNLt nnfAY mn-n
^^^^.  ^^^^ ^^^^^ ^..^^ ^^.^^ ^^.^^ ^^^^.  ..^^^ ^^  ^

S CQKFF ETK-C FMASF STEIV VMMLF LTILG LGSAV SLTIC

- Ckdit EddgC FvtSF iTElV lMlLF LTILa fcSAV lLiIy
  ^...  ^..  ^ ^^.^^ .^^^^ ^^^^^ ^^^^.  ^ ^^^   ^.^.
- Cknvt EddgC FvASF tTElV lMMLF LTILa fcSAV lfTIy
  ^...  ^..  ^ ^^^^^ .^^^^ ^^^^^ ^^^^.  ^ ^^^   ^^^.

GAGEE LKGNK VPEDR VYEEL NIYSA TYSEL EDPGE MSPPI DL riGqE fersK VPdDR lYEEL hvYSp iYSaL EDtrE aSaPv vs
 .^^^ ^.  .^ ^^^^^ ^^^^^ ^^^^.  .^^.^ ^^.  ^  .^.^^
riGqE LeskK VPdDR lYEEL NvYSp iYSEL EDkGE tSsPv Ds
 .^^^ ^...^ ^^^^^ ^^^^^ ^^^^.  .^^^^ ^^.^^ .^.^^ ^
```

FIG. 11A
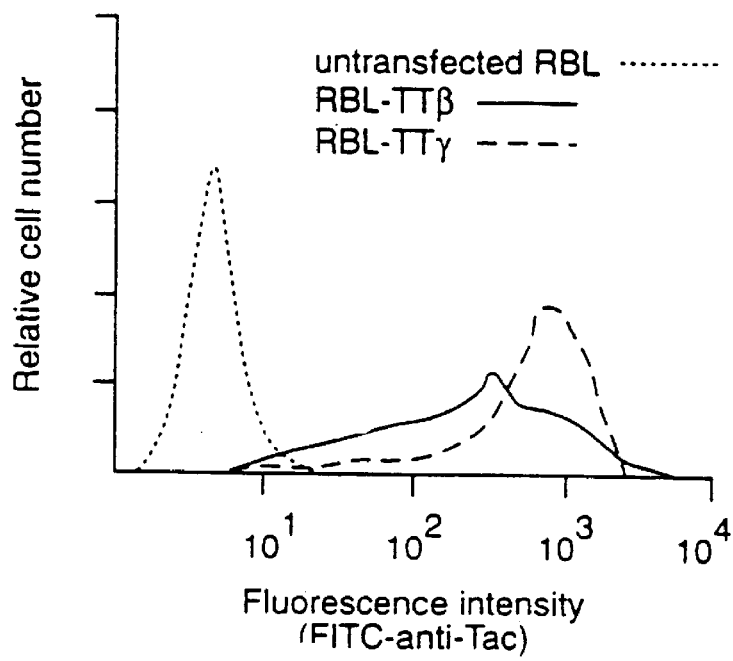
FIG. 11B
| cell line | Ab | average binding sites/cell |
|---|---|---|
| RBL-TTβ | anti-Tac | 400000 |
| RBL-TTβ | IgE | 420000 |
| RBL-TTγ | anti-Tac | 880000 |
| RBL-TTγ | IgE | 480000 |
FIG. 11C
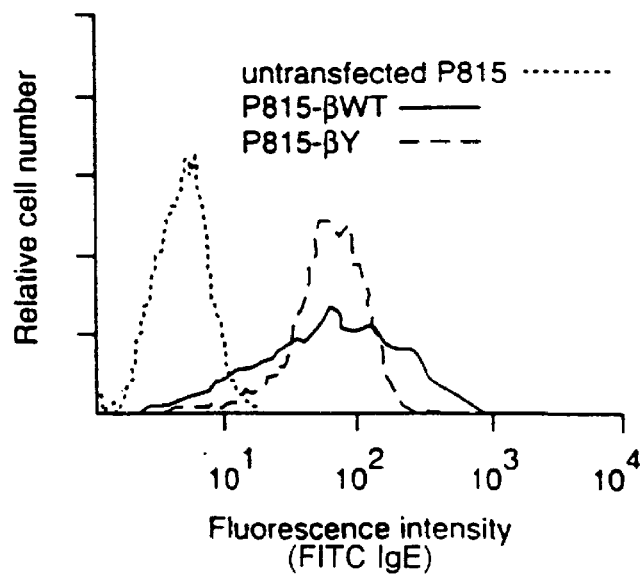

ISOLATION, CHARACTERIZATION, AND USE OF THE HUMAN AND SUBUNIT OF THE HIGH AFFINITY RECEPTOR FOR IMMUNOGLOBULIN E

BACKGROUND OF THE INVENTION

This application is a CIP of U.S. Ser. No. 07/869,933, filed Apr. 16, 1992 which is a PCT/US 93/03419, filed Apr. 16, 1993, both of which are incorporated herein by reference.

The present invention relates to DNA segments encoding the $\alpha$, $\beta$ and $\gamma$ subunits of the high affinity receptor for immunoglobulin E (IgE), more particularly to the human $\beta$ subunit, including the ARAM-containing C-terminal tail of the $\beta$ subunit antigen recognition activation motif. The invention further relates to a method of producing the receptor by expressing DNA encoding its $\alpha$, $\beta$ and $\gamma$ subunits in a host cell simultaneously, and to assays for inhibitors for an IgE-mediated allergic response.

Receptors that bind the Fc region of immunoglobulins ("Fc receptors") mediate immunoglobulin transport across membranes, stimulate a variety of cellular activities induced by antigen-antibody complexes, and possibly regulate the biosynthesis of antibodies. Three such receptors—the receptor for polymeric immunoglobulin (Mostov et al., 1984), the Fc receptors on macrophages and lymphocytes (Ravetch et al., 1986), and the high affinity Fc receptor on mast cells and basophils (Kinet et al., (1987); (Shimizu et al., (1988); Kochan et al., 1988) share a common feature, namely, their immunoglobulin-binding portion contains two or more immunoglobulin-like domains.

The high affinity IgE receptor Fc$\epsilon$RI is responsible for initiating the allergic response. Binding of allergen to receptor-bound IgE leads to cell activation and the release of mediators, such as histamine, which are responsible for the manifestations of allergy. This receptor is a tetrameric complex $\alpha\beta\gamma_2$ which is found on the surface of mast cells, basophils, eosinophils, Langerhans cells, and related cells.

The genes for $\alpha$ and $\gamma$, both have been localized on human (Le Coniat, 1990) and mouse chromosome 1. (Huppi, 1988; Kinet et al., 1987). The gene for mouse $\beta$ has been localized on mouse chromosome 19 and is believed to be a single gene (Huppi, 1989). The structures of the $\alpha$ gene in the rat (Tepler, 1989) and of the $\gamma$ gene (Kuster, 1990), but not of the $\beta$ gene have been characterized in the human.

Aggregation of IgE occupied Fc$\epsilon$RI by antigen triggers both the release of preformed mediators such as histamine and serotonin, as well as stimulation of the synthesis of leukotrienes. It is the release of these mediators that results in the allergic condition.

The most thoroughly characterized Fc$\epsilon$RI is that of the rat basophilic leukemia (RBL) cell line. It consists of three different subunits: (1) a 40–50 Kilodalton (Kd) glycoprotein alpha chain which contains the binding site for IgE, (2) a single 33 Kd beta chain and (3) two 7–9 Kd disulfide linked gamma chains (H. Metzger et al., 1986).

Complementary DNA (cDNA) for the rat $\alpha$ subunit has been isolated (Kinet et al., 1987). However, prior to the present invention, there has been no disclosure of the isolation and characterization of the human $\beta$ subunit nor has it been possible to express IgE-binding by transfected cells (Kinet et al., 1987; Shimizu et al., 1988).

Molecular cloning of some of the subunits in rodents and humans has permitted the reconstitution of surface expressed receptor complexes by transfection. One of the surprising findings from these studies was the differential requirement for surface expression among different species. Cotransfection of the three chains, $\alpha$, $\beta$ and $\gamma$ is required to promote efficient surface expression of the rat (Blank, 1989) or mouse receptor (Ra, 1989). By contrast, some surface expression of the human $\alpha\gamma$ complex can be achieved by cotransfecting $\alpha$ and $\gamma$ alone suggesting that $\beta$ may not be necessary (Miller, 1989). This result and previous inability to clone the gene for the human $\beta$ subunit raised the possibility that human beta might not exist and that $\alpha\gamma$ complexes might exist naturally in human cells.

Nonreceptor tyrosine kinases such as the 70-kDa (ZAP-70/Syk) and Src-related tyrosine kinases are coupled to a variety of receptors, including the antigen receptors on B- and T-cells and the Fc receptors for IgE (Fc$\epsilon$RI) and IgG (Fc$\gamma$RI, Fc$\gamma$RIII/CD16). Nonreceptor tyrosine kinases of the Src and ZAP-70/Syk families are activated by engagement of these antigen receptors. This activation is the earliest detectable event in the signaling cascade initiated by these receptors, and results in the tyrosine phosphorylation of cellular proteins, including receptor subunits. The antigen receptors form a family of structurally and functionally related multisubunit receptors, including the B- and T-cell antigen receptor (TCR), the high (Fc$\gamma$RI) and low affinity (Fc$\gamma$RIII/CD16) Fc receptors for IgG and the high affinity IgE receptor (Fc$\gamma$RI).

A protein sequence motif $D/EX_2YX_2LX_{6/7}YX_2L$, which has been designated "antigen recognition activation motif" or ARAM (Samelson and Klausner, 1992; Weiss, 1993), has been identified in the cytoplasmic tails of some subunits within these receptors (Reth, 1989). When expressed independently of the other subunits, ARAMs are apparently able to elicit the full range of activation including the activation of tyrosine kinases.

Chimeras containing the cytoplasmic portions of TCR $\zeta$, CD3 $\epsilon$, and Fc$\epsilon$RI $\gamma$ activate early events in T-cells, such as calcium flux, as well as late events, such as interleukin-2 (IL-2) production. Chimeric proteins bearing the cytoplasmic portions of Fc$\epsilon$RI $\gamma$ and $\zeta$ invoke serotonin release from transfected RBL cells. In B-cells, a $\gamma$ chimera mediates antigen presentation. Mutation of either of the tyrosine residues in the ARAMs of CD3 $\epsilon$, TCR $\zeta$ and Fc$\epsilon$RI $\gamma$, respectively, abolishes signal transduction.

Some receptors harbor multiple forms of ARAMs. For example, within the TCR-CD3 complex, each $\zeta$ chain possesses three ARAMs, and the $\gamma$, $\delta$ and $\epsilon$ chains of CD3 have one ARAM each. The functional significance of this variation and multiplicity is unclear. Independent expression of each of the two N-terminal ARAMs of $\zeta$ indicates that they are qualitatively equivalent and that the main effect of the triplication is an amplification of the signals. Two different forms of ARAM are present in Fc$\epsilon$RI, a tetrameric $\alpha\beta\gamma_2$ complex, one in the C-terminal cytoplasmic part of $\beta$ and one in each of the two $\gamma$ chains.

ARAM-$\gamma$ in Fc$\epsilon$RI can induce serotonin release when expressed alone. The evidence for involvement of ARAM-$\beta$ in signaling is contradictory, however. On one hand, both rat Fc$\epsilon$RI, which requires the presence of all three types of subunits ($\alpha$, $\beta$, and $\gamma$) for cell surface expression, and its human counterpart, for which $\alpha$ and $\gamma$ suffice, elicit the same spectrum of activation reactions in transfected P815 mast cells. On the other hand, deletion of the C-terminal cytoplasmic tail of $\beta$ containing ARAM-$\beta$, but not deletion of the N-terminal cytoplasmic domain, which lacks an ARAM motif, abrogates activation responses in P815 (Alber et al., 1991).

The present invention addresses the ARAM function in the human β subunit, provides a method for producing complete human FcεRI receptor in vitro methods, and for inhibiting β-related functions.

SUMMARY OF THE INVENTION

It is an aspect of this invention to provide nucleic acid segments encoding FcεRI subunits.

It is an aspect of this invention to provide nucleic acid sequences encoding the α, β, and γ subunits of FcεRI. In particular, this invention relates to DNA sequences. An aspect of the present invention is the structural characterization and the sequence of the complete human β gene and cDNA.

The high affinity IgE receptor FcεRI is a tetrameric hetero-oligomer composed of an α chain, a β chain and two disulfide-linked γ chains (chains and subunits will be used interchangeably herein). The β chain contains four transmembrane (TM) segments and long cytoplasmic domains which are thought to play an important role in intracellular signalling. It was very difficult to determine from the art whether a human beta subunit even existed, and if so, how to isolate its gene when the problem's existence was suspect. The present invention overcomes these difficulties and, surprisingly, provides cDNA clones for the human β subunit of FcεRI.

Successful cloning of the human beta was not expected and was fraught with failures. Attempts to clone the human beta by simply using a rodent beta probe to screen various cDNA libraries failed to isolate a cDNA clone encoding human beta. Only a very short fragment (153 bp) with homology to rodent beta was isolated. Because this fragment may have been a portion of a beta-like molecule such as CD20, known to be homologous to beta in that region, PCR techniques were used to clone the human beta by using the information from the rodent beta sequence. The homologies between human and rodent beta of 69% in the coding region proved insufficient, however, for a PCR reaction. Human beta isolation by this method also failed.

The existence of human beta was questioned because human beta was believed not to be necessary for expression of the alpha-gamma complex. Studies of gene transfer indicated that the transfer by transfection of the three genes for alpha, beta and gamma was necessary for the expression of the rat and mouse receptor. However, transfection of human alpha and gamma was sufficient to promote the surface expression of the human receptor in fibroblasts suggesting that the human beta was not necessary for the surface expression of the human receptor. That result raised the interesting question of the existence of human beta.

Human beta was not necessary for the function of the alpha-gamma complex. Transfection of the cytoplasmic tail of gamma is sufficient for cell activation. Several groups made the observation that the cytoplasmic domain in the gamma chain was sufficient to mediate a number of biochemical signals leading to cell activation. These signals include tyrosine kinase activation, hydrolysis of phosphoinositides, calcium mobilization, production of IL2 in T cells, degranulation of mast cells and cell killing. It was demonstrated that the cytoplasmic domains of gamma contain a motif of 10–12 amino-acid residues responsible for cell activation. This motif is sufficient to trigger many different signals in different cells. It is transferable, and seemed to be interchangeable. Again these findings raised the question of the existence of human beta. If the gamma chain is sufficient for cell activation, perhaps there was no need for a beta.

The inability to clone the human beta or even to detect transcripts for human beta in human cells (by using rat or mouse probes) also raised the question of the existence of human beta.

Cloning required inventive methods and persistence. The 153 bp fragment used to screen further cDNA libraries did not work. However, assuming that the 153 bp could be part of human beta even though the homology was only about 70%, a 25 kb genomic clone was found. Smaller inserts were found which seemed to hybridize specifically with oligonucleotide probes corresponding with rat beta sequences. All these inserts (a total of 11 kb) were sequenced to reconstitute the different exons in the quest for those encoding human beta. Using what should be the beginning of the first exon and the end of the coding sequence in the seventh exon from the putative human beta gene, a putative cDNA human beta sequence was generated by PCR (by using first strand reverse transcripts from human basophils as templates for the PCR reaction).

It was demonstrated that the gene and cDNA isolated encoded human beta. The isolated gene and cDNA could correspond to a beta-like or CD20-like molecule which is homologous to rodent beta. However, the homology of 69% is not a criteria for the demonstration that these sequences encode human beta. Co-expression of alpha, beta and gamma in transfectants was preferred for the demonstration that the cDNA generated is indeed encoding human beta.

But these experiments were not successful for the following reasons:

1. Co-transfection of human alpha and gamma is sufficient for surface expression and functional reconstitution of the receptor on fibroblasts.
2. When human beta cDNA is co-transfected with alpha and gamma, the efficiency of transfection is not increased.

Conditions therefore were imposed such that co-transfection of alpha and gamma did not work, thereby to determine if human beta and not CD20 could promote expression of the complete complex. This was accomplished by truncation of the cytoplasmic tail of human gamma. Under these conditions, co-transfection of human alpha with truncated human gamma does not result in the expression of the complex. However, co-transfection of human beta (but not of CD20) with alpha and truncated gamma resulted in the expression of a functional complex capable of binding IgE. This assay showed that human beta could associate specifically with the two other chains.

The following results demonstrated the previously unsuspected importance of human beta. The two FIGS. 8 and 9 show the results obtained from FACS analysis (IgE binding) of cells transfected as explained herein. In FIG. 9 the transfection of human alpha and gamma in COS-7 cells is shown to be sufficient for expression of the alpha-gamma complex on the surface of the transfectants. It also shows that human beta and not rat beta associates efficiently with human alpha and that therefore, rat beta cannot replace human beta.

Transfection of alpha-gamma in KU812 showed very little expression of receptors (see FIG. 8). The level of expression is similar to the level obtained after transfection of beta and gamma. Therefore this level may be attributable to the endogenous alpha (for beta and gamma transfection) or to the endogenous beta (for alpha and gamma transfection). By contrast the level of expression after co-transfection of the three cDNAs is very substantial.

The conclusions from the results discussed in the previous paragraphs are:

1. In mast cells and basophils, what regulates the level of expression of the receptor may be different than in fibroblasts.
2. In human mast cells and basophils, receptor expression requires the presence of alpha, beta and gamma genes whereas in transfected fibroblasts, human alpha and gamma are sufficient.

The beta subunit gene spans approximately 10 kb and contains seven exons. There is a single transcription initiation site preceded by a TATA box. The first exon codes for the 5' untranslated region and a portion of the N-terminal cytoplasmic tail. Transmembrane (TM) 1 is encoded in exon 2 and 3, TM 2 in exon 3 and 4, TM 3 in exon 5 and TM 4 in exon 6. The seventh and final exon encodes the end of the C-terminal cytoplasmic tail and the 3' untranslated sequence. The human β gene appears to be a single copy gene.

Two corresponding transcripts, detected as a doublet around 3.9 kb, are present in cells of mast cell and basophil lineage from different individuals, but not in the other hematopoietic cells tested. The human β protein is homologous to rodent β. The consensus amino acid sequences for human, mouse and rat β show 69% identical residues.

It is a further aspect of the invention to provide polypeptides corresponding to the α, β, and γ subunits of FcεRI, more particularly to the human β subunit isolated from its natural environment. Isolated human β includes the amino acid sequences of the polypeptides either produced by recombinant methods, or synthesized by apparatus known to those of skill in the art, or isolated and purified by protein isolation and purification methods. The polypeptides of the present invention include the entire amino acid sequence, or selected portions thereof, for example, portions (domains) of the human beta subunit that are essential for (1) assembly of the receptor; (2) cell activation, and/or (3) complexing with the alpha and gamma subunits. "Natural environment" is defined to include the subunits in the cells in which they naturally occur, with other types of proteins and cellular components generally found in structural or functional association with the subunit.

The respective roles of the β and γ subunits of FcεRI in signal transduction, focusing on the recruitment of the two kinases, Lyn and Syk, known to be involved in FcεRI signaling, form an aspect of the present invention. The present invention reveals a relation between the structure of the human β subunit and its function as exemplified by an ARAM-containing cytoplasmic tail of the β subunit. The region is encoded by a segment of the gene encoding the β subunit.

Within the β encoding nucleotide sequence, an ARAM has been identified and characterized. Previous studies had shown that the signal motif present in γ (ARAM-γ) was sufficient, when expressed by itself, for display of full signalling capacity, relative to the multimeric receptor. This also had been shown for other ARAMs, such as those of the ζ and ε chains of the T-cell receptor. In these systems, presence of multiple ARAM's has ben related to signal amplification. It was expected, therefore, that the signal motif of β, ARAM-β, likewise would be sufficient for the display of full signaling capacity. The situation proved more complex, however, and each of ARAM-β and ARAM-γ is now understood to control different signals.

A protein sequence motif (ARAM), present in some members of the antigen receptor family to which FcεRI belongs, is able, when expressed by itself, to elicit the full range of activation signals observed with the complete receptors. In FcεRI this has been shown in particular for the motif of the γ chain ARAM-γ. However, FcεRI possesses another copy of ARAM in the β chain.

From the many studies on the functional capacity of ARAMs of other systems, one would have predicted that ARAM-β would exhibit the same range of activities as ARAM-γ, and that the purpose of a second ARAM in FcεRI would be to amplify signalling, as is the case in the T-cell receptor (Irving et al., 1993). Yet this is not the case for β of FcεRI. Surprisingly, ARAM-β is unable to mediate serotonin release, while ARAM-γ can. Also, ARAM-β mediates a barely detectable calcium flux, whereas ARAM-γ mediates one comparable to that of the full receptor. The ARAM-containing tail of β binds the tyrosine kinase Lyn, but the ARAM-containing tail of γ cannot. The ARAM-containing tail of γ activates the tyrosine kinase syk, even though the ARAM-containing tail of β cannot. Based on what is known about ARAMs in other receptors, these results suggest a new model for the signalling strategy of FcεRI which could apply to other multimeric antigen receptors as well; that is, a model where the signalling subunits β and γ cooperate in a time-dependant manner to produce the full signalling array of the receptor. This implies cooperative recruitment of specific kinases by the various signalling chains.

Another unpredictable aspect of the ARAM-β is that it may not be solely responsible for Lyn binding. Previous studies had shown that the whole signalling capacity of ARAM-containing receptors could be attributed to ARAM. This is not the case for β, where a sequence other than ARAM-β in the C-terminal tail of β is likely to be responsible for the binding of the tyrosine kinase Lyn. This is based on the fact that there is some binding of Lyn to FcεRI even when the tyrosine residues in the β ARAM are mutated.

Many studies have demonstrated that the interaction between receptors and tyrosine kinases of the src family, to which Lyn belongs, takes place between phosphorylated tyrosine residues of the receptors and the SH2 domain(s) of the kinases. This action has even been visualized via X-ray crystallography. Therefore, based on the present finding that β binds Lyn, an interaction identical to what had been previously reported between predicted receptors and src-family kinases would be expected. Unexpectedly, it has been shown that the binding of Lyn to β does not require the phosphorylation of the tyrosine residues of β, because it takes place with resting β, the tyrosine residues of which are not phosphorylated. Furthermore, Lyn-binding possibly does not even require the presence of the tyrosine residues of β, because their removal by point mutation still permits binding of Lyn to β.

The complex picture of the signalling machinery of FcεRI has been elucidated, in accordance with the present invention, through the following technical approach:

1. A dual strategy was pursued which combined studies of the full receptor, either wild type or with the tyrosine residues of β mutated, with studies of chimeric molecules that harbored either the ARAM-containing tail of β or the ARAM-containing tail of γ, all expressed by transfection. This dual strategy revealed the effects of both the presence and the absence of a particular residue or sequence of residues. The strategy also avoided artifactual phenomena and, hence, reinforced the value of the results.
2. Because results of some experiments required a particularly sensitive approach, for example, to determine that the β chimera was able to produce a calcium flux, even if it was a weak one, many different negative controls were developed.
3. Similarly, visualizing the association of Lyn with β would not have been possible with the protocols described in most papers addressing comparable questions of association of molecules with kinases. Visualization required a four-step procedure. First, the receptor complexes from the cell surface were precipitated with an anti-IgE antibody coupled to beads. Second, an in vitro kinase assay was performed on the precipitated complexes, thereby labelling the receptor-associated kinases through autophosphorylation. Third, the precipitated complexes were eluted from the beads. Fourth, the Lyn molecules associated with the surface receptors were specifically reprecipitated with an anti-Lyn antibody.

It is another aspect of the invention to provide a recombinant DNA molecule comprising a vector and a DNA segment encoding the α, β, or γ subunits of FcεRI.

It is a further aspect of the invention to provide a cell that contains the above-described recombinant DNA molecule.

It is another object of the invention to provide a method of producing polypeptides having amino acid sequences corresponding to the α, β, and γ subunits of FcεRI, both in rodent and human species.

Analysis of the surface expression of transfected receptors in fibroblast-like cells indicates that human αγ and αβγ complexes are expressed with comparable efficiency. Unexpectedly, assembly rules were different in other human cells. In addition, human β interacts with human α slightly more efficiently than does rat β. By contrast, both rat and mouse β interact with their corresponding α chains much more efficiently than does human β, demonstrating a strong species specificity of the α-β interaction in rodents.

Transfection of human FcεRI α, β, γ cDNAs into RBL cells which spontaneously express rat FcεRI αβγ$_2$ tetrameric complexes at the surface was used to check, in a mast cell environment, the specificity of association between subunits from different species, in particular to check whether rat β could associate with human α. Surface expressed human α was precipitated after binding an anti-human α antibody. The precipitates were separated by electrophoresis and transferred to a membrane for Western blotting with an anti-human β antibody and with an anti-rat β antibody. This showed that human α expressed at the surface is associated only with human β and not rat β. This further confirms the results obtained in COS-7 and KU812 cells.

It is a further object of the invention to provide a method of producing a functional FcεRI receptor.

In one embodiment, the present invention relates to DNA segments that code for polypeptides having amino acid sequences corresponding to the α, β, and γ subunits of FcεRI.

Hybridization probes derived from these sequences can be used under stringent conditions to test for heterogeneity of nucleotide molecules encoding the β subunit protein in persons with allergic disorders. Atopic patients are screened in this manner to develop treatment strategies that are specific for the β protein encoded in these patients.

In another embodiment, the present invention relates to polypeptides having amino acid sequences corresponding to the α, β, and γ subunits of FcεRI.

In a further embodiment, the present invention relates to recombinant DNA molecules comprising a vector and a DNA segment that codes for a polypeptide having an amino acid sequence corresponding to the α, β or γ subunits of FcεRI.

In yet another embodiment, the present invention relates to a cell that contains the above-described recombinant DNA molecules.

In another embodiment, the present invention relates to a method of producing a functional FcεRI receptor comprising introducing into a host cell DNA segments encoding the α, β, and γ subunits of FcεRI; and effecting expression of said DNA segments under conditions such that said receptor is formed. Expression of the receptor on the surface of cells COS-7, CHO, T cells, K812 cells, P815 cells, and RBL cells is achieved by the present invention when the cDNA for all three subunits of FcεRI are simultaneously cotransfected. This success in expression of IgE binding permits detailed analysis of the IgE-receptor interaction and thus enables the development of therapeutically effective inhibitors.

The invention still further provides a method of producing the complete human FcεRI receptor, and for inhibiting formation of the receptor or its function, by inhibiting the β subunit.

An aspect of the invention is to stem the cascade of allergic responses resulting from aggregation of the high affinity receptor for IgE, by inhibiting the essential participation of the human beta subunit. That is, receptor interaction with Lyn is necessary for the phosphorylation of gamma. The beta subunit is the target to inhibit receptor aggregation and/or the function of the transduced signal. Such an inhibition has widespread applications for prevention and treatment of allergic diseases because the undesirable events cascading from the receptor-IgE interaction are allergen independent and arise from various cell types: mast cells, basophils, Langerhans cells and the like.

Inhibitors of beta include chemical preparations that attack the structure or function of the chain, anti-sense nucleic acid sequences, amino acid sequences capable of binding to the beta subunit polypeptide, and monoclonal antibodies directed to the subunit. In addition to inhibiting the beta subunit in general, assays are developed to inhibit binding of β subunit to Lyn.

Effective amounts of the inhibitors will be combined with a pharmaceutically acceptable carrier. Because of the variety of cell types in which the allergic response is related to the FcεRI, and because the reaction is allergen independent, route of administration may be either systemic or topical.

Candidate inhibitor substances are tested by methods disclosed herein. In vitro assays for inhibitor substances are provided through host cells transfected with nucleic acid sequences encoding the human alpha, beta and gamma subunits, complexed or incubated with inhibitors. Cell activation effected by the FcεRI receptor is triggered and compared in the presence versus absence of inhibitors. The inhibiting of β subunit binding to Lyn may be assayed. Inhibitors may be designed that are specific for β proteins that characterize certain classes of patients.

Further objects and advantages of the present invention will be clear from the description and examples below.

The following abbreviations are used in this description: FITC, fluorescein isothiocyanate; PAGE, polyacrylamide gel electrophoresis; DNP-HSA, dinitrophenyl - [30] - human serum albumin.

BRIEF DESCRIPTION OF THE DRAWINGS

FIGS. 2A, 2B, 2C, 2D, 2E, 2F, 2G, 2H, 2I, 2J, 2K, 2L, 2M, 2N,, 2O, 2P, 2Q. Nucleotide sequence (SEQ ID NO:2) of the human FcεRI β chain gene shown in continuing sections.

Figure 4A:
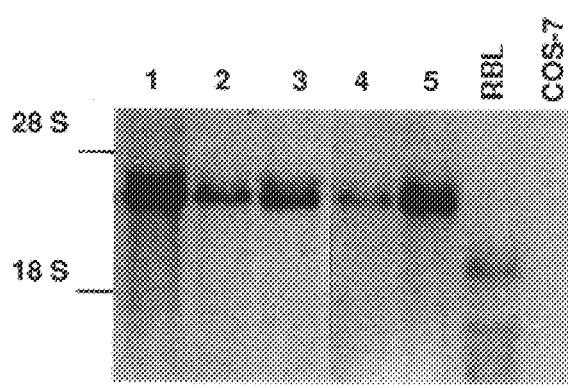
Figure 4B:
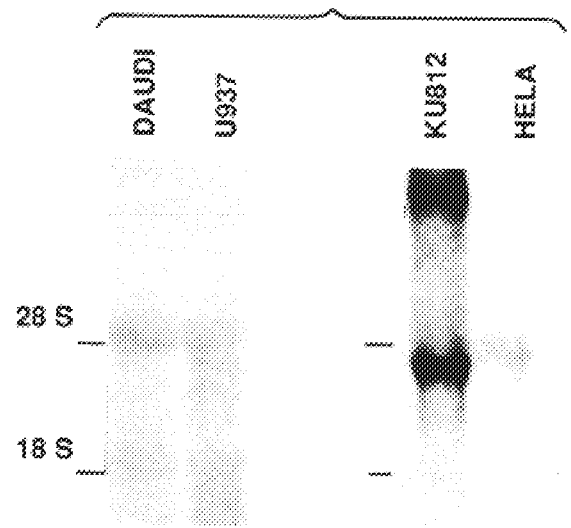
Figure 4C:
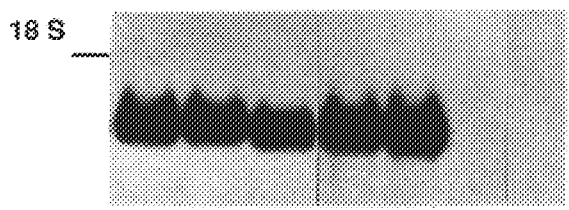

FIGS. 4A, 4B, 4C. Presence of transcripts in basophils are shown. Ten micrograms of total RNA from basophil enriched leukocytes and various other cells were fractionated on a denaturing agarose gel before being transferred to Nytran membranes and hybridized with human β cDNA probes (nucleotides +306 to +456 for Panel A (FIG. 4A) and nucleotides −2 to +790 in Panel C) (FIG. 4C). The membrane shown in Panel A was stripped and rehybridized with a full length human α cDNA probe (Panel B) (FIG. 4B).

Figure 5A:
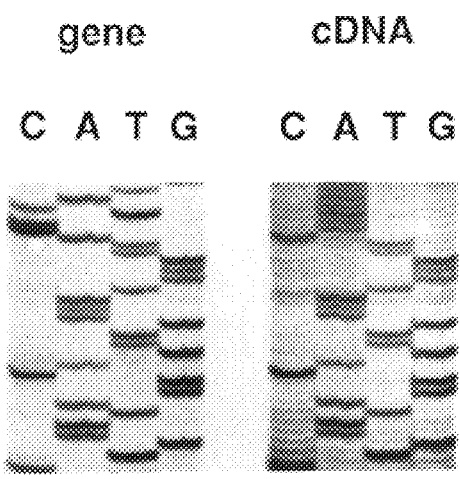
Figure 5B:
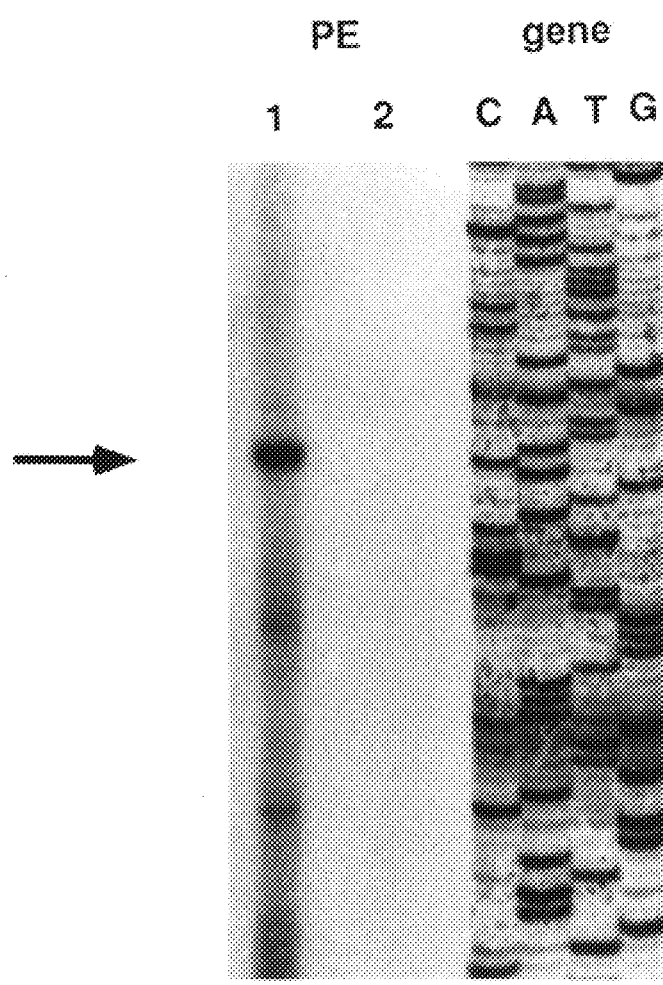

FIGS. 5A, 5B. Determination of the transcription initiation site of β.

FIG. 5A: RNA from basophils was reverse transcribed, poly A+ tailed at both ends with terminal transferase and amplified with PCR. The amplified product (cDNA) and the genomic DNA (gene) were sequenced with an identical primer and the respective sequencing reactions were run in parallel on a 8% acrylamide gel. The arrow marks the transcription start site. FIG. 5B: RNA from basophils (lane 1) or tRNA (lane 2) were used in the primer extension and the extended products analyzed on a 5% polyacrylamide urea gel in parallel with the sequencing reactions of the genomic DNA. The arrow marks the transcription start site.

Figure 6:
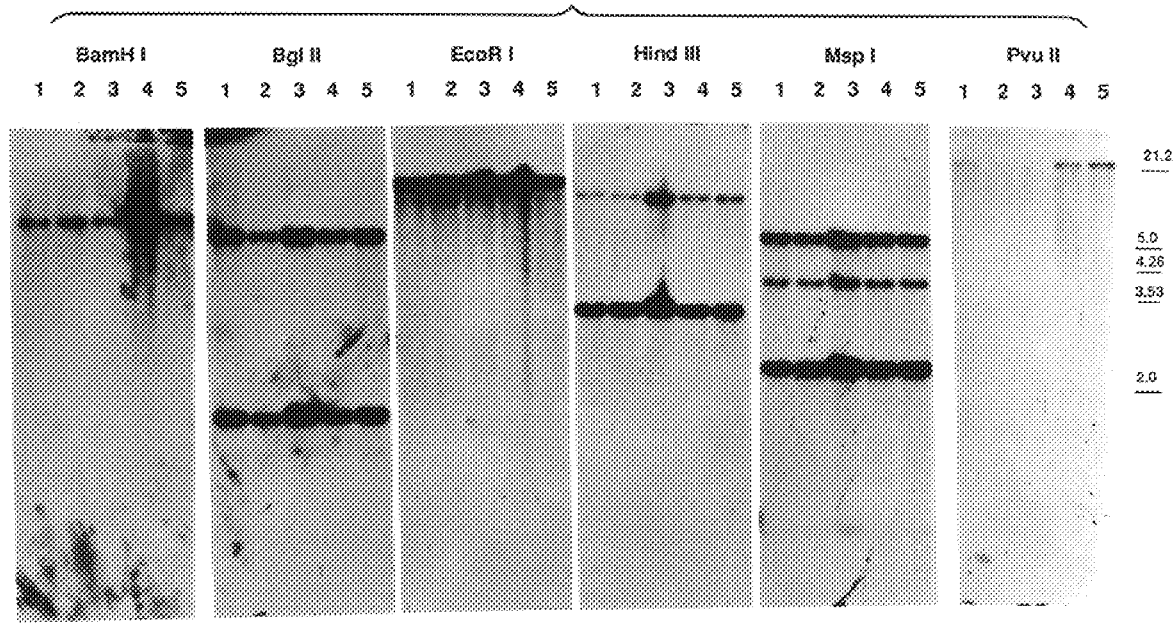

FIG. 6. Southern blot analysis of genomic DNA obtained from five different individuals. The DNAs were subjected to distinct restriction endonuclease digestions, blotted and hybridized with the human full length cDNA for the beta subunit. The numbers on the top indicate the different individuals while each panel corresponds to a different restriction digest. Size standards are indicated on the right.

FIGS. 7A, 7B. Amino acid sequence of the FcεRI human β subunit and alignment with rat and mouse β sequences (SEQ ID NOS:3–5, respectively). Identical and non-identical amino acid residues are indicated by capital and lower case letters respectively. The identities and closely related exchanges are marked ^ in the query line while the distantly related exchanges are denoted by a dot. Non-homologous exchanges show no marking in the query line. The gaps are indicated by a hyphen. The transmembrane domains are underlined and the splice sites indicated with vertical bars.

Figure 8:
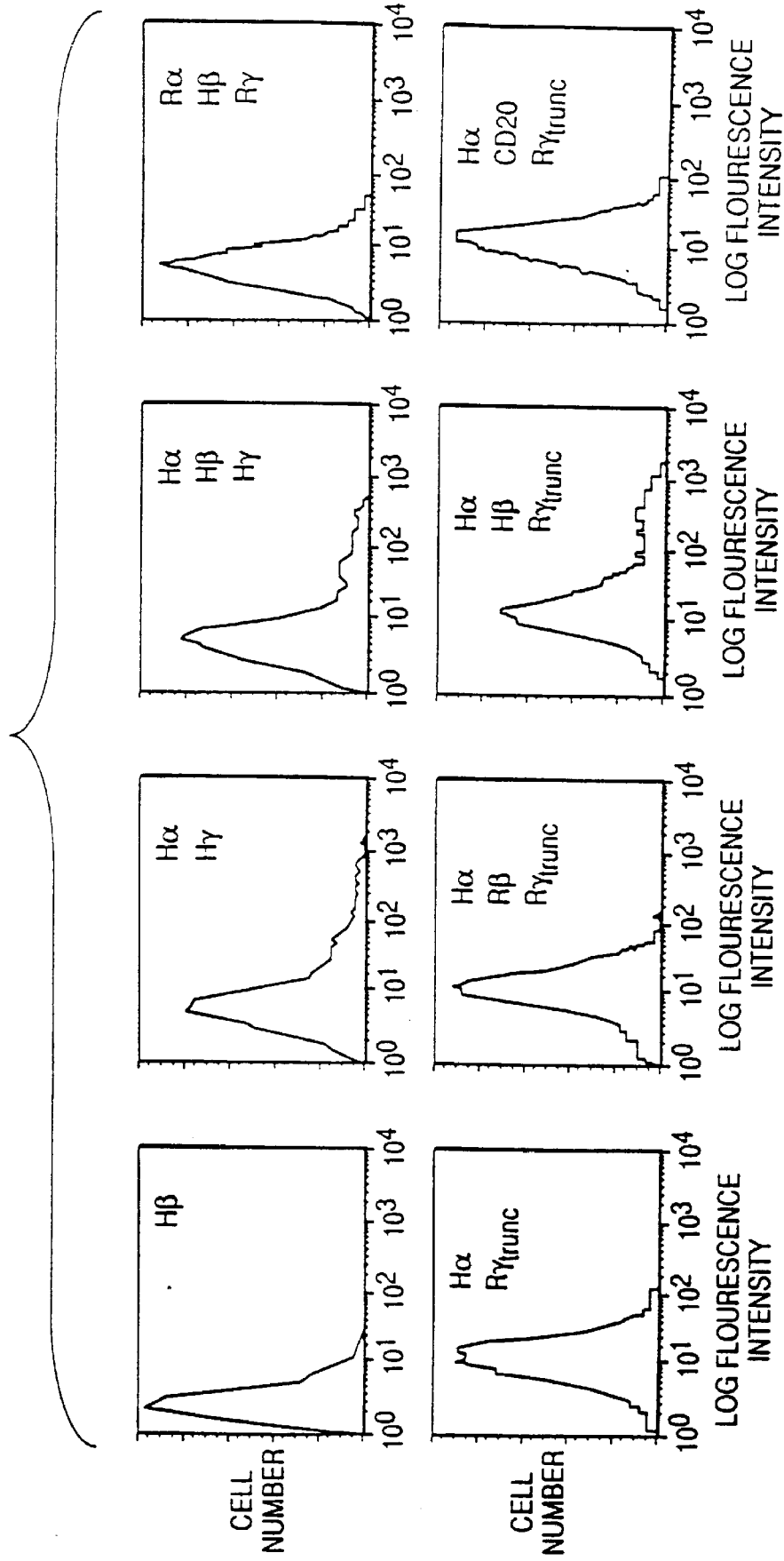

FIG. 8. Results of FACS analysis showing IgE binding in cells of a basophil line (KU812) transfected with various combinations of FcεRI subunits.

Figure 9:
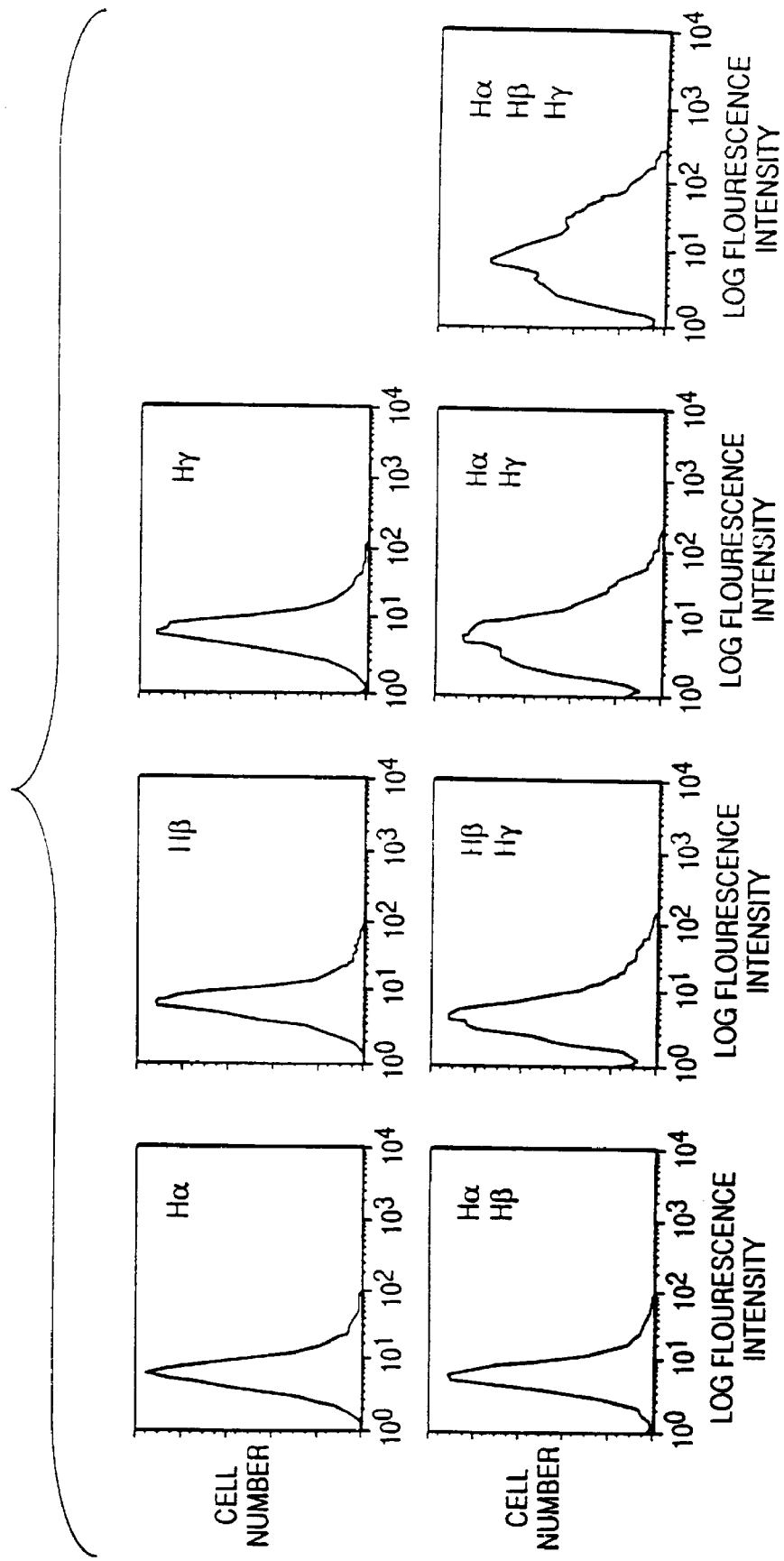

FIG. 9. Results of FACS analysis showing IgE binding in COS-7 cells transfected with various combinations of FcεRI subunits.

Figure 10A:
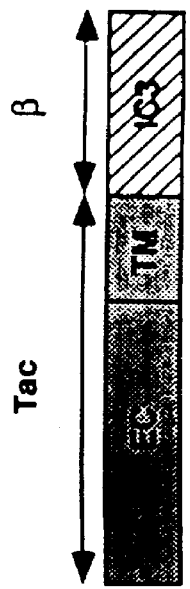
Figure 10B:
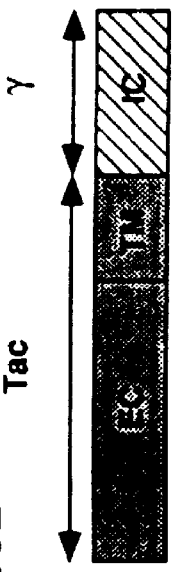

FIG. 10. Schematic representation of TTβ and TTγ chimeras and of wild type and mutated FcεRI β. A and B, in the TTβ and TTγ chimeras the extracellular (EC) and transmembrane (TM) parts from Tac are shaded, and the hatched parts are either the C-terminal intracellular part of β (IC3) or the intracellular part of γ (IC). C, the sequence of ARAM located in the C-terminal intracellular part of β (IC3) (amino acids 201–243 of Seq. I.D. No. 4) is indicated in bold, using the single-letter code for amino acids. The mutated tyrosines are indicated by their numbers in the complete sequence.

FIG. 11. Surface expression of transfected molecules A and B. Tac antigen expression on TTβ and TTγ chimera-transfected RBL cells. A, flow cytometry analysis: untransfected RBL (dotted line), RBL-TTβ (solid line), and RBL-TTγ (dashed line) were stained with FITC-labeled anti-Tac (B1.49.9). B, average antibody binding site numbers were calculated from saturation binding data of $^{125}$I-IgE and $^{125}$I-anti-Tac (7G7) on RBL-TTβ and RBL-TTγ. C, flow cytometry analysis of FcεRI expression on P815 cells transfected with FcεR1 α and γ along with either wild type of mutated β. Untransfected P815 (dotted line), P815-βWT (solid line), and P815-βY (dashed line) were stained with FITC-IgE.

FIG. 12. Calcium flux measurements. A, RBL-TTβ (dashed line) and RBL-TTγ (dotted line) saturated with biotinylated anti-Tac were loaded with fura-2 AM. Their capacity to respond to stimulation with avidin (30 μg/ml) or with anti-FcεRI α antibody (BC4, 0.5 μg/ml) was measured in a spectrofluorometer. Triton (0.1% final) and EGTA (18 mM final) were added for calibration (off scale). Calcium concentrations were calculated from photon counts using the published value of $2.24 \times 10^{-7}$ for the K for fura-2 at 37° C. The time axis for the trace for RBL-TTβ was shifted so that the two avidin triggerings would coincide. B, P815-βWT (solid line) and P815-βY (dashed line) loaded with fura-2 were triggered with anti-FcεRI α antibody (BC4, 0.5 μg/ml). Addition of thrombin was used as a positive control.

DETAILED DESCRIPTION OF PREFERRED EMBODIMENTS

The present invention relates in part to DNA sequences which code for polypeptides corresponding to the subunits of human FcεRI. More specifically, the present invention relates to DNA segments, for example, cDNA molecules, coding for polypeptides having amino acid sequences corresponding to the α,β and γ subunits of FcεRI. In one preferred embodiment, the DNA segments have the sequence shown in FIG. 2 (Seq. I.D. No. 2), allelic or species variation thereof, or a unique portion of such a sequence, where "unique portion" is defined here to mean at least 15–18 bases that are specific to a subunit. In another embodiment, the DNA segments encode the human amino acid sequence shown in FIG. 7 (Seq. I.D. No. 3), or allelic or species variations thereof, or a unique portion of such a sequence, "unique portion" in this context meaning a sequence of at least 5–6 amino acids that are specific for the subunit proteins.

A unique portion of the amino acid sequences of the human beta chain is an ARAM containing sequence. A specific ARAM may be derived from the amino acid sequences of FIG. 7, for example, the rat ARAM sequence is shown in FIG. 10 and in Seq. I.D. No. 1. The human ARAM sequence disclosed herein includes a region found to be critical in other ARAMs, but has an entire sequence that has not been reported for other ARAMs. For example, there are three tyrosine residues, not two as is usual, and unlike other ARAMs, mutation of even all three tyrosines, does not affect certain functions as described herein. In addition, the human ARAM has a third tyrosine between the two consensus tyrosines.

Allelic or species variations are defined as substitutions, deletions, or other alterations in the nucleotide or amino acid sequence that do not eliminate the function of the subunits as defined herein. For some uses, the nucleotide sequence may be deliberately altered to, e.g., test the effects of such alteration on the function of the beta subunit as is described herein where tyrosine is mutated, or to produce subunits which are inactivated for certain purposes.

Each of the two tyrosine kinases known to be involved in FcεRI signaling is controlled by a distinct motif-containing chain. Lyn associates with the nonactivated β chain, whereas γ promotes the activation of Syk. Neither the motif containing tail of β nor the motif containing tail of γ motif alone can account for the full signaling capacity of the entire receptor.

It is likely that, upon triggering the tetrameric receptor, Lyn already bound to β becomes activated and phosphorylates β and γ; the phosphorylation of γ induces the association of Syk with γ and the activation of Syk as well, resulting in the phosphorylation and activation of phospholipase C$\gamma_1$. Cooperative recruitment of specific kinases by the various signaling chains found in this family of antigen receptors could represent a way to achieve the full signaling capacity of the multimeric complexes.

Various studies indicate that isolated ARAMs activated cells in the same way as the multimeric receptors that include them. But the relationship between ARAMs and the various tyrosine kinases activated by these receptors is still debated. In addition, the question persists as to why these receptors should be such complex, multimeric structures if the action of an entire receptor can be mimicked by a short motif in a single subunit.

The signaling capacities of the ARAM-containing β and γ chains of FcεRI have been compared and their relationship with the two kinases Lyn and Syk has been analyzed. It was found that the ARAM-containing tails of β or γ cannot substitute for the entire receptor complex, and that they differ in their capacity to activate specific cellular functions, to wit:

(1) Engagement of a chimera containing the cytoplasmic tail of γ induces calcium flux and serotonin release; even under optimal conditions, however, these signals are weaker than those obtained from the tetrameric receptor under suboptimal conditions (see Table I and FIG. 12).

(2) Engagement of a chimera containing the C-terminal tail of β does not induce serotonin release. From the weakness of the calcium signal induced by β chimera engagement and from the fact that mutations in ARAM-β do not affect calcium flux in P815, it seems that β does not play an essential role in calcium mobilization (FIG. 12).

(3) Unlike tetrameric FcεRI, the β and γ chimeras mediate the phosphorylation of few substrates.

A potential mechanism for the different signaling patterns of β and γ is suggested by the observation that the two chains control different kinases. Lyn binds to the β chimera, as shown by reprecipitating the kinase from anti-chimera immune complexes. Syk is phosphorylated and activated through the γ chimera. Because of the critical role of early phosphorylation events in the signaling pathway of FcεRI, this represents a significant difference between β and γ and demonstrates further the specificity of the relationship between β and Lyn and between γ and Syk.

In another embodiment, the present invention relates to a recombinant DNA molecule comprising a vector, for example, a plasmid or viral vector, and a DNA segment coding for a polypeptide corresponding to the α,β or γ subunit of FcεRI, as described above, or to the ARAM-containing tail of β. In a preferred embodiment, the encoding segment is present in the vector operably linked to a promoter.

In a further embodiment, the present invention relates to a cell containing the above described recombinant DNA molecule. Suitable host cells include procaryotes, such as bacteria, including *E. coli,* and both yeast and higher eucaryotes, including mammalian cells. Introduction of the recombinant molecule into the host cell can be effected using methods known in the art.

In another embodiment, the present invention relates to a method of producing the above described polypeptides, comprising culturing the above described host cells under conditions such that said polypeptide is produced, and isolating said polypeptide.

In a further embodiment, the present invention relates to a method of producing a functional FcεRI receptor comprising introducing into a host cell DNA segments encoding the α,β and γ subunits of FcεRI and effecting expression of said segments under conditions such that said receptor is formed.

The nucleic acid sequences and polypeptides according to this invention exhibit a number of utilities including but not limited to:

1. Utilizing the polypeptide or a fragment thereof as an antagonist to prevent allergic response, or as a reagent in a drug screening assay.
2. Utilizing the polypeptide as a therapeutic agent.
3. Utilizing the polypeptide for monitoring IgE levels in patients.
4. Utilizing the nucleic acid sequence to synthesize polypeptides which will be used for the above purposes.
5. Utilizing the nucleic acid sequences to synthesize cDNA sequences to construct DNA useful in diagnostic assays.

The present invention will be illustrated in further detail in the following examples. These examples are included for illustrative purposes and should not be considered to limit the present invention.

EXAMPLE 1

The Beta Subunit of FcεR Is Necessary for Expression in Mast Cells

FIGS. 8 and 9 present the results obtained from FACS analysis (IgE binding) of cells transfected with the human alpha and gamma encoding nucleotide sequences.

FIG. 8: represents KU812 cells (a basophil line).

FIG. 9: represents COS-7 transfected cells.

The clone of Ku812 cells used does express the mRNA for the three subunits alpha, beta and gamma but the receptor is not naturally expressed on the surface.

In FIG. 9, the transfection of human alpha and gamma in COS-7 cells is confirmed to be sufficient for expression of the alpha-gamma complex on the surface of the transfectants. These results also show that human beta and not rat beta associates efficiently with human alpha and that therefore, rat beta cannot replace human beta.

FIG. 8 illustrates that transfection of alpha-gamma in KU812 results in very little expression of receptors. The level of expression is similar to the level obtained after transfection of beta and gamma. Therefore this level may be attributable to the endogenous alpha (for beta and gamma transfection) or to the endogenous beta (for alpha and gamma transfection). By contrast the level of expression after co-transfection of the three cDNAs is very substantial.

From these results, it may be concluded that:

1. in mast cells and basophils, regulation of the level of expression of the receptor may be different than in fibroblasts.
2. in human mast cells and basophils, receptor expression requires the presence of alpha, beta and gamma; whereas in transfected fibroblasts, human alpha and gamma are sufficient.

EXAMPLE 2

Isolation, Mapping and Sequencing of the Human FcεRI β Gene

Initial attempts to isolate human β cDNA clones were by screening a human mast cell cDNA library with full-length rat and mouse cDNA probes. These probes were radiolabelled and used to screen 7×10⁵ colonies. Four clones were isolated, all of which contained a 153 bp insert with 73% homology to rat β cDNA. The sequence of this insert corresponded to a portion of β which includes the intracellular loop and the third transmembrane domain. These four identical clones are the likely result of library amplification of a single clone generated by recombinations. Two additional libraries were screened: another mast cell cDNA library and a cDNA library derived from basophil-enriched leukocytes. The latter library was also used to isolate human γ cDNA clones. A total of 10⁷ independent cDNA clones were screened with a panel of murine probes and oligonucleotides and with the 153 bp human β probe. However no additional clones were isolated.

6×10⁵ independent genomic clones from a human genomic leukocyte library were subsequently screened with the radiolabelled 153 bp human probe and 10 clones with an average size insert of 25 kb were isolated. These clones all hybridized with two 20 mer-oligonucleotide probes corresponding to the beginning and the end of the rat β coding sequence. Four different restriction patterns could be generated from the 10 clones. However, southern blots with various oligonucleotide probes scanning different regions of the rat β coding sequence indicated that the four restricted patterns were not the product of different genes. Rather the clones showed differences in the lengths of the sequences flanking the β gene.

Figure 1:
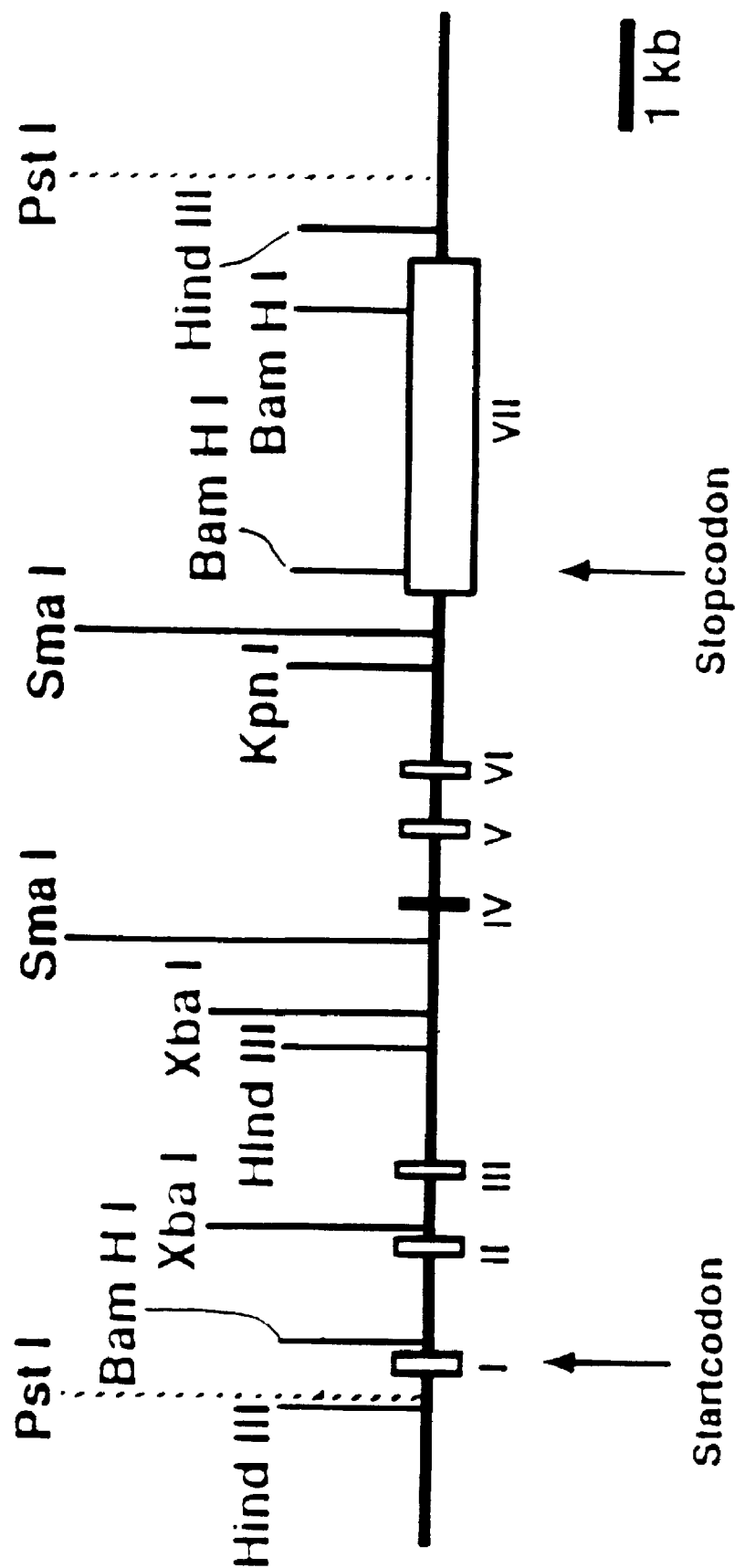
FIG. 1. Restriction map structure of the human β gene and exon-intron are shown. The positions of the 7 exons are depicted by boxes. The location of the start and stop codon is indicated.

One clone containing a 25 kb insert was chosen for further characterization mapping and sequencing. A restriction map shown in FIG. 1 was constructed by complete and incomplete digestion with the restriction endonucleases Hind III, Pst I, BamH I, Xba I, Sma I and Kpn I. A 3.2 kb Hind III fragment was found to hybridize with oligonucleotide probes corresponding to the start codon, and transmembrane regions I and II of rat β. A 2.8 kb Sma I fragment hybridized with rat β probes of transmembrane domains III and IV and a 4.5 kb Sma I fragment with probes of the stop codon region. The 3 fragments were subcloned into pGEM 3zf (+) or (−) and sequenced in full (FIG. 2 and Seq. I.D. No.2). The fragment corresponding to the 0.9 kb gap between the Hind III and 2.8 kb Sma I fragments was produced by PCR and sequenced. Analysis using PCR confirmed that the two Sma I fragments were adjacent to each other.

By comparing the sequences of the human β gene and the rat β cDNA (FIG. 3) seven homologous regions which were likely localized to correspond to seven different exons.

EXAMPLE 3

Synthesis of Human β cDNA Coding Sequence

In order to confirm the sequence of the exons and to define the intron-exon borders, human β cDNA was synthesized by reverse transcription of RNA purified from basophil-enriched leukocytes followed by an amplification of the reverse transcripts using the polymerase chain reaction (PCR) (described in Materials and Methods herein). This applied product extended from 2 nucleotides preceding the start codon to 32 nucleotides following the stop codon. The cDNA sequence was found to be identical to the corresponding sequence of the human β gene. This confirmed that the coding sequence of human β is contained in seven exons. Furthermore, the comparison of cDNA and gene sequences and the detection of consensus sequences for intron-exon borders in the human β gene allow for a precise determination of these borders. The 5' borders of the six intervening introns invariably start with GT and the 3' borders end with AG.

EXAMPLE 4

Analysis of Human β Transcripts

To evaluate the length of 5' and 3' untranslated sequences, the size of human β transcripts was analyzed. RNA from basophil-enriched leukocytes obtained from different individuals were hybridized by northern blotting with the radiolabelled 153 bp human β probe (FIG. 4A) Two transcripts around 3.9 kb were found in human basophils but not in COS-7 cells. The human transcripts are substantially longer than their rodent counterparts (2.7 and 1.75 kb) (Ra, 1989; Kinet, 1988) as detected in RBL cells by crosshybridization. This longer size may explain initial failures to isolate human β cDNAs from the three oligo-dT primed libraries. Similar results were obtained with a full-length cDNA probe of human β. Hybridization of the same RNAs with a human α cDNA probe revealed transcripts for α of the expected size (1.1 kb) (FIG. 4B). RNA from different cell lines were also hybridized with a full length human β cDNA probe (FIG. 4C). The message for human β is only detected in the basophil line KU812 but not in U937, Daudi and Hela cells. An additional band is seen in KU812 which could correspond to unspliced transcripts.

Figure 3:
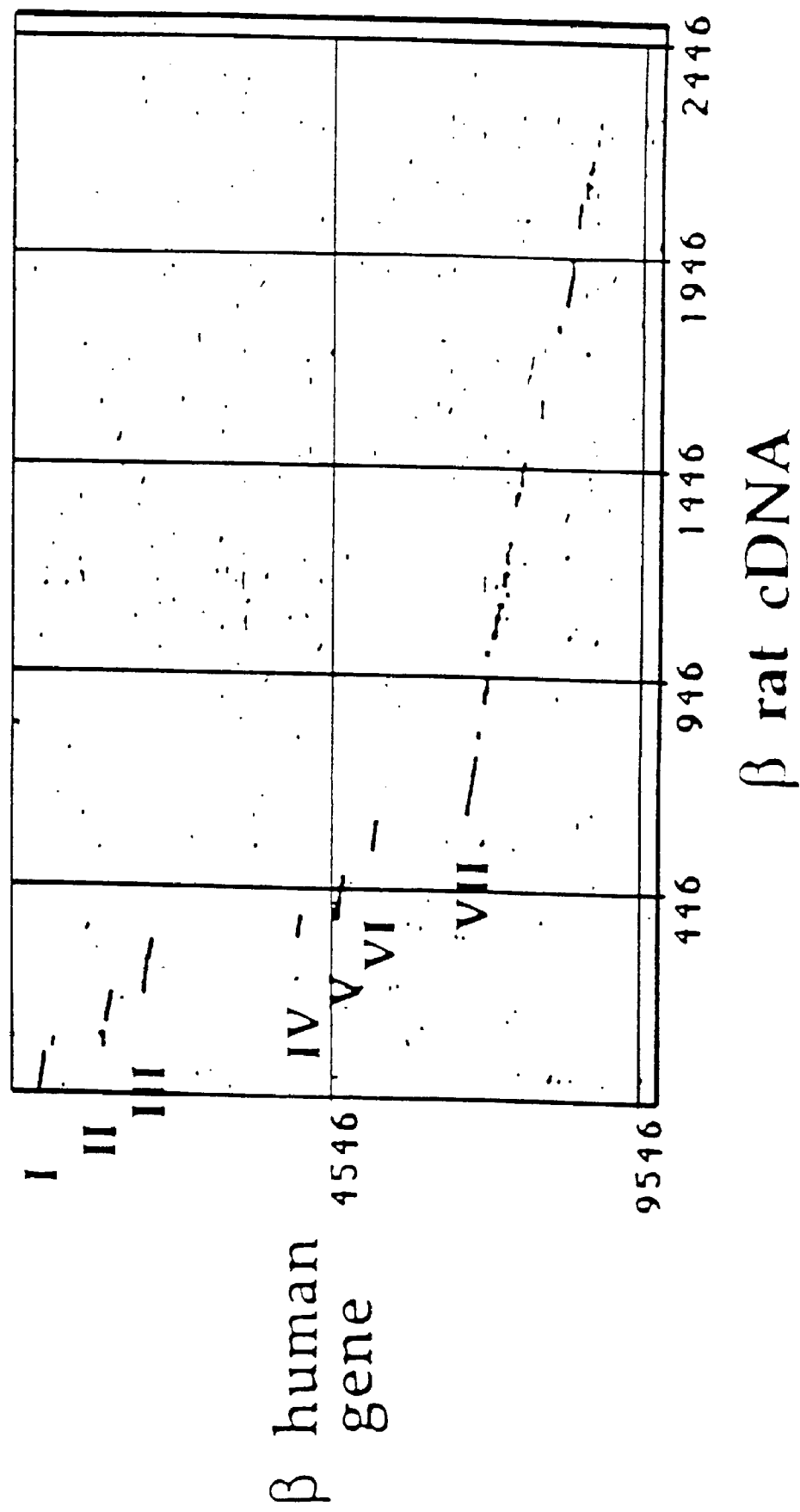
FIG. 3. Comparison of the human β gene and rat β cDNA sequences by a dot matrix blot. The Pustell DNA Matrix of the Macvector program was used with a window of 30 nucleotides and a minimum score of 63%. The Roman numerals indicated on the left correspond to the seven exons.

With an open reading frame of 732 bp and assuming 200 bp for the poly A tail, human β transcripts should contain about 3 kb of untranslated sequences. FIG. 3 shows that most of the untranslated sequences are in the seventh exon. The possibility that additional exons of 3' or 5' untranslated sequences had not yet been identified was also explored.

EXAMPLE 5

A. Characterization of the (A) 5' End and of the Transcription Initiation Site

The transcription start site was determined by sequencing directly a PCR amplified product of the reverse transcribed RNA as described in "Materials and Methods" herein. RNA from basophil-enriched leukocytes was reverse transcribed from a primer of the human β coding sequence. Poly-A tails were added to the reverse transcripts by treatment with terminal transferase and the resulting cDNAs were amplified by PCR. Single stranded DNAs (positive strands poly dT tailed) were then produced by asymmetric PCR and directly sequenced. The cDNA sequence of the negative strand corresponding to the 5' end of the RNA is shown in FIG. 5A and is compared to the relevant sequence of the β gene. The perfect match between the two sequences ends after GGGTT. Then the cDNA sequence reproducibly shows a C, which is not present in the gene, followed by the expected poly-A tail. This additional C may correspond to the G of the cap structure and indicate the location of the start site.

Experiments of 5' extension (FIG. 5B) confirmed that there is a major start site in this area (about 11 nucleotides 3' of the position described above). It is difficult, though, to exclude the possibility that the faint bands seen below and above the major start sites correspond to minor start sits. However the presence of a TATAAA box found in the 5' sequence supports the existence of a unique start site. In addition the location of the TATAAA box (usually 25 nucleotides 5' of the start site) is more consistent with the precise localization of the start site as shown. Indeed the TATAAA box is located between nucleotides 29 and 24 upstream of this start site as shown in FIG. 5A. Taken together the data indicate that the human β mRNA start with the sequence AACCC (see FIG. 2 and FIG. 5A) and has 102 bp of 5' untranslated sequence.

B. Characterization of the 3' end

A comparison between the rat β cDNA and human β gene sequence (Seq. I.D. No. 2) as shown in FIG. 3 reveals that the seventh exon of the β gene extends at least from nucleotides 7228 to at least nucleotide 9365. But an additional 3' untranslated sequence (about 800 bp) had to be found to fully account for the 3.9 kb transcripts. To analyze whether the missing sequence was part of the seventh exon or of other undetected exons, three probes from the β gene were prepared to test their reactivity with β transcripts. These transcripts hybridized in northern blots with both the NsiI-BamH1 fragment (nucleotides 8915–9705 of Seq. I.D. No. 2) and the BamHI-SphI fragment (nucleotides 9705–10169 of Seq. I.D. No. 2) but not with the fragment 3' of the SphI site. Interestingly two polyadenylation signals AATAAA are found at nucleotides 10118 and 10213 of Seq. I.D. No. 2). Therefore this region is likely to correspond to the end of exon 7. It is likely that both polyadenylation signals could be used to create the apparent doublet of transcripts around 3.9 kb (see FIG. 4).

EXAMPLE 6

Organization of the Human β Gene

Taken together the data presented herein indicate that the human β gene contains seven exons and six introns and spans about 10 kb. Exon 1 codes for 102 bp of 5' untranslated sequence and the first 18 amino acid residues of the N-terminal cytoplasmic tail. Exon 2 encodes the remaining of the cytoplasmic tail and the first three residue of TM1. Exon 3 codes for the remaining of TM1, the first extracellular loop and the first half of TM2. Exon 4 encodes the second half of TM2 and a portion of the cytoplasmic loop. Exon 5 codes for the last three residue of the cytoplasmic loop, TM3 and most of the second extracellular loop. Exon 6 codes for the last two residues of the extracellular loop, TM4 and the first quarter of the C-terminal cytoplasmic tail. Finally, exon 7 codes for the remaining of the cytoplasmic tail and the long untranslated 3' sequence.

Digestion of genomic DNA from five different individuals with BamH I, Bgl II, Eco RI, Hind III, Msp I and Pvu II and hybridization of these digests with a human cDNA probe (from start to stop codon) supports the existence of a unique gene (FIG. 6). In addition the lengths of the restriction fragments detected on the southern blot are entirely consistent with the lengths predicted from the sequence of the gene as depicted in Seq. I.D. No. 2. Three BamHI sites (at nucleotides 611, 7363 and 9705 of Seq. I.D. No. 2) are present in the gene. As expected only one fragment (611–9705) is seen is seen on FIG. 6 because the other fragments should not hybridize with the cDNA probe. The two predicted Bgl II fragments (799 to 2221 and 2221 to 7874) and the two predicted Hind III fragments (0 to 3179 and 3179 to 100497) are readily detected. The results obtained after EcoRI and PvuII digestions are consistent with the fact that none of these sites are found in the sequence of the gene. Finally the pattern observed after Msp I digestion is also consistent with predicted fragments of 2067 bp, 3870 bp and a larger 5' fragment extending from nucleotide 3622 to an undetermined Msp I site upstream of the gene.

EXAMPLE 7

The Human β Protein

The human β protein comprises 244 amino-acid (aa) residues and has a molecular mass of 26,532 daltons (FIG. 7; Seq. I.D. No. 3). Similar to rat (243 aa) and mouse β (236 aa), human β contains four hydrophobic segment suggestive of transmembrane domains (TM) but no leader peptide. FIG. 7 shows an alignment of the human sequence with the rat and mouse sequence. The consensus sequence for β (not shown) from the three species (rat, mouse and human) shows that 91.4% of the amino-acid residues are homologous while 68.7% are identical.

EXAMPLE 8

Transfection in COS-7 Cells: Expression of Human and Hybrid FcεRI Receptors

TABLE I

Functional expression of FcεRI after transfection of various subunit combinations

| Transfected cDNAs | | | Fluorescent cells (FACS)[a] | |
|---|---|---|---|---|
| | | | n | Mean ± S.D. % |
| Human α | — | — | 1 | 0.2 |
| Human α | human β | — | 1 | 0.2 |
| Human α | — | human γ | 7 | 10.4 ± 8.7 |
| Human α | human β | human γ | 7 | 8.3 ± 5.0 |
| Human α | rat β | human γ | 4 | 5.4 ± 3.4 |
| Rat α | rat β | rat γ | 8 | 18.0 ± 17.8 |
| Rat α | human β | rat γ | 10 | 2.4 ± 2.0 |
| Rat α | human β | human γ | 5 | 1.8 ± 1.3 |
| Mouse α | mouse β | mouse γ | 4 | 8.2 ± 5.6 |
| Mouse α | human β | mouse γ | 6 | 1.6 ± 1.2 |
| Mouse α | human β | human γ | 2 | 1.5 ± 0.8 |
| Human α | — | rat$\gamma_{trunc}$ | 7 | 1.4 ± 1.0 |
| Human α | rat β | rat$\gamma_{trunc}$ | 5 | 3.2 ± 2.8 |
| Human α | human β | rat$\gamma_{trunc}$ | 7 | 7.4 ± 7.9 |
| Rat α | rat β | rat$\gamma_{trunc}$ | 2 | 9.3 ± 0.8 |
| Rat α | human β | rat$\gamma_{trunc}$ | 2 | 0.4 ± 0.5 |

[a]FACS, fluorescence-activated cell sorting; trunc, truncated.

It was found that co-transfection of α, β, and γ cDNAs is necessary to promote expression of rat or mouse FcεRI on the surface of transfected COS-7 cells. By contrast, co-transfection of human α and β cDNAs results in the surface expression of αγ complexes without apparent need for β. With the availability of human γ cDNAs, the question was explored whether human β would influence in any way the efficiency of surface expression of the human receptor complex. Table 5 shows that co-transfection of human α and γ cDNAs into COS-7 cells results in 10.4%±8.7 of the cells being fluorescent when analyzed by FACS after binding of fluoresceinated IgE. This level of expression is not significantly modified when human β cDNA is co-transfected with human α and γ cDNAs (8.3%±5.0). Thus, human β does not seem to influence the level of surface expression of human FcεRI in transfected COS-7 cells. Substituting rat β or human β reduces the level of expression (5.4%±3.4).

The effect of substituting human β for rat β was analyzed. Co-transfection of rat α, β, γ cDNAs result in much higher level of expression (18.0%±17.8) than co-transfection of rat α, γ with human γ (2.5%±2.0) (Student's t statistic=2.75; $p \leq 0.014$). Similarly co-transfection of mouse α, β, γ cDNAs is more efficient (8.2%±5.6) than co-transfection of mouse α, γ with human β (1.6%±1.2) (Student's t statistic:2.91; $p \leq 0.019$). Because replacing rat γ or mouse γ with human γ does not restore expression (compare 2.4% with 1.8%, and 1.6% with 1.5%), it is likely that the problem of expression resides in the human β-rat α or human β-mouse α interaction.

It is known that truncation of the cytoplasmic tail of rat γ prevents the surface expression of human α in transfectants (Varin-Blank, 1990). The question was whether human β could complement the surface expression of human α in these conditions. It was confirmed that co-transfection of human α with truncated rat γ permit only very poor surface expression of αγ complexes (1.4%±1.0). When human β is co-transfected with the latter combination there is an increase of expression (7.4%±7.3, n=7). However this increase does become significant (p≦0.035) when one aberrant point is not included in the seven experiments. The same increase is not observed when rat β is substituted for human β (3.2%±2.8) suggesting again that there may be specific points of interaction between human α and β. In other experiments using the truncated rat γ, it was found that human β cannot be substituted for rat β in its interaction with rat α (compare 9.3%±0.6 with 0.4%±0.4; (t=13.0; p≦0.006).

Taken together these data indicate that there is a tendency for human β to interact more efficiently with human α than does rat β, but the species specificity is weak. By contrast, there is a strong species specificity in the interaction between rat β and rat α or between mouse β and mouse α.

Human αγ complexes may be expressed on the surface of transfected cells. Moreover co-transfection of human α and γ with rat β results only 20% of the receptors being αβγ complexes, the remaining 80% being αγ complexes. Therefore, it is theoretically possible that αγ complexes occur naturally. However in view of the species specificity of interaction between human β and α (see above), previous results obtained from the co-transfection of human α and γ with rat β suggest the in vivo situation could be different.

These genetic results, of course, provide much more than an assay, as important as the latter may be. Through directed mutation they will, in addition, allow the development of further information regarding the critical binding regions. It is expected that, using this information, rational drug design will become possible. It is further expected that it will be possible to block the function of the receptor itself, i.e., it will be possible to interfere with the early biochemical signals that result from activation of the receptor.

EXAMPLE 9

Analysis of the ARAM-containing Cytoplasmic Tail of the Human β Subunit

Generation of Transfectants

A β chimera (TTβ) analogous (Letourneur et al., 1991) to the γ chimera (TTγ) described previously (Letourneur and Klausner, 1991) was constructed. TTβ and TTγ contain the extracellular and transmembrane segments of the human IL-2 receptor α chain (Tac) fused to the C-terminal cytoplasmic part of rat FCεRI β or the cytoplasmic tail of rat FcεRI γ, respectively (FIG. 10, A and B). By virtue of the Tac transmembrane segment, the chimeric molecule TTβ or TTγ are expressed on the cell surface as single chain molecules. TTβ or TTγ was transfected into RBL-2H3, an FcεRI-positive rat mast cell line. RBL-TTβ clones and RBL-TTγ clones stably expressing TTβ or TTγ, respectively, were isolated. In addition, another clone of RBL-TTγ was obtained from F. Letourneur.

Figure 10C:
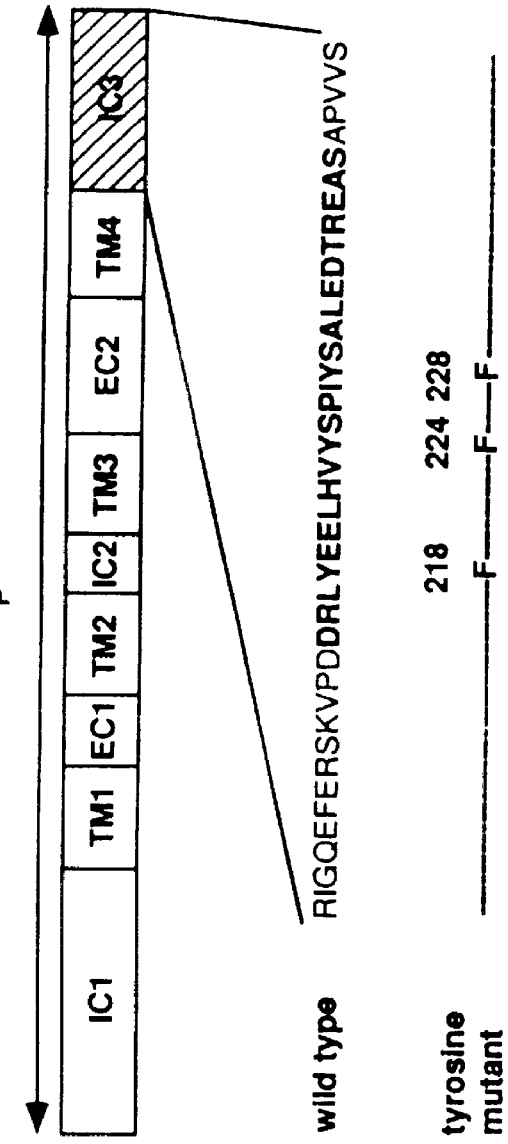

A mutated form of full length rat FcεRI β was generated by substituting 3 tyrosine residues with phenylalanines at positions 218, 224, and 228 within ARAM β (FIG. 10C; Seq. I.D. No. 4). The cDNAs coding for rat α and γ were cotransfected into an FCεRI-negative mouse mast cell line, P815, with either the wild type or tyrosine-mutated β cDNA, to generate P815-βWT and P815-βY, respectively.

Expression of the transfected molecules on RBL and P815 was assessed by flow cytometry. Staining with FITC-labeled anti-Tac antibody reveals expression of Tac chimeras on RBL-TTβ and RBL-TTγ, but not on untransfected RBL (FIG. 11A). The number of chimeric molecules and endogenous FcεRI receptors on the surface of these cells was quantitated by saturation binding of $^{123}$I-antibodies (IgE and anti-Tac 7G7) (FIG. 11B). In comparison with RBL-TTγ, RBL-TTβ clones express approximately half as many anti-Tac reactive molecules at their surface. However, the number of chimeric molecules on these clones is either comparable with, or twice as high as, that of FcεRI, depending on the stoichiometry of binding of 7G7 to Tac. Staining of P815 transfectants with FITC-labeled mouse IgE shows that both P815-βWT and P815-βY bind IgE and therefore express FcεRI, whereas untransfected P815 do not (FIG. 11C).

In Contrast to ARAM-γ, ARAM-β Does Not Mediate a Late Signal, Serotonin Release

To study the coupling of ARAM-β to cellular activation mechanisms, the ability of the β chimera to initiate degranulation, a late event in mast cell activation, was tested. As reported previously, the γ chimera is able to induce degranulation as assessed by serotonin release from RBL cells. RBL-TTβ and RBL-TTγ cells (1×10$^6$ cells/ml) were incubated with biotinylated anti-Tac antibody B1.49.9 (2.5 μg/ml) or anti-dinitrophenyl IgE, either at a saturating concentration (1 μg/ml) or at ⅕ saturation (0.15 μg/ml). They were stimulated by cross-linking either anti-Tac with avidin (15 μg/ml) or IgE with the multivalent antigen dinitrophenyl-[30]-human serum albumin (DNP-HSA) (100 ng/ml). Stimulation through the chimera does not cause serotonin release from RBL-TTβ, although the cells respond to cross-linking of endogenous FcεRI even at suboptimal loading of IgE (Table II). Stimulation of the γ chimera on RBL-TTγ leads to serotonin release, but as reported previously, less than that mediated by FcεRI. Three more clones of RBL-TTβ were tested, higher concentrations of avidin (30 and 45 μg/ml), two other anti-Tac antibodies (7G7 and HD245), and two cross-linking antibodies (1–100 μg/ml), with the same type of results. It appears that neither ARAM-β nor ARAM-γ can fully replace the tetrameric receptor and that they differ from each other in their ability to generate a late signal such as serotonin release.

Figure 12A:
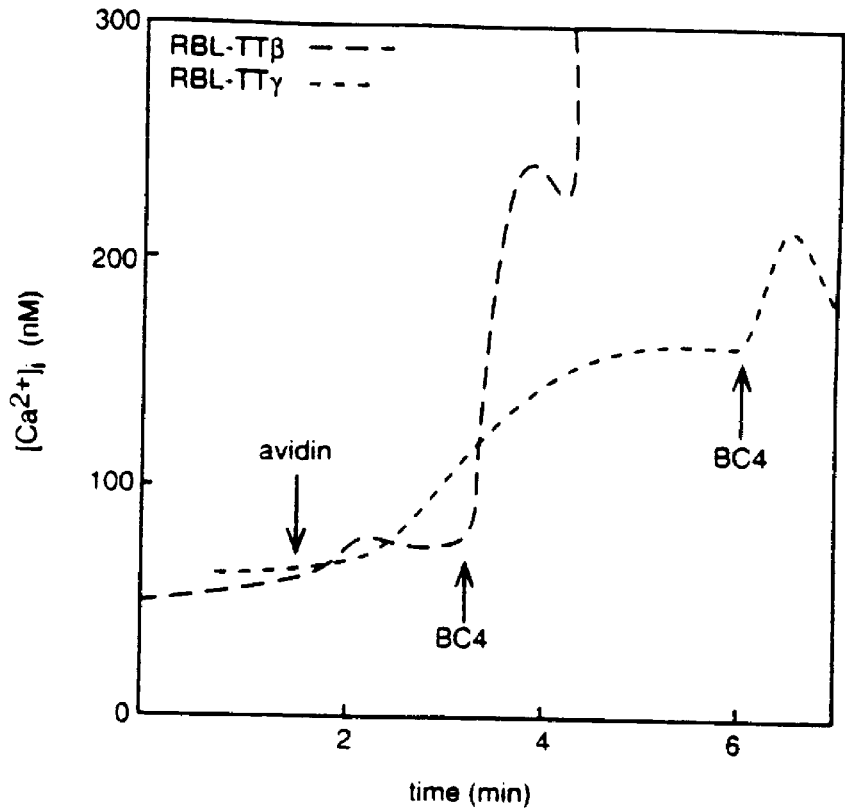

The ARAM-containing Tail of β Mediates Calcium Flux, but Much Less Efficiently than ARAM-γ or Tetrameric FcεRI To determine whether β plays a role in an earlier activation event, the increase in free intracellular calcium, the ability of the TTβ to mediate a calcium signal was investigated. RBL-TTβ and RBL-TTγ cells were saturated with biotinylated anti-Tac B1.49.9, loaded with the calcium-sensitive dye fura-2, and assayed in a spectrofluorometer. Cross-linking of chimeric molecules on RBL-TTβ with avidin leads to a small but reproducible increase in free intracellular calcium (FIG. 12A), but this increase is much smaller than that obtained by stimulation of FcεRI on the same cells with 0.5 μg/ml of the anti-FcεRI α antibody BC4 (FIG. 12A). The same pattern was reproduced with 10 different clones stimulated with 15–45 μg/ml of avidin. This small response is specific, because it is not observed either in the absence of anti-Tac antibody or on untransfected RBL cells. In comparison with the response through TTβ, the increase in free intracellular calcium caused by γ chimera cross-linking in RBL-TTγ is stronger, but this response, too, is slower and weaker than that obtained after stimulation through FcεRI on the same cells (FIG. 12A).

TABLE II

Serotonin Release from Transfected RBL Cells
Transfected RBL were loaded with ($^3$H) serotonin and antibodies. After washing they were triggered with DNP-HSA or avidin. Percent serotonin releases were calculated form the counts in the supernatants and the amounts of incorporated radioactivity.

| Cell Line | Preincubation | Challenge | Percent serotonin release (n = 3) |
|---|---|---|---|
| RBL-TTγ |  | Avidin | 4.7 ± 1.5 |
| RBL-TTγ | Anti-Tac-Biotin | Avidin | 21.2 ± 0.1 |
| RBL-TTγ |  | DNP-HSA | 3.8 ± 2.5 |
| RBL-TTγ | IgE (saturating) | DNP-HSA | 47.9 ± 0.4 |
| RBL-TTγ | IgE (1/5-saturating) | DNP-HSA | 48.7 ± 0.4 |
| RBL-TTβ |  | Avidin | 9.5 ± 1.0 |
| RBL-TTβ | Anti-Tac-biotin | Avidin | 4.6 + 0.6 |
| RBL-TTβ |  | DNP-HSA | 4.4 ± 1.0 |
| RBL-TTβ | IgE (saturating) | DNP-HSA | 56.0 ± 0.6 |
| RBL-TTβ | IgE (1/5-saturating) | DNP-HSA | 65.7 ± 0.6 |

Figure 12B:
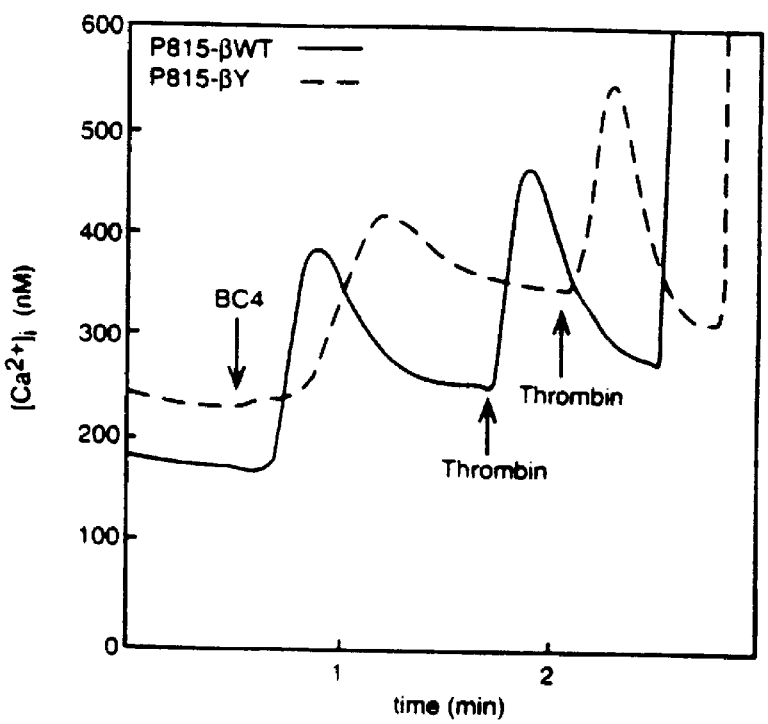

The contribution of ARAM-β in the tetrameric receptor to the calcium signal was assessed by comparing the responses initiated by wild type and mutant receptors. Cross-linking FcεRI on P815-βWT and P815-βY transfectants with 0.5 μg/ml of the anti-FcεRI α antibody BC4 induces a comparable signal from both the wild type and the tyrosine-mutated receptor (FIG. 12B).

From the facts that TTβ generates a weak calcium flux and that mutating the tyrosine residues of β does not affect dramatically the calcium flux generated through FcεRI, it may be concluded that ARAM-β plays only a minimal role in calcium flux. ARAM-γ alone is also less potent than tetrameric FcεRI. This indicates that the two ARAMs are not equivalent and that the potency of either one alone is insufficient to account for the activity of the whole receptor.

The ARAM-containing Tail of β Plays a Role in Receptor Phosphorylation

The role of β in the earliest observable activation event, phosphorylation of receptor β and γ subunits, which occurs within seconds of FcεRI engagement was investigated (Paolini et al., 1991). To compare phosphorylation of intact and mutated receptors in P815-βWT and P815-βY, respectively, the cells were labeled in vivo with [$^{32}$P] orthophosphoric acid, incubated with anti-DNP IgE, and then activated (or not) by cross-linking with DNP-HSA. After lysis, cell surface FcεRI were immunoprecipitated and resolved on SDS-PAGE. Receptor phosphorylation in P815-βWT resembles that in RBL with basal level phosphorylation of receptor β and γ subunits in resting cells and an increase after triggering. Radioanalytic imaging analysis shows that the phosphorylation level on β increases by a factor 2 and on γ by 13. According to phosphoamino acid analysis, this increase is on tyrosine for both β and γ. In P815-βY there is reduced phosphorylation of β in the resting state and no increase upon activation. As would be expected, there is no tyrosine phosphorylation on the β subunit, demonstrating that the mutations destroyed all the tyrosine phosphorylation sites. However, quite surprisingly, the phosphorylation levels of resting as well as stimulated γ are also affected by the mutation in β; although the increase in γ phosphorylation is comparable with that in the wild type receptor (by about a factor of 10), the overall levels are reduced to approximately half of those found in wild type FcεRI.

To examine directly whether the association of kinase activity with the receptor is influenced by the mutation in β, in vitro kinase assays were performed on immunoprecipitated FcεRI from P815-βWT and P815-βWT cells were incubated with different concentrations of anti-DNP IgE (5, 1, and 0.2 μg/ml at 1×10$^7$ cells/ml) and P815-βY cells with 5 μg/ml of anti-DNP IgE. Immune complex kinase assays were performed on receptors which had been immunoprecipitated with anti-IgE from unstimulated and stimulated cells.

Receptor cross-linking on P815-βWT causes an increase in phosphorylation of β and γ subunits, the intensity of which is proportional to the number of receptors engaged. In contrast, immunoprecipitates from triggered P815-β display only a weak phosphorylation on γ, visible on after overexposure. Immunoblotting confirms that both β and γ are present in all samples, and significantly more receptor molecules from mutant cells were immunoprecipitated than are required to see increased phosphorylation on wild type receptors. Together with the results of the experiments in intact cells, these results indicate that the C-terminal tail of β with a specific kinase, or alternatively, could alter the activity of the kinase.

The ARAM-containing Tail of β Controls Phosphorylation of Other Cellular Proteins P815-βWT and P815-βY were labelled with [$^{32}$P] orthophosphoric acid and stimulated them through FcεRI as above. After lysis, tyrosine phosphorylated proteins were immunoprecipitated using 4G10, resolved by SDS-PAGE, and revealed by autoradiography. In P815-βWT, activation induces phosphorylation of various substrates: two at approximately 35 and 55 kDa, three in the 70–80 kDa range, and additional species at higher molecular masses, as well as FcεRI β and γ identified by Western blotting in a similar experiment. Of these, FcεRI β and γ are absent or reduced in activated P815-βY, as observed after receptor precipitation. In addition, the 55-kDa band is absent and the highest band in the 70–80-kDa range is reduced in the mutant, indicating that phosphorylation of additional proteins besides FcεRI γ is controlled by the C-terminal tail of β.

Lyn Binds to Nonactivated FcεRI β via the C-terminal Tail of β, but Not to γ

The Src family kinase, Lyn, associates with FcεRI and is activated after FcεRI aggregation. However, the γ chimera is unable to activate Lyn. A question, therefore, was whether Lyn might interact preferentially with β. First, to verify that Lyn is expressed in P815, in vitro kinase assays were preformed after immunoprecipitation with anti-Fgr, -Hck, -Lck, -Lyn, -Fyn, and -Yes antibodies. In that analysis, only Lyn was detected in P815. An in vitro kinase assay of receptor immunoprecipitates was then used to label the kinase(s) associated with the receptor (Bell et al., 1992; Yamanashi et al., 1991). Surface FcεRI was immunoprecipitated from nonstimulated P815-βWT and P815-βY cells and subjected to in vitro kinase assay. To identify Lyn as a kinase associated with the receptor, the labelled immune complexes were eluted from the beads and reprecipitation was performed with anti-Lyn or a control antibody. It should be noted that the presence of phosphorylated Lyn after the second immunoprecipitation would then reflect its association to surface FcεRI. In fact, anti-Lyn specifically precipitates Lyn as a band of 56 kDa from wild type receptor complexes. The intensity of this band is minimally reduced when the tyrosines in ARAM-β are mutated.

The same experiments were performed with nonactivated RBL-TTβ and RBL-TTγ, in which the chimeras are not visibly phosphorylated. In these cells, immune complex kinase assays were performed for both the endogenous tetrameric FcεRI and the chimeras. In two separate experiments Lyn is reprecipitated from the FcεRI immunoprecipitates of both cell lines; the anti-Lyn antibody, although, reprecipitates Lyn only from the TTβ chimera and not from the TTγ chimera. A logical conclusion is that Lyn interacts preferentially with the C-terminal tail of β independently of any triggering and that this interaction does not critically require the tyrosine residues in ARAM-β This extends the observation that the γ chimera is unable to activate Lyn.

The γ Tail Controls Phosphorylation of a 72-kDa Substrate, the Tyrosine Kinase Syk Proteins which become phosphorylated on tyrosine after cross-linking the Tac chimeras on RBL-TTβ and RBL-TTγ were compared. Cells were labelled with [$^{32}$P] orthophosphoric acid, incubated either with anti-DNP IgE or biotinylated anti-Tac, and then activated (or not) by cross-linking with either DNP-HSA or avidin. After cell lysis, tyrosine-phosphorylated proteins were immunoprecipitated and resolved on SDS-PAGE. Cross-linking of naturally expressed FcεRI on RBL-TTγ and RBL-TTβ leads to increased phosphorylation of several proteins, including the receptor β and γ subunits (Li et al., 1992) and a 72-kDa protein (Benhamou et al., 1990; Yu et al., 1991). When RBL-TTγ cells are stimulated through the chimera with biotinylated anti-Tac and avidin, the appearance of two phosphorylated species was observed, one at approximately 200 kDa (better visible on a shorter exposure) and another at 72 kDa, the latter one of which comigrates with the 72-kDa band from the same cells triggered through FcεRI. In RBL-TTβ, triggering through the chimera also induces phosphorylation of a 200-kDa band, but a 72-kDa band was not detected.

In neither RBL-TTβ nor -TTγ can a phosphorylated band be detected in the region corresponding to the molecular weight of the chimeras, which was determined by running iodinated chimera precipitated from the same cells on a separate gel as well as by Western blotting. Similarly, on an anti-Tac precipitation of the supernatants after anti-phosphotyrosine precipitation, no phosphorylated TTγ chimera is visible, even though the chimera is detected by Western blotting with an anti-γ antibody. In addition, Triton X-100-insoluble fractions of the lysates were treated with radioimmune precipitation buffer and the supernatants, following a second centrifugation, were precipitated with the anti-phosphotyrosine antibody. A phosphorylated chimera is not detected under these conditions either. However, phosphorylation of the chimeras at a lower level than the detection limit of this technique cannot be excluded.

Various groups have reported on the phosphorylation of a 72-kDa band induced by triggering through FcεRI (Hutchcroft et al., 1992). More recently, this band has been identified as the Syk kinase Benhamou et al., 1993). To identify the 72-kDa band present as Syk, in vitro kinase assays were performed on anti-phosphotyrosine precipitates before and after triggering through the endogenous FcεRI or through TTγ, followed by elution and reprecipitation with anti-Syk in the absence or presence of the peptide used to produce the antibody. A band of 72 kDa is specifically reprecipitated by the anti-Syk antibody after FcεRI and TTγ triggering. From a radioanalysis of the counts associated with the 72 kDa, it was determined that, on a per receptor basis (see FIG. 11), TTγ triggering is about 20-fold less efficient than FcεRI triggering.

EXAMPLE 10

A Modified RBL Cell Line Which Expresses the Human FcεRI Receptor

A modified RBL cell line was made by introducing by transfection into RBL cells the cDNA's from the human FcεRI α gene subcloned into the vector pCDL-SRα 296 (available from DNAX, Palo Alto, Calif.), from the human β gene using the same vector, and the human γ gene subcloned into pBJlneo.

RBL cells expressing human FcεRI α, β, γ are able to generate signals, in particular calcium fluxes and serotonin release after activation through human FcεRI. These cells, therefore constitute a tool to test in vitro potential inhibitors of the function of human FcεRI (as described herein for inhibitors of IgE or Lyn binding).

EXAMPLE 11

Detection of a Candidate Inhibitor Substance

In still further embodiments, the present invention concerns a method for identifying new FcεRI inhibitory compounds, which may be termed as "candidate substances." It is contemplated that this screening technique will prove useful in general identification of any compounds and/or functions that will serve the purpose of inhibiting the formation of FcεRI as measured by various cell activation assays. (Mouse Interleukin-2 ELISA kit, Alberts et al., pp. 179–180, Adamczewski et al. 1992, Barones et al., 1991).

Thus, in these embodiments, the present invention is directed to a method for determining the ability of a candidate substance to inhibit the formation and/or function of the human FcεRI complex, the method including generally the steps of:

(a) obtaining a composition comprising the human alpha, beta and gamma subunits of FcεRI that are capable of complexing to form a functional and/or expressed receptor;

(b) admixing a candidate inhibitor substance with the composition; and (c) determining the functional or expressed ability of the admixture.

An important aspect of the candidate substance screening assay hereof is the ability to prepare a composition of alpha, beta and gamma subunits in a relative purified form, for example, in a manner discussed herein. An aspect of the candidate substance screening assay in that without at least a relatively purified preparation, one will not be able to assay specifically for FcεRI inhibition, as opposed to the effects of the inhibition upon other substances in the extract which then might affect the receptor. In any event, the successful cloning and isolation of the beta subunit now allows for the first time the ability to identify new compounds which can be used for inhibiting the FcεRI in specific ways, thereby inhibiting the effects of the FcεRI when bound to IgE.

The candidate screening assay is quite simple to set up and perform, and is related in many ways to the assays discussed herein for determining FcεRI activity. After obtaining a relatively purified preparation of the alpha, beta and gamma subunits, one will desire to simply admix a candidate substance with the preparation, preferably under conditions which would allow the receptor to form but for inclusion of an inhibitory substance. Thus, for example, one will typically desire to use cell activation assays as indirect measures of the presence of a functional receptor, or receptor expression, or both.

Accordingly, one will desire to measure or otherwise determine the activity of the relatively purified receptor in the absence of the assayed candidate substance in order to assess the relative inhibitory capability of the candidate substance.

In still further embodiments, the present invention is concerned with a method of inhibiting receptor formation and/or function which include subjecting the subunits to an effective concentration of a candidate substance identified in accordance with the candidate screening assay embodiments. This is, of course, an important aspect of the invention in that it is believed that by inhibiting the receptor one will be enabled to treat or prevent various aspects of allergic reactions. It is believed that the use of such inhibitors to block the release of histamine by binding of IgE to FcεRI and serve to treat or palliate the symptoms of an allergic response. Inhibitors may be useful by themselves or in conjunction with other therapies.

RBL cells expressing human FcεRI can be used to test for inhibitors of IgE binding using the following test. The cells are grown in a 96-well plate. They are incubated with a candidate inhibitor and labelled (biotinylated) human IgE. Then the binding of IgE, or absence of it, is detected by incubation with a ligand for biotin (avidin) coupled to an enzyme (horseradish peroxidase), then with a colored substrate for the enzyme (if IgE is bound, avidin will bind and the substrate will react with the enzyme producing a colored substance, the amount of which can be measured accurately).

Another in vitro assay makes use of the binding between Lyn and the ARAM-containing cytoplasmic tail of the human β subunit. In a rather simple form of the assay, a synthetic β-derived peptide is prepared and linked to a solid substrate, e.g., a test tube. Lyn is made, for example, by recombinant DNA technology wherein a Lyn coding sequence is incorporated into a bacterial culture, in such a form that it produces Lyn. The Lyn is labelled, for example, by a fluorescent or radioactive molecule known to those of skill in the art. The β-derived peptide when mixed in appropriate ratios should result in no free label because Lyn is bound to the peptide.

Candidate inhibitor substances are incubated in the assay to see if free label is detected. Evidence of free label indicates inhibition of the Lyn-β-derived peptide binding. A candidate inhibitor substance that evokes such a reaction, is a candidate for which further testing is suggested.

In a more sophisticated form of a Lyn-β-derived peptide binding assay, a cell is used in which the binding of Lyn-ARAM is expected. The cell has a DNA molecule capable of encoding at least the portion of the human β subunit necessary for Lyn binding. Lyn produced by the cell is labelled. A candidate inhibitor substance is added to the in vivo assay to determine whether free label is detectable. If it is, this indicates inhibition of Lyn-β-derived peptide binding, warranting further testing of the substance.

EXAMPLE 12

Identification and Use of FcεRI Inhibitors

If the action of receptor of IgE is inhibited, the allergic reaction will not proceed. This inhibition may be either at the level of transcription, translation, or protein action. Interference with transcription would necessitate interference with mRNA formation on the DNA template. Preferably, interference with the translation would necessitate interfering with the synthesis of proteins on the mRNA template. Alternatively, the action of the receptor may itself be disrupted either by destroying the structure of the receptor, prohibiting its formation, or binding the receptor or components thereof irreversibly to inhibitors.

Specifically designed peptides which block the function of the receptor are extremely valuable in preventing and treating allergic diseases. Embodiments of these blockers (antagonists) include any substrate analogues or inhibitor, e.g., oligopeptides or their derivatives which contain the amino acid sequence of the IgE binding site. Methods for identifying suitable inhibitors form candidate substances are disclosed in Example 10.

EXAMPLE 13

Preparation of the Human β Polypeptide by Recombinant Techniques

It is an additional object of the present invention to provide a ready means for producing the human beta subunit for use in detecting inhibitors, to develop treatment modalities, to develop antibodies for detection of the subunit, and to develop inactive mutants of the human beta subunits, which may also be use to inhibit formation of the FcεRI. Such mutants may be introduced into transgenic animals, for example, to produce animals useful for β assays.

An exemplary embodiment for preparing the beta subunit protein is to prepare a nucleic acid segment which includes a nucleic acid sequence capable of encoding the desired protein or polypeptide. This segment may be that which encodes the entire subunit or only some portion of it, for example, the alpha or gamma binding domain of the subunit. The segment may be as small as that capable of triggering a positive signal with an antibody, thereby, identifying the presence of a beta subunit. Segments functionally equivalent to those shown in FIG. 2 or FIG. 10, may also be selected depending on the desired polypeptide to be produced. Functional equivalence may be determined by testing whether the segment can cause cell activation using techniques disclosed herein to detect inhibitors from among candidate substances.

The nucleic acid segment selected is transferred into an environment appropriate for expression of the segment as a polypeptide. This environment may be a vessel containing a mixture capable of inducing expression. Alternatively, the segment may be transferred to a host cell by transformation, transfection via a recombinant expression vector, electroporation, or a "gene gun." The host cell may be selected from CHO cells, COS-7 cells, T cells, KU812 cells, RBL, P815 cells, or the like.

The recombinant expression vector will generally include a promoter. Embodiments of promoters are the α4 promoter, or any other suitable prokaryotic or eukaryotic promoters.

EXAMPLE 14

Antibodies Against the Proteins of the Present Invention

In other embodiments, the invention concerns the preparation of antibodies to the beta subunit of FcεRI and species derived therefrom, either recombinant or nonrecombinantly prepared.

Compositions which include monoclonal antibodies of the present invention may be prepared by first fusing spleen cells of a rodent with myeloma cells from the same rodent species, wherein the rodent providing the spleen cells have been immunized with the β subunit peptide, precursor, segment including ARAM-β related peptides. The rodent species utilized will generally be a mouse. Of course, where a beta subunit is prepared which incorporates structural variations over the ones disclosed herein, it will likely be able to successfully employ a hybridoma system according to the species of interest.

In addition, the present invention provides a method for isolating beta subunits from other species which may be found antigenically cross-reactive with that of the human or rodent subunit. This method includes preparing an immunoabsorbent material having attached thereto an antibody to the subunit. Numerous immunoabsorbent materials are known to those skilled in the art and include, for example, Affi-Gel, Cn-Sepharose, protein A=Sepharose, and numerous other well know immunoadsorbent techniques. All such techniques of the immuno cross-reactive species (for a more complete listing, see *Monoclonal Hybridoma Antibodies: Techniques and Applications*, John G. Hurrell, ed. CRC Press, 1982, incorporated herein by reference).

MATERIALS AND METHODS

Screening of cDNA and Genomic Libraries

The human basophil cDNA library and the human leukocytes genomic library have been described before and are available (Kuster, 1990). The human lung cDNA library (Miller, 1989) and a human skin cDNA library were provided by L. B. Schwartz (Medical College of Virginia, Richmond).

The following probes were prepared for screening the various libraries: The EcoRI-EcoRV fragment of rat β (Kinet, 1988) and the EcoRI fragment of mouse β (Ra, 1989), both of which contain the entire coding sequence of β and part of the 3' untranslated region. Fragments of the coding region of rat β cDNA (bp 1–304) and mouse β cDNA (bp 433–708) were made by polymerase chain reaction (PCR). Multiple oligonucleotides corresponding to various regions of rat, mouse and human β were synthesized on a model 380A automated DNA synthesizer (Applied Biosystems, Foster City, Calif.). All double stranded DNA probes were radiolabelled by random primer labeling and the oligonucleotides by end labeling as described elsewhere (Davis, 1986).

Hybridization and washing conditions and procedures for plaque purification subcloning, sequencing and DNA analysis were as described previously (Kuster, 1990).

cDNA Synthesis by Using the Polymerase Chain Reaction (PCR)

Basophils from 240 ml of blood were purified by double Percoll gradients as previously described (Warner, 1987) and basophil RNA extracted by the guanidium isothiocyanate method (Davis, 1986). Two µg of total RNA were reverse transcribed with Superscript reverse transcriptase using a random 9-mer primer as recommended by the manufacturer (Bethesda Research Laboratories, Gaithersburg Md.). One twentieth of the reaction product was amplified using the following primers: a 23-mer complementary to nucleotide 453 to 476 of the human β coding sequence Seq. I.D. No. 2 and as backward primer a degenerate 21-mer of the mouse and rat β sequences starting 32 nucleotides after the stop codon. Temperature cycles were as follows: 1 cycle of 2 min. 95°/2 min. 94°/5 min. 37°/40 min. 72°, 4 cycles of 40 sec. 94°/1 min. 37°/4 min. 72°, and 36 cycles of 40 sec. 94°/1 min. 50°/4 min. 72° followed by a single 15 minute extension. One µl of this reaction was reamplified omitting cycles 2 to 5 and the amplification product subcloned into pCR1000 using the TA cloning kit (Invitrogen, San Diego, Calif.).

Direct Sequencing of Gene Fragments Obtained by PCR

Purified insert-containing phage DNA from the leukocyte genomic library was linearized with NotI and 100 ng amplified with primers flanking the region to be sequenced. DNA amplification was achieved using 40 of the following cycles: denaturation for 1 min. at 94° C., annealing or 2 min. at 45°–50° C. and extension for 3–6 min. at 72° C. Subsequently 1 µl of the amplified material was reamplified in three separate reactions (50 µl) Under identical conditions omitting one of the 2 primers in order to generate single stranded DNA. The three reactions were pooled, applied to an Ultrafree MC 30.000 spin column (Millipore, Bedford Mass.), and washed four times before being evaporated by vacuum. The single stranded DNA was sequenced by using the omitted primer or an internal primer. The comparison of sequences obtained by this method or by sequencing non amplified fragments being subcloned in pGEM vectors revealed no differences.

Sequencing the Transcription Start Site

PCR was used to define the transcription start site. Procedures published elsewhere (Frohman, 1987) were modified as follows: 5 µg RNA were reverse transcribed as detailed above by using a primer corresponding to nucleotide 906 to 884 of the coding region. The resulting product was washed on a Centricon 100 column (Amicon, Beverly Mass.) and a poly-A tails were at both ends added using terminal transferase (Bethesda Research Laboratories, Gaithersburg Md.) as recommended by the manufacturer. One sixth of this reaction was amplified with the following 2 primers: a 33-mer consisting of the M13 primer sequence followed by 17 T's and for the 3' end a primer derived from nucleotide 786 to 763 of the human β coding region sequence. Subsequently an internal amplification was performed exchanging the 3' primer for one equivalent to nucleotide 644 to 624. Finally, single stranded DNA was produced for sequencing by using an oligonucleotide corresponding to nucleotide 509 to 488 as the only primer. For all PCR's the annealing temperature was 45° C., the extension time 3 min.

Analysis of the Transcription Start Site by 5' Extension

An end labeled oligonucleotide corresponding to the negative strand at nucleotide 54 to 33 after the start codon was hybridized overnight at 42° C. to either 10 µg total RNA from enriched basophils or 10 µg tRNA, followed by extension with Superscript reverse transcriptase (Bethesda Research Laboratories, Gaithersburg Md.) at 45° C. for 90 min. The primer-extended products were separated on a 5% polyacrylamide urea gel in parallel with the sequencing reactions of the genomic DNA.

Cell Line KU812

A myeloid cell line (KU812) was established from a patient with blastic crisis of chronic myelogenous leukemia.

Histoblasts were morphologically characteristic of immature basophils and basophil colonies were grown in agar culture of the blood mononuclear cells. Suspension culture of his blood cells was continue for more than 2.5 years. The KU812 cells morphologically showed a fine reticular nuclei with nucleoli, and some of them contained metachromatic granules with toluidine blue (TB) staining. These granules were positive for astra blue (AB) staining. Immunological marker studies revealed that there were no lymphoid characters except Fc receptors. The KU812 cells grew colonies in in vitro agar cultures, which were proved to be composed of basophils by TB staining and AB staining. Cytogenetic analysis showed marked aneuploidy and was positive for the Philadelphia chromosome (Ph$^1$). The cell lysate was proved to contain histamine. These data suggest that KU812 is a cell line from leukemic basophil precursors. This is the first human basophil cell line. KU812 is useful in clarifying the mechanism of basophilic differentiation of the stem cells.

Antibodies

Antibodies were purchased from the following source; anti-phosphotyroaine 4G10 from Upstate Biotechnology, Inc. (Lake Placid, N.Y.); goat anti-mouse IgG and goat anti-rabbit IgG antibodies conjugated to alkaline phosphatase, F(ab')$_2$ fragment goat anti-mouse IgG (H+L), and rabbit anti-mouse IgG (H+L) antibodies from Jackson Immunoresearch (West Grove, Pa.), anti-Tac B1.49.9 (15) from Amac (Westbrook, Me.), anti-Fgr, anti-Hck, anti-Lck, anti-Yes from Santa Cruz (Santa Cruz, Calif.). The anti-Syk antibody 996 was raised in rabbit against a synthetic peptide representing amino acids 339–349 of Syk (Taniguchi et al., 1991). Anti-DNP monoclonal mouse IgE, rabbit anti-mouse IgE, anti-rat FcεRI β subunit monoclonal antibody, JRK, and rabbit anti-FcεRI γ subunit antibody were prepared as described (Paolini, et al., 1991). Anti-rat FcεRI α chain, BC4, was obtained from Dr. R. Siraganian (National Institutes of Health, Bethesda, Md.) (Basciano et al., 1986). Anti-Tac hybridomas were obtained from ATCC (Rockville, Md.) (7G7B6) (19) and from Dr. T. Waldmann (National Institutes of Health, Bethesda, Md.) (HD245) (20). Anti-Lyn and anti-fyn were from Dr. J. Bolen (Bristol-Myers Squibb Pharmaceutical Research Institute, Princeton, N.J.) or purchased from Santa Cruz (Santa Cruz, Calif.).

Cell Culture and Transfections

The extracellular and transmembrane parts of human Tac (up to base pair 957) (Leonard et al., 1984) were joined by polymerase chain reaction to the cytoplasmic C-terminal part of rat β (base pairs 652–786) (Kinet et al., 1988) to give the chimeric cDNA including Tac and FcεRI β (TTβ). The mutated form of rat β cDNA (βY) in which tyrosines 218, 224, and 228 are changed to phenylalanines was made by replacing the segment from base pair 690 to base pair 786 with a double-stranded oligonucleotide including the mutations. These constructs were subcloned into pCDL-SRα 296 (Takebe et al., 1988). RBL-2H3 cells were cotransfected by electroporation with the TTβ construct and pSV2neo to generate RBL-TTβ. P815 cells were co-electroporated with the wild type (βWT) or mutated β (βY) cDNAs, the rat α cDNA (Kinet et al., 1987) in pCDL-SRα 296 and the rat γ cDNA (Blank et al., 1989) in pBJlneo (Lin et al., 1990), a derivitative of pCDL-SRα 296 containing a neomycin resistance cassette, to generate P815-βWT and P815-βY clones. Resistant clones were selected with G418 (0.5 mg/ml for RBL transfectants and 1.0 mg/ml for P815 transfectants). One clone of RBL-TTγ expressing a chimera between Tac and the cytoplasmic part of γ was obtained from Francois Letourneur (1991). More RBL-TTγ clones were generated by transfecting RBL cells with the corresponding cDNA subcloned in pCDL-SRα 296. Surface expression was analyzed on a FACScan (Becton Dickinson, San Jose, Calif.) after staining with FITC-labeled mouse IgE or with FITC-labeled anti-Tac B1.49.9. [$^{125}$I] iodination of IgE and anti-Tac 7G7B6 was performed using chloramine T.

Serotonin Release

The assay was performed as described in Adamczewski (1992).

Calcium Flux Measurement

Cells were saturated with IgE or biotinylated anti-Tac B1.49.9 and then loaded with a fura-2 AM (2 μM for RBL cells and 1 μM for P815 cells) for 45 min at 37° C. in a buffer (pH7.4) containing 136 mM NaCl, 5 mM KCl, 1 mM CaCl$_2$, 1 mM MgCl$_2$, 5.6 mM glucose, 10 mM HEPES, 0.1% bovine serum alburmin, and 2.5 mM Probenecid. Cells were analyzed in a cuvette on a Deltascan spectrofluorometer (Photon Technology International Inc., South Brunswick, N.J.) with excitation set at 340 and 380 nm and emission at 500 nm. Calcium concentrations were calculated using the published value of 2.24×10$^{-7}$ for the K$_d$ for fura-2 at 37° C. (Grynkiewicz et al., 1985).

Phosphorylation on Intact Cells

Cells were processed as described (Paolini et al., 1991) with the following modifications for studying Tac chimeras: cells were incubated with 5 μg/mL of biotinylated anti-Tac B1.49.9 for 2 h at 37° C. and triggered at 37° C. with medium alone or avidin; the post-nuclear supernatants were not precleaned on protein A beads, and the control immunoprecipitation was performed with IgG-Sepharose beads (Pharmacia LKB Biotechnology Inc.). Western blotting was performed as described. Two-dimensional thin layer-electrophoresis electrophoresis of phospho-amino acids was performed by a modification of the method of Hunter and Sefton as described (Paolini et al., 1992). Surface [$^{125}$I] iodination of RBL-TTγ was performed using lactoperoxidase.

In Vitro Kinase Assay

Assays were performed as described (Eiseman and Bolen, 1992; Paolini, 1992), with some modifications. Following immunoprecipitation, the beads were washed six times with lysis buffer and once with kinase buffer (30 mM HEPES (pH 7.4), 5 mM MgCl$_2$, 5 mM MnCl$_2$, 100 μM sodium orthovanadate) and then resuspended in kinase buffer containing 1 μM ATP and 12.5 μCi OF [γ$^{32}$P]ATP. After 3 min of incubation at 30° C., the beads were washed twice with lysis buffer, and the immunoprecipitates were analyzed by SDS-PAGE and autoradiography.

In some experiments, after the kinase assay and the washes, the anti-phosphotyrosine immunoprecipitates were eluted from the beads with 10 mM phenylphosphate in lysis buffer at 4° C. for 30 min and the anti-receptor immunoprecipitates were eluted with 1% sodium deoxycholate in 10 mM Tris (pH 7.4), 20 mM NaCl for 30 min at 37° C. Repricipitation was performed with an anti-Lyn, anti-Syk, or control antibody. In some cases, the repricipitation was performed in the presence of 10 μg of the peptide used to generate the corresponding antibody. The second immunoprecipitates were analyzed by SDS-PAGE and autoradiography. Band intensities on gels were quantitated using a radioanalytic imaging system (Ambis Systems, San Diego, Calif.). This repricipitation technique allows the kinase(s) present in anti-receptor precipitates to be identified.

Other Methods

Northern and Genomic Southern blots were performed as described elsewhere (Davis, 1986). The various cDNAs were subcloned into the eukaryotic expression vector PCDL-SR α 296 for the transfection studies (Takebe, 1988). COS-7 cells were transfected by the standard DEAE-Dextran method (Maniatis, 1982), except that a 3 minute incubation of the transfected cells in 10% DMSO in media as added after the chloroquine treatment.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

Documents Cited

The references listed below are incorporated herein by reference to the extent that they supplement, explain, provide a background for, or teach methodology, techniques and/or compositions employed herein.

Adamezewski, M., Paolini, R. and Kinet, J. P. (1992) *J. Biol. Chem.* 267, 18126–18132.

Alber, G. Miller, L., Jelsema, C. L., Varin-Blank, N., and Metzger, H. (1991) *J. Biol. Chem.* 266, 22613–22620.

Alberts et al. (1983), *Molecular Biology of the Cell*, pp. 179–180.

Baranes and Razin, *Blood*, 78, 2354–2364 (1991).

Collaborative Biomedical Products, Becton-Dickinson, Catalog No. 30032, lot 904092, Mouse Interleukin-2 ELISA kit.

Bell, G. M., Bolen, J. B. and Imbeden, J. B. (1992) *Mol. Cell. Biol.* 122, 5548–5554.

Benhamou, M., Ryba, N. J. P., Kihara, H., Nishikata, H., and Siraganian, R. P. (1993) *J. Biol. Chem.* 268, 23318–23324.

Benhamou, M., Gutkind, J. S., Robbins, K. C., and Siraganian, R. P. (1990) *Proc. Nat'l Acad. Sci. U.S.A.* 87, 5327–5330.

Blank, U., Ra C., Miller, L., White, K., Metzger, H., and Kinet, J. P. (1989) *Nature* 337, 187–189.

Davis, L. G., Dibner, M. D., and Battey, J. F. (1986) *Basic Methods in Molecular Biology*, Elsevier Science Publishing Co., New York.

Eiseman, E., and Bolen, J. (1992) *J. Biol. Chem.* 267, 21027–21032.

Eiseman, E., and Bolen, J. (1992) *Nature*, 355, 78–80.

Frohman, M. A., Dush, M. K., and Martin, G. R. (1988) *Proc. Nat'l Acad. Sci.* 85, 8999–9002.

Grynkiewicz, G., Poenie, M., and Thien, R. (1985) *J. Biol. Chem.* 260, 3440–3450.

Huppi, K., Siwarski, D., Mock, B. A., and Kinet, J. P. (1989) *J. Immunol.* 143, 3787–3791.

Huppi, J., Mock, B. A., Hilgers, J. Kochan, J., and Kinet, J. P. (1988) *J. Immunol.* 141, 2807–2810.

Hutchcroft, J. E., Geshian, R. L., Deanin, G. G., and Oliver, J. M. (1992) *Proc. Nat'l Acad. Sci. U.S.A.* 89, 9107–9111.

Irving, B. A., Chan, A. C., and Weiss, A. (1993) *J. Exp. Med.* 177, 1093–1103.

Kinet et al. (1987) *Biochemistry* 26, 4605–4610.

Kinet, J. P., Blank, U., Ra, C., White, K., Metzger, H., and Kochan, J. (1988) *Proc. Nat'l Acad. Sci. U.S.A.* 85, 6483–6487.

Kinet, J. P., Metzger, H., Hakimi, J., and Kochan, J. (1987) *Biochemistry* 26, 4605–4610.

Kochan, J., Pettine, L. F., Hakimi, J., Kisshi, J., and Kinet, J. P. (1988) *Nucleic Acids Res* 16, 3584–3594.

Kuster, H., Thompson, H., and Kinet, J. P. (1990) *J. Biol. Chem.* 265, 6448–6452.

Le Coniat, M., Kinet, J. P., and Berger, R. (1990) *Immunogenetics* 32, 183–186.

Leonard, W. J., Depper, J. M., Crabtree, G. R., Rudikoff, S., Pumphrey, J., Robb, R. J., Kronks, M., Svetik, P. B., Peffer, N. J., Waldmann, T. A. and Greene, W. C. (1984) *Nature* 311, 626–635.

Letourneur, O., Kennedy, I. C. S., Brini, A. T., Ortaldo, J. R., O'Shea, J. J. and Kinet, J. P. (1991) *J. Immunol.* 147:2652–2656.

Letourneur, F., and Klausner, R. D. (1991) *Proc. Nat'l Acad. Sci. U.S.A.* 88, 8905–8909.

Li, W., Deanin, G. G., Margolis, B., Schlessinger, J., and Oliver, J. M. (1992) *Mol. Cell. Biol.* 12, 3176–3182.

Lin, A. Y., Devaux, B., Green, A., Sagerstrom, C., Elliott, J. F., and Davis, M. M. (1990) *Sci.* 249, 677–679.

Liu, F. T., Albrandt, K., and Robertson, M. W. (1988) *Proc. Nat'l Acad. Sci. U.S.A.* 85, 5639–5643.

Maniatis, T., Fritsch, E. F., & Sambrook, J. (1982) *Molecular Cloning, a Laboratory Manual*, Cold Spring Harbor Laboratory, Cold Spring Harbor, N.Y.

Metzger (1986), Miller, J. S., Westin, E. H., and Schwartz, L. B. (1989) *J. Clin. Invest.* 84, 1188–1195.

Miller, L., Blank, U., Metzger, H. and Kinet, J. P. (1989) *Science* 244, 334–337.

Mostov et al. (1984) *Nature* (London) 308, 37–43.

Paolini, R., Jouvin, M. H. E., and Kinet, J. P. (1991) *Nature* 353, 855–858.

Paolini, R., Numerof, R., and Kinet, J. P. (1992) *Proc. Nat'l Acad. Sci. U.S.A.* 89, 10733–10737.

Ra, C., Jouvin, M. H. E., and Kinet, J. P. (1989) *J. Biol. Chem* 264, 15323–15327.

Ra, C., Jouvin, M. H. E., Blank, U., and Kinet, J. P. (1989) *Nature* 341, 752–754.

Reth, M. (1989) *Nature* 338, 383–384.

Ravetch, J. et al. (1986) *Science* 234, 718–725.

Samelson, L. E., and Klausner, R. D. (1992) *J. Biol. Chem.* 267, 24913–24916.

Shimizu, A., Tepler, I., Benfey, P. N., Berenstein, E. H., Siraganian, R. P., and Leder, P. (1988) *Proc. Nat'l Acad. Sci. U.S.A.* 85, 1907–1911.

Takebe, Y., Seiki, M., Fujisawa, J. -I., Hoy, P., Yokota, K., Arai, K. -I., Yoshida, M., Arai, N. (1988) *Mol. Cell. Biol.* 8, 466–472.

Tepler, I., Shimizu, A., and Leder, P. (1989) *J. Biol. Chem.* 264, 5912–5915.

Taniguchi, T., Kobayashi, T., Kondo, J., Takahashi, K., Nakamura, H., Suzuki, J., Nagal, K., Yamada, T., Nakamura, S., and Yamamura, H. (1991) *J. Biol. Chem.* 266, 1570–15796.

Varin-Blank, N., Metzger, H. (1990) Expression of mutated subunits of the high affinity Mast cell receptor for IgE. *J. Biol. Chem.*

Weiss, A. (1993) *Cell* 73, 209–212.

Yamanashi, Y., Kakiuchi, T., Mizuguchi, J., Yamamoto, T., and Toyoshima, K. (1991) *Science* 251, 192–194.

5,807,988

What is claimed is:

1. A polypeptide having an amino acid sequence of a human beta subunit of Fc$_\epsilon$RI, isolated from its natural environment.

2. The polypeptide of claim 1 wherein said polypeptide has the amino acid sequence set forth in Seq. I.D. No. 3.

3. A purified human Fc$_\epsilon$RI beta subunit protein.

4. A purified peptide including an amino acid sequence of an ARAM from a human Fc$_\epsilon$RI beta subunit protein.

5. An isolated peptide comprising the amino acid sequence: Asp-Arg-Val-Tyr-Glu-Glu-Leu-Asn-Ile-Tyr-Ser-Ala-Thr-Tyr-Ser-Glu-Leu-Glu-Asp-Pro-Gly-Glu-Met-Ser (amino acids 216–239 of Seq. I.D. No. 3).

6. A fusion protein comprising the cytoplasmic domain of a human Fc$_\epsilon$RI beta subunit protein.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( x i ) SEQUENCE DESCRIPTION: SEQ ID NO:1:

```
Asp  Arg  Leu  Tyr  Glu  Glu  Leu  His  Val  Tyr  Ser  Pro  Ile  Tyr  Ser  Ala
 1              5                        10                       15
Leu  Glu  Asp  Thr  Arg  Glu  Ala  Ser
                20
```

( 2 ) INFORMATION FOR SEQ ID NO:2:

( i ) SEQUENCE CHARACTERISTICS:
        ( A ) LENGTH: 11298 base pairs
        ( B ) TYPE: nucleic acid
        ( C ) STRANDEDNESS: double
        ( D ) TOPOLOGY: linear ( v i ) ORIGINAL SOURCE:
        ( A ) ORGANISM: Homo sapiens
        ( B ) STRAIN: FcRI beta ( i x ) FEATURE:
        ( A ) NAME/KEY: CDS
        ( B ) LOCATION: join(456..511, 1381..1510, 2026..2160,
                4475..4531, 5079..5237, 5640..5738, 7224..7319)

( x i ) SEQUENCE DESCRIPTION: SEQ ID NO:2:

```
AAGCTTTTCA   AAGGTGCAAT   TGGATAACTT   CTGCCATGAG   AAATGGCTGA   ATTGGGACAC        60

AAGTGGGGAC   AATTCCAGAA   GAAGGGCACA   TCTCTTTCTT   TTCTGCAGTT   CTTTCTCACC       120

TTCTCAACTC   CTACTAAAAT   GTCTCATTTT   CAGGTTCTGT   AAATCCTGCT   AGTCTCAGGC       180

AAAATTATGC   TCCAGGAGTC   TCAAATTTTC   TTATTTCATA   TTAGTCTTTA   TTTAGTAGAC       240

TTCTCAATTT   TTCTATTCAT   CACAAGTAAA   AGCCTGTTGA   TCTTAATCAG   CCAAGAAACT       300

TATCTGTCTG   GCAAATGACT   TATGTATAAA   GAGAATCATC   AATGTCATGA   GGTAACCCAT       360

TTCAACTGCC   TATTCAGAGC   ATGCAGTAAG   AGGAAATCCA   CCAAGTCTCA   ATATAATAAT       420

ATTCTTTATT   CCTGGACAGC   TCGGTTAATG   AAAAA ATG  GAC  ACA  GAA  AGT  AAT         473
                                            Met  Asp  Thr  Glu  Ser  Asn
                                             1                        5

AGG  AGA  GCA  AAT  CTT  GCT  CTC  CCA  CAG  GAG  CCT  TCC  AG   GTAGGTACAA      521
Arg  Arg  Ala  Asn  Leu  Ala  Leu  Pro  Gln  Glu  Pro  Ser  Ser
              10                       15

GGTATTATTT   TTTTCTACCC   TCAGTCACTT   GTGGCAGGGG   AAGTCATAGT   CACGGTGCTT       581

AGGAGATGAA   ACTTTATTGA   TTTAGGCATG   GATCCATCTA   GTTTAATTAA   TATATTGGGT       641

ATGAGGAAGC   TACTTGCTGT   ACTTTCCATG   TGGTTCTCTC   TCCCTGGAGA   GGAACATTTT       701

TACTCAGCTT   GCAAACTGGA   AATAGATTTT   CTCACATTAG   AAGCTCATTT   TCTGGGTATG       761

AGACAGGAGA   GTTCATACTG   TGTATGTAGA   TCTCTGGCTT   CTGGGTCTGA   CATGTGCTGA       821

GGGACACATA   TCCTTCACAC   ATGCTTTTAT   AAATACTTGA   TAAAGTAACC   TGCTTCTTGA       881

TTGGTCTTTA   TAATCCATAA   GCTGTGGGAT   GCTTCTCTGA   AGATGAAAAT   AGTAATAGAG       941
```

| | | | | | |
|---|---|---|---|---|---|
| TCCCATCTAG | CTATTCAAAG | CCATTCCTTC | ATTGTATTCT | GTGCACATGA | AGTTGGGGTT | 1001 |
| TGTTACTGAC | AAAATATATT | CAGATACATT | TCTATGTTAA | AAGGATTGTG | AGATGCATAG | 1061 |
| GTAAATGTGT | TTATTTTCAG | TTTTACTTGT | CAACATAGAT | GAATGAGAAA | GAACTTGAAA | 1121 |
| GTAACACTGG | ATTAAGAATA | GGAAAATTTG | GCATGGATTT | TGCTCCATTT | TGTCCCATCT | 1181 |
| AATCACTTGG | ATAGTGTTCA | GGTGTTCTTG | GTCAGTTACT | TGGATGCTCT | GAGCTTTAGT | 1241 |
| TTCTTGGTGA | TTACAATGAA | GATTTGAATT | ACAGGATGGC | TTTGAAAAAA | TAAACAAAAC | 1301 |
| TCCCCTTTCT | GTCTGTCGAG | AATGTTGCAC | AGGGAGTTAC | AGAATGTTCT | CATGACTGAA | 1361 |
| TTGCTTTTAA | ATTTCACAG | | | | | |

```
                  T  GTG  CCT  GCA  TTT  GAA  GTC  TTG  GAA  ATA  TCT          1411
                     Val  Pro  Ala  Phe  Glu  Val  Leu  Glu  Ile  Ser
                      20                        25

CCC  CAG  GAA  GTA  TCT  TCA  GGC  AGA  CTA  TTG  AAG  TCG  GCC  TCA  TCC  CCA   1459
Pro  Gln  Glu  Val  Ser  Ser  Gly  Arg  Leu  Leu  Lys  Ser  Ala  Ser  Ser  Pro
 30                       35                       40                       45

CCA  CTG  CAT  ACA  TGG  CTG  ACA  GTT  TTG  AAA  AAA  GAG  CAG  GAG  TTC  CTG   1507
Pro  Leu  His  Thr  Trp  Leu  Thr  Val  Leu  Lys  Lys  Glu  Gln  Glu  Phe  Leu
           50                       55                       60

GGG  GTGAGTGAGC CTCCTCCAAC TTTGACTAGA GTAAGGGTTG GGTCTAGAAA                       1560
Gly
```

| | | | | | |
|---|---|---|---|---|---|
| AGAATATTGA | GTTGCATCAA | CTGTTTTCCC | ACTTGGATTC | ATGAGAGGTG | TTAGGTCCTT | 1620 |
| TAAAAAACAT | GGTAGATAAA | GAGTTGACAC | TAACTGGGTC | CTTTTGGGAA | GAGCCAGAAG | 1680 |
| CATTTCCTCA | TAAAGACTTT | AAATTGCTAG | GACGAGAATG | GCCAACAGGA | GTGAAGGATT | 1740 |
| CATAACTTTA | TCTTTACTTA | GATGTAAAGA | ACAATTACTG | ATGTTCAACA | TGACTACATA | 1800 |
| CATAAAGGCG | CATGGAGAAA | AGTATTGGCC | TTCCATGCAT | TAGGTAGTGC | TTGTATCAAT | 1860 |
| TCTTATAGTG | GCTAGGGTAT | CCTGGAAAAT | CTTACGTGTG | GATCATTTCT | CAGGACAGTC | 1920 |
| TAGGACACTA | ACGCAGTTTC | TCATGTTTGG | CTTCTATTAT | TAAAAAATGA | TACAATCTCG | 1980 |
| GGAAAATTTT | TTTGATTTTC | ATGAAATTCA | TGTGTTTTTC | TATAG | GTA  ACA  CAA | 2034 |

```
                                                            Val  Thr  Gln
                                                             65

ATT  CTG  ACT  GCT  ATG  ATA  TGC  CTT  TGT  TTT  GGA  ACA  GTT  GTC  TGC  TCT   2082
Ile  Leu  Thr  Ala  Met  Ile  Cys  Leu  Cys  Phe  Gly  Thr  Val  Val  Cys  Ser
           70                       75                       80

GTA  CTT  GAT  ATT  TCA  CAC  ATT  GAG  GGA  GAC  ATT  TTT  TCA  TCA  TTT  AAA   2130
Val  Leu  Asp  Ile  Ser  His  Ile  Glu  Gly  Asp  Ile  Phe  Ser  Ser  Phe  Lys
           85                       90                       95

GCA  GGT  TAT  CCA  TTC  TGG  GGA  GCC  ATA  TTT  GTGAGTATAT ATCTATAATT          2180
Ala  Gly  Tyr  Pro  Phe  Trp  Gly  Ala  Ile  Phe
              100                      105
```

| | | | | | |
|---|---|---|---|---|---|
| GTTTCTGAAA | TAACACTGAA | CATAGGTTTT | TCTCTTTCTC | AGATCTAACC | AGTTGTTTAT | 2240 |
| TCCCAGTATT | AAGATGATAT | TTATAATTCT | TAATTATAAA | TATATGTGAG | CATATATAAC | 2300 |
| ATAGATATGC | TCATTAACAA | CAACAAAAGA | TTCTTTTTAC | AATTAACGGT | GGGTTAAACA | 2360 |
| TTTAGCCCAC | AGTTTTATCC | CATGAGAAAC | CTGAATCTAA | TACAAGTTAA | ATGACTTGCC | 2420 |
| TAAGGGCCAC | TTGACTAATA | GTAATTGAAC | CTAAACTTTC | AGAATCCAAC | TCCAGGAACA | 2480 |
| TACTTCTAGC | ACTATTCATC | AATAAAGTTA | TATGATAAAT | ACATACAACT | TTATCTGTCA | 2540 |
| ACTAAAAATA | ACAACAGAGG | CTGGGCATGG | TGGCTCACAC | CCGTAATCCC | AGCACTTTGG | 2600 |
| GAGGCTGAGG | CAGGTGGATC | ACCTGAGGTC | AGGAGTTTGA | GACCAGCCTG | ACCAACATGG | 2660 |
| TGAAACCCTCA | TCTCTACTAA | ATATAAAAAA | TTAGCTGAGT | GTGATAGTGC | ATACCTGTAA | 2720 |
| TCCAGCTACT | TAAGAGGCTG | AGGCAGGAGG | CTTGTTTGAA | CCTGGAAGGC | AGAGGTTGCA | 2780 |
| GTGAGCTGAG | ATTGTGCCAT | TGCACTCCAG | CCTGGGCAAT | AAGTGCGAAC | TCTGTCTCAA | 2840 |

| | | | | | |
|---|---|---|---|---|---|
| AATAATAATA | ATAATAATAG | AAAATAAAGT | TGTCTTCATG | AAAAATGAGG | AAAGAGATTG | 2900 |
| CTGGGGTGAG | AAACATTAAG | ATCAATGGGC | ATATGGTGAC | CTTCTATGCC | CTAGAAACTC | 2960 |
| TTTTANGGTA | TTTTCTCCTG | GTATCTCTTT | TACNCATCGT | TCTATCTGGA | AAAATAGGTG | 3020 |
| GATGAGTGAG | ATAATAACGG | TATATACTTT | TTAAAGGTCT | AATTGACATA | TATAAATTGC | 3080 |
| AAGTATTTCA | GATGTCAATT | TGCTAACCTT | GACACACATA | GACACACATG | AAAACATCAC | 3140 |
| CACATTAATA | CAATGTATGT | ATCCATCATT | CCAAAAGCTT | CCCTGTGTAT | CTTTGTAACT | 3200 |
| CTTTCTTCCT | CCCTCCACTC | CTTGTCCTCT | CGTTCCCAAG | AAAACATTGA | TCTGCTTCCT | 3260 |
| GTGAATATAA | ATTAACTTAC | ATTTTTTAGA | GCTTTATATA | AGTATGTTCT | CTTTACTGTT | 3320 |
| TGTCTTCCTT | CGCTGCACAG | TTATTTTGAG | ATTCTTCAAG | TTTTTTCTTT | ATATCGATAC | 3380 |
| TTCATTCACA | AGAATATATT | TTAATTCTAG | ACTATGTCAC | ATTGACTTTG | TCGTCTGCTA | 3440 |
| AATCCTTAGT | GCTCAGATGA | CTTGTTCAGG | ACTCTCCTTG | AACCTGTACC | TCTGTTANAT | 3500 |
| TGAAACTTGT | CTCTACTGTC | TTTTTATTTC | AAACACAGCT | TATTAGGTGT | CTCTCAACCC | 3560 |
| ATCAAACNCA | CAATCTGAGT | CTTTAGGAGA | TTGCTTTGAA | TTTGTGCTAT | TGACTTATAT | 3620 |
| NTATATNAAA | TNTGTAAATG | TTTGGTAAAA | ATATCATCAT | GTACNTTTC | ATAATTACGC | 3680 |
| TATNTNCACA | TGATATATGT | CAGACTCTGG | AAATATGCAT | GCCACAGACA | CGTGTTTCTT | 3740 |
| GCCTAAAGGG | GCTGATGGAA | GACNCACATA | CNAATAGACG | ATTGCAGTAG | AATGAGAGTG | 3800 |
| GTGGTCTAAN | CAGTACATGT | CCTGATGTTG | CTCGGACAGT | TACTACNCCA | AGAGTACCCC | 3860 |
| CTGCATTGTC | AGGGTTAGCA | TCTCCTGGAA | GCCTCATGTA | AATGAAGAAT | TCATGCTCC | 3920 |
| ATCCAGGACC | TAATGAATAA | GAATCTGCAT | TTTAGCAAGA | CCCTCATATG | ATTCATATAC | 3980 |
| ACTTTTTTTT | TTTTTTTTA | GATGGAGTCT | CACTCTTGTC | GCCCAGGCTG | GAGTGCAATG | 4040 |
| GCATGATCTT | GGCTCACTGC | AACCTCTGCC | TCCCGGGTTC | AAGTGATTCT | CCTGTCTCAG | 4100 |
| CCTCCCTAGT | AGCTGGGACT | ACAGGTGCAT | GCCACAGTGG | CTGGCTAATT | TTTGTATTTT | 4160 |
| TAGTAGAGAC | AGGGTTTCAC | CATTTTGGTC | AGGCTGGTCT | TGAACTCATG | ACCTCCGGTG | 4220 |
| ATTCCCCGC | CTCGGCTTCC | CAAAGTGCTG | GGATTACAGA | CATGAGCCAC | CACACCCGCC | 4280 |
| TTATTCGTAT | ACNCATTTAA | TTCTGAGAAG | CACTCTATAG | AAAATAAGAA | TAAGAAAATA | 4340 |
| TTGGGCTCAC | AGGTGACATT | AATAAGTAAC | TTTATCGAGT | ACCCCAAATT | TTACCTATGT | 4400 |
| TTGGAAGATG | GGGTTAAAAG | GACACATTGA | AAACAAGAAC | TCATTGTGGC | TTTTTTTCC | 4460 |
| TCCTTTTTGA | ACAG TTT TCT ATT | TCT GGA ATG TTG | TCA ATT ATA TCT GAA | | | 4510 |
| | Phe Ser Ile Ser | Gly Met Leu | Ser Ile Ile Ser Glu | | | |
| | 110 | | 115 | | | |
| AGG AGA AAT GCA ACA TAT | CTG GTGAGTTGCC CGTTCTGTC TTTGTCCATC | | | | | 4561 |
| Arg Arg Asn Ala Thr Tyr | Leu | | | | | |
| 120 | 125 | | | | | |
| CTTGAAAAGA | TAAGAAGAAC | AGAGTTTAA | GAGTCTTAAG | GGAAACACAT | CTTTGTCTCC | 4621 |
| TATATTACTT | GTGAATGTGG | ATATATGATT | TTGTTTCAAT | CTATTTGTG | TCCTAAGGCT | 4681 |
| TTTTGCAACA | GAAGTTGGAT | ATATCATTAG | AAACATAAAT | TGTACCATTT | AACATACATG | 4741 |
| AAGTTTATGT | TTACCTTGAC | GTTCTTCTAA | AAAGTGTCCT | ACACCGGCAT | TGTCCTTGTA | 4801 |
| GGCATATTCA | CATGATCAAA | TAAATAATT | AGTTTCAAT | TAAGGAGAAT | ATTTGAGGAA | 4861 |
| AGACCGTACG | TGTTCATGTG | GTTCCTGAAG | GCAGTCCAGT | GAGAAAGTAA | TATATGCTTC | 4921 |
| ATTAAACAAT | GCGGACATTT | TCAGGGTTTC | CCTTTTTAAC | CAAAATTTGG | AAGCAATGTG | 4981 |
| GAATTTACTG | GATGCATCCA | GCCCTGAAAT | GAAGATAGGT | TTATTGAATG | TGCCAGCAAG | 5041 |
| TGCAGGCCCA | GGTCTGAGTG | TTCTTCATTA | TTATCAG GTG AGA GGA AGC CTG GGA | | | 5096 |

|  |  |
|---|---|
|                                                                                                Val Arg Gly Ser Leu Gly<br>                                                                                                          130 |  |
| GCA AAC ACT GCC AGC AGC ATA GCT GGG GGA ACG GGA ATT ACC ATC CTG<br>Ala Asn Thr Ala Ser Ser Ile Ala Gly Gly Thr Gly Ile Thr Ile Leu<br>     135                       140                     145 | 5144 |
| ATC ATC AAC CTG AAG AAG AGC TTG GCC TAT ATC CAC ATC CAC AGT TGC<br>Ile Ile Asn Leu Lys Lys Ser Leu Ala Tyr Ile His Ile His Ser Cys<br>     150                       155                     160 | 5192 |
| CAG AAA TTT TTT GAG ACC AAG TGC TTT ATG GCT TCC TTT TCC ACT<br>Gln Lys Phe Phe Glu Thr Lys Cys Phe Met Ala Ser Phe Ser Thr<br>165                     170                     175 | 5237 |
| GTATGTATTT TTTTTGTGT GGGAAGACTA AGATTCTGGG TCCTAATGTA AGTAAGAAGC | 5297 |
| CCTCTTCTCC TGTTCCATGA ACACCATCCT TTTCTGTAAC TTCTATTACA CAGTATAGTG | 5357 |
| GTTCTGTAAG TTCACACAGC CAGGGAGAT GCTGGCTGCC CACTCCCTC AACCCAGGCA | 5417 |
| AATTCCTCGG GGTTAAAGTT ATCTACTGCA AGTGACGATC TCTGGGTTTT TCTGTGCCTG | 5477 |
| TGTTTGTGTG TGTGTGTGTG TGTGTGTGTG TGTGTATGTG TCACTTTAAA AGGACTGGTC | 5537 |
| AGATGGTAGG GAGATGAAAA CAGGAGATGC TATAAGAAAA TAAACTTTTG GGGCGAATAC | 5597 |
| CAATGTGACT CTTTTTGTTT GTCATTTGTT GCTGTTCAAT AG GAA ATT GTA GTG<br>                                                           Glu Ile Val Val<br>                                                                    180 | 5651 |
| ATG ATG CTG TTT CTC ACC ATT CTG GGA CTT GGT AGT GCT GTG TCA CTC<br>Met Met Leu Phe Leu Thr Ile Leu Gly Leu Gly Ser Ala Val Ser Leu<br>     185                       190                     195 | 5699 |
| ACA ATC TGT GGA GCT GGG GAA GAA CTC AAA GGA AAC AAG GTAGATAGAA<br>Thr Ile Cys Gly Ala Gly Glu Glu Leu Lys Gly Asn Lys<br>200                   205                     210 | 5748 |
| GCCCGATATA AAATCTTGAA TGACAGGTTA ACGAATTGGA GCTTATTCC TTAAAATATG | 5808 |
| GCCTGGGTTT TCTGAAACAT TTCTTCCAGA AAATAGTTTC TCCAAGTTTT ATTACTTTGG | 5868 |
| TTTACAAATC TCACATTTAA ATCACATTTT ATACCATAAG TAGCACACAT TTCATAATAT | 5928 |
| TCCTCTGAAT GAGGGTTGGG ATAATAGGAC TGATATGTTA GAAATGCCTT AAAGTGTGTG | 5988 |
| GAGCATGAGA GATGGATGTA CAGAAGGCTT GTGAGGAAAC CACCCAGGTA TCTGGCCTTG | 6048 |
| TTTTCTGCCC CAGAACTAGC CGCCTATTCC TGTTTCTGTT TTATTCCTTT GTTTCTTGAC | 6108 |
| TTTTCCTTTC CAACTTGCTC TAAAACCTCA GTTTTCTTTC CTTTCTGATT CATGACTACC | 6168 |
| AAATGTTTTC ACTTGCCTCA CCCGTCCATT ACACCTTTGA TAAGAACCAC CAGACCTTGT | 6228 |
| GCTCATGTAC TTGCCCATGT CTGATGGAAG AAACATACTC TCTCCATCTG TCCACTTTCC | 6288 |
| TGAGGCATTC AAGTCTAGCC ACCTTTTAAA ATCACTCTCC TCCAGGCTGG GCACGGTGTC | 6348 |
| ACGCCTGTAA TCTCAGCACT TTGTGAGGCT GAGGAGGGCG GATCACTTGA AGTCAGGAGT | 6408 |
| TCAAAACCAG CCTGGCCAAA TGGCAAAACC AAATCTTCTT CAATTATAAC CAAATCTTAA | 6468 |
| ACCAAATCTC TACTAAAAAA TACAACAAAA CAAACAACA ACAACAAAAA CAGAAAAGGA | 6528 |
| AACATTAGCC CAGCGTGGTG GCAGGTACCT GAGGTTCCAG ATACTTGGGA GGCTGAAGCA | 6588 |
| GGAGAATCGC TTGAGCCCAA GAGATGGAGG TTGCAGTGAG CCGAGATCAT GCCACTGCAC | 6648 |
| CACAGCCAGG GTGACAGAGC CATACTTCCC AGCACATTGG GAGGCCAAAG CTGAAGAATA | 6708 |
| ATTTGAGGTG AGGATTTGGA GACCAGCCTG GCCAACATGG TGAAACTCCG TCTGTACTAA | 6768 |
| AAATATAAAA CTTAGTGGGG CATGGGGGCA CACACCTGTA ATTTCAGCTA CTTAGGAGGC | 6828 |
| TGAGGCAGGA GAATTGCTTG AACCCGGGAG GCGGAAGTTG CAGTGAGCCA AGATCGTGGC | 6888 |
| CACTGCACTC CAGCCTGGGT GACATAGTGA GATTCTGTCT CAAAAAAAAT AAAAGAAATT | 6948 |
| TAAAAAATCA CTCTCTTCCA AAGATAGATA AATAAGACAG CAGATATACT AAGGAATAAC | 7008 |

| | | | | | |
|---|---|---|---|---|---|
| CTCACCAACT | TGTCATTGAC | TGACATGATT | TCTTTTGGCC | CACTTGGCCA | GCTAGTCTGG | 7068 |
| TTTGGTTTTC | TGGAAATGAA | AGAAATAATC | AGAGTTTAAT | GACAGAGAGC | GTGAGACCCA | 7128 |
| GAAAGACAAA | AGTAGATGAG | GTAAGTCTCT | TGAGCGAGAC | TTCTAGGGAT | GGGAAATTTG | 7188 |

```
TGGTGATTGA TATGAAATGA TTTTTCCCTT ATCAG GTT CCA GAG GAT CGT GTT         7241
                                       Val Pro Glu Asp Arg Val
                                                       215

TAT GAA GAA TTA AAC ATA TAT TCA GCT ACT TAC AGT GAG TTG GAA GAC        7289
Tyr Glu Glu Leu Asn Ile Tyr Ser Ala Thr Tyr Ser Glu Leu Glu Asp
    220             225                 230

CCA GGG GAA ATG TCT CCT CCC ATT GAT TTA TAAGAATCAC GTGTCCAGAA          7339
Pro Gly Glu Met Ser Pro Pro Ile Asp Leu
235                 240
```

| | | | | | |
|---|---|---|---|---|---|
| CACTCTGATT | CACAGCCAAG | GATCCAGAAG | GCCAAGGTTT | TGTTAAGGGG | CTACTGGAAA | 7399 |
| AATTTCTATT | CTCTCCACAG | CCTGCTGGTT | TTACATTAGA | TTTATTCGCC | TGATAAGAAT | 7459 |
| ATTTTGTTTC | TGCTGCTTCT | GTCCACCTTA | ATATGCTCCT | TCTATTTGTA | GATATGATAG | 7519 |
| ACTCCTATTT | TTCTTGTTTT | ATATTATGAC | CACACACATC | TCTGCTGGAA | AGTCAACATG | 7579 |
| TAGTAAGCAA | GATTAACTG | TTTGATTATA | ACTGTGCAAA | TACAGAAAAA | AAGAAGGCTG | 7639 |
| GCTGAAAGTT | GAGTTAAACT | TTGACAGTTT | GATAATATTT | GGTTCTTAGG | GTTTTTTTTT | 7699 |
| TTTTAGCAT | TCTTAATAGT | TACAGTTGGG | CATGATTTGT | ACCATCCACC | CATACCCACA | 7759 |
| CAGTCACAGT | CACACACACA | TATGTATTAC | TTACACTATA | TATAACTTCC | TATGCAAATA | 7819 |
| TTTTACCACC | AGTCAATAAT | ACATTTTGC | CAAGACATGA | AGTTTATAA | AGATCTGTAT | 7879 |
| AATTGCCTGA | ATCACCAGCA | CATTCACTGA | CATGATATTA | TTTGCAGATT | GACAAGTAGG | 7939 |
| AAGTGGGGAA | CTTTTATTAA | GTTACTCGTT | GTCTGGGGAG | GTAAATAGGT | TAAAAACAGG | 7999 |
| GAAATTATAA | GTGCAGAGAT | TAACATTTCA | CAAATGTTTA | GTGAAACATT | TGTGAAAAAA | 8059 |
| GAAGACTAAA | TTAAGACCTG | AGCTGAAATA | AAGTGACGTG | GAAATGGAAA | TAATGGTTAT | 8119 |
| ATCTAAAACA | TGTAGAAAAA | GAGTAACTGG | TAGATTTTGT | TAACAAATTA | AGAATAAAG | 8179 |
| TTAGACAAGC | AACTGGTTGA | CTAATACATT | AAGCGTTTGA | GTCTAAGATG | AAAGGAGAAC | 8239 |
| ACTGGTTATG | TTGATAGAAT | GATAAAAAGG | GTCGGGCGCG | GAGGCTCACG | CCTGTAATCC | 8299 |
| CAGCCCTTTG | GGAGGCCGAG | GTGGGCAGAT | CACGAAGTCA | GTAGTTTGAG | ACCAGCCTGG | 8359 |
| CCAACATAGT | GAAACCCCGT | CTCTACTAAA | AATACAAAAA | AAAAATTAGC | TGGGTGTGGT | 8419 |
| GGCAGTCACC | TGTAGTCCCA | GCTACTTGGG | AGGATGAGGC | AGGAGAATCG | CTTGAACCTG | 8479 |
| GGAGGCGGAG | GTTGCAGTGA | GCCGAGATCG | CACCAGTGCA | CTCCAGCCTT | GGTGACAATG | 8539 |
| GGAGACTCCA | TCTCAAAAAA | AAAAAAAAA | AAAAAAAGAT | AAAAAGTCAG | AAATCTGAAA | 8599 |
| AGTGGAGGAA | GAGTACAAAT | AGACCTAAAT | TAAGTCTCAT | TTTTTGGCTT | TGATTTTGGG | 8659 |
| GAGACAAAGG | GAAATGCAGC | CATAGAGGGC | CTGATGACAT | CCAATACATG | AGTTCTGGTA | 8719 |
| AGATAAAAT | TTGATACACG | GTTTGGTGTC | ATTATAAGAG | AAATCATTAT | TAAATGAAGC | 8779 |
| AAGTTAACAC | TCTAAGAGAA | TTATTTTGAG | ATAGAAGTGA | AGCTAAGCTA | AACTTCACAT | 8839 |
| GCCTATAATT | GGAGGGAAAA | ACTAAGGATA | AAATCTAGCC | TAGAAGATAC | AATAATTAGT | 8899 |
| CATAAACATG | CATTGTGAAA | CTGTAGAGAG | CAGGTAGCCC | AAAATAGAGA | AAGATTAGAT | 8959 |
| AAAGAGAAAA | TAAGTATCCA | TCAGAGACAG | TATCTCTAGG | CTTGGGCAAG | AGAAAAGTCC | 9019 |
| ACAGTGATAA | GCAACTCCAC | CTAAGGCATG | AATATGCGGC | AGAGAAAACA | GCAATAGTGA | 9079 |
| ATGAATGCAA | AAGGTGCTGA | GCAAATTCCA | CACATGAGTA | TTGTGCATGA | GTAAATGAAT | 9139 |
| AAAACATTTG | CAAAGACCTT | TAGAGAAAGA | GAATGGGAGC | ATATGTGCGA | AATAAGATAG | 9199 |

```
TTGATTATGA ATAGAAGGTA GTGAAGAAAA GCAAGCTAAG AAAAAATTCT GTTTATAAAA      9259

GAAGGAAAAG ATAGTTTATG TTTTTAGCCT AAGTATAAGA GTCCTACAGA TGGACTGAAA      9319

AAAATCAGTC TGAGAGTATT AGTCACAATT AATGAAATAA TTACATTTTA TGTATTGAGG      9379

ATGCCAAGAT TAAAAGGTGA CAGGTAGATG TTAATTTCCC TAGATTGTGA AAGTGATCAC      9439

GACAATCACA CAACAAATAA TTAAGTGACT TGGTATGCTT TATTTAATTG TAGGGCCTGA      9499

GGTTTTCCAT TCTCATTTTT CTAAAATACA ATTTGTTTC TCCAAATTTG ACAGCAGAAT       9559

AAAACCCTA CCCTTTCACT GTGTATCATG CTAAGCTGCA TCTCTACTCT TGATCATCTG       9619

TAGGTATTAA TCACATCACT TCCATGGCAT GGATGTTCAC ATACAGACTC TTAACCCTGG      9679

TTTACCAGGA CCTCTAGGAG TGGATCCAAT CTATATCTTT ACAGTTGTAT AGTATATGAT     9739

ATCTCTTTTA TTTCACTCAA TTTATATTTT CATCATTGAC TACATATTTC TTATACACAA    9799

CACACAATTT ATGAATTTTT TCTCAAGATC ATTCTGAGAG TTGCCCCACC CTACCTGCCT    9859

TTTATAGTAC GCCCACCTCA GGCAGACACA GAGCACAATG CTGGGGTTCT CTTCACACTA    9919

TCACTGCCCC AAATTGTCTT TCTAAATTTC AACTTCAATG TCATCTTCTC CATGAAGACC    9979

ACTGAATGAA CACCTTTTCA TCCAGCCTTA ATTTCTTGCT CCATAACTAC TCTATCCCAC    10039

GATGCAGTAT TGTATCATTA ATTATTAGTG TGCTTGTGAC CTCCTTATGT ATTCTCAATT    10099

ACCTGTATTT GTGCAATAAA TTGGAATAAT GTAACTTGAT TTCTTATCTG TGTTTGTGTT    10159

GGCATGCAAG ATTTAGGTAC TTATCAAGAT AATGGGGAAT TAAGGCATCA ATAAAATGAT   10219

GCCAAAGACC AAGAGCAGTT TCTGAAGTCC TCCTTTTCAT CAGCTCTTTA TCAAACAGAA    10279

CACTCTATAA ACAACCCATA GCCAGAAAAC AGGATGTAGG AACAATCACC AGCACACTCT  10339

ATAAACAACC CATAGCCAGA AAACAGAATG TAAGGACAAT CACCAGCCAT CTTTTGTCAA   10399

TAATTGATGG AATAGAGTTG AAAGGAACTG GAGCATGAGT CATATTTGAC CAGTCAGTCC    10459

TCACTCTTAT TTACTTGCTA TGTAAACTTG AGAAAGCTTT TTTCTCTTTG TGAACCTCAG    10519

GTTTTACATC TGAAAATGAG AAATTTGGAA CAAAGATTC CTAACTGGTC TTTCTGTTCC     10579

CATATTCTGT GATTTTTCAA TATTTAGGAT TTTTGGTAAT CACAATTACT TAGTTTGTGG   10639

TTGAGATAGC AACACGAATC AGAACTATTT GGTGGACATA TTTTCAAGG AGTAGCTCTC    10699

CACTTTGGGT AAAGAAGTGA TGCNGGTCGT GGTGGCTCAC GCCTGTAATC CCAGCACTTT   10759

AGGGAGGCCA AGGCGGGTGG ATCACGAGGT CAGGAGATCG AGACCATCCT GGCTAACACG   10819

GTGAAACCCC GTCTCTACTA AAAATACAA AAAATTAGCC AGGCGTGGTG GCGGGCGCCT    10879

GTAGTCCCAC GTACTCGGGA GGCTGAGGCA GGAGAATGGC ATGAACCAGG GAGGCGGAGC   10939

TTGCCGTGAG CCGAGATAGC GCCACTGCAG TCCTCCTGG GCAAAAGAGC AAGACTGCGT    10999

CTCAAAAAAA AAAAAAAAA AAAAAAAGA AGTGTGTGGA GTAGCAGGAC ACCTGCAACA      11059

ATAATATTTT TCTAAATCCC TCTGAAAAAT GCTAATCAAA GGGTTTTTT CCTAAAAATT    11119

GTCTTAGAAA TAAAATTTCC CCTTTGGGAG ACCGAGGCTG GCAGATCACG AGGTCAGGAG   11179

ATAGAGACCA CGGTGAAACC CCGTCTCTAC TAAAAATACT AAAAATTAGC CGGGGNGTGG   11239

TGGTGGGTAC ACCTGTAGTC CCAGCTACTT GGAGGCTGAG GCTGGAGAAT CACGTGAAC    11298
```

( 2 ) INFORMATION FOR SEQ ID NO:3:

( i ) SEQUENCE CHARACTERISTICS:
        ( A ) LENGTH: 244 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Met | Asp | Thr | Glu | Ser | Asn | Arg | Arg | Ala | Asn | Leu | Ala | Leu | Pro | Gln | Glu |
| --- | --- | --- | --- | --- | --- | --- | --- | --- | --- | --- | --- | --- | --- | --- | --- |
| 1 | | | | 5 | | | | | 10 | | | | | 15 | |
| Pro | Ser | Ser | Val | Pro | Ala | Phe | Glu | Val | Leu | Glu | Ile | Ser | Pro | Gln | Glu |
| | | | 20 | | | | | 25 | | | | | 30 | | |
| Val | Ser | Ser | Gly | Arg | Leu | Leu | Lys | Ser | Ala | Ser | Ser | Pro | Pro | Leu | His |
| | | 35 | | | | | 40 | | | | | 45 | | | |
| Thr | Trp | Leu | Thr | Val | Leu | Lys | Lys | Glu | Gln | Glu | Phe | Leu | Gly | Val | Thr |
| | 50 | | | | | 55 | | | | | 60 | | | | |
| Gln | Ile | Leu | Thr | Ala | Met | Ile | Cys | Leu | Cys | Phe | Gly | Thr | Val | Val | Cys |
| 65 | | | | | 70 | | | | | 75 | | | | | 80 |
| Ser | Val | Leu | Asp | Ile | Ser | His | Ile | Glu | Gly | Asp | Ile | Phe | Ser | Ser | Phe |
| | | | | 85 | | | | | 90 | | | | | 95 | |
| Lys | Ala | Gly | Tyr | Pro | Phe | Trp | Gly | Ala | Ile | Phe | Phe | Ser | Ile | Ser | Gly |
| | | | 100 | | | | | 105 | | | | | 110 | | |
| Met | Leu | Ser | Ile | Ile | Ser | Glu | Arg | Arg | Asn | Ala | Thr | Tyr | Leu | Val | Arg |
| | | 115 | | | | | 120 | | | | | 125 | | | |
| Gly | Ser | Leu | Gly | Ala | Asn | Thr | Ala | Ser | Ser | Ile | Ala | Gly | Gly | Thr | Gly |
| | 130 | | | | | 135 | | | | | 140 | | | | |
| Ile | Thr | Ile | Leu | Ile | Ile | Asn | Leu | Lys | Lys | Ser | Leu | Ala | Tyr | Ile | His |
| 145 | | | | | 150 | | | | | 155 | | | | | 160 |
| Ile | His | Ser | Cys | Gln | Lys | Phe | Phe | Glu | Thr | Lys | Cys | Phe | Met | Ala | Ser |
| | | | | 165 | | | | | 170 | | | | | 175 | |
| Phe | Ser | Thr | Glu | Ile | Val | Val | Met | Met | Leu | Phe | Leu | Thr | Ile | Leu | Gly |
| | | | | 180 | | | | | 185 | | | | | 190 | |
| Leu | Gly | Ser | Ala | Val | Ser | Leu | Thr | Ile | Cys | Gly | Ala | Gly | Glu | Glu | Leu |
| | | | 195 | | | | | 200 | | | | | 205 | | |
| Lys | Gly | Asn | Lys | Val | Pro | Glu | Asp | Arg | Val | Tyr | Glu | Glu | Leu | Asn | Ile |
| | 210 | | | | | 215 | | | | | 220 | | | | |
| Tyr | Ser | Ala | Thr | Tyr | Ser | Glu | Leu | Glu | Asp | Pro | Gly | Glu | Met | Ser | Pro |
| 225 | | | | | 230 | | | | | 235 | | | | | 240 |
| Pro | Ile | Asp | Leu | | | | | | | | | | | | |

( 2 ) INFORMATION FOR SEQ ID NO:4:

( i ) SEQUENCE CHARACTERISTICS:
        ( A ) LENGTH: 243 amino acids
        ( B ) TYPE: amino acid
        ( C ) STRANDEDNESS:
        ( D ) TOPOLOGY: linear ( x i ) SEQUENCE DESCRIPTION: SEQ ID NO:4:

| Met | Asp | Thr | Glu | Asn | Lys | Ser | Arg | Ala | Asp | Leu | Ala | Leu | Pro | Asn | Pro |
| --- | --- | --- | --- | --- | --- | --- | --- | --- | --- | --- | --- | --- | --- | --- | --- |
| 1 | | | | 5 | | | | | 10 | | | | | 15 | |
| Gln | Glu | Ser | Pro | Ser | Ala | Pro | Asp | Ile | Glu | Leu | Leu | Glu | Ala | Ser | Pro |
| | | | 20 | | | | | 25 | | | | | 30 | | |
| Pro | Ala | Lys | Ala | Leu | Pro | Glu | Lys | Pro | Ala | Ser | Pro | Pro | Pro | Gln | Gln |
| | | | 35 | | | | | 40 | | | | | 45 | | |
| Thr | Trp | Gln | Ser | Phe | Leu | Lys | Lys | Glu | Leu | Glu | Phe | Leu | Gly | Val | Thr |
| | 50 | | | | | 55 | | | | | 60 | | | | |
| Gln | Val | Leu | Val | Gly | Leu | Ile | Cys | Leu | Cys | Phe | Gly | Thr | Val | Val | Cys |
| 65 | | | | | 70 | | | | | 75 | | | | | 80 |
| Ser | Thr | Leu | Gln | Thr | Ser | Asp | Phe | Asp | Asp | Glu | Val | Leu | Leu | Leu | Tyr |
| | | | | 85 | | | | | 90 | | | | | 95 | |
| Arg | Ala | Gly | Tyr | Pro | Phe | Trp | Gly | Ala | Val | Leu | Phe | Val | Leu | Ser | Gly |

```
                        100                        105                         110
   Phe  Leu  Ser  Ile  Met  Ser  Glu  Arg  Lys  Asn  Thr  Leu  Tyr  Leu  Val  Arg
             115                      120                      125

Gly  Ser  Leu  Gly  Ala  Asn  Ile  Val  Ser  Ser  Ile  Ala  Ala  Gly  Leu  Gly
        130                      135                      140

Ile  Ala  Ile  Leu  Ile  Leu  Asn  Leu  Ser  Asn  Asn  Ser  Ala  Tyr  Met  Asn
   145                      150                      155                      160

Tyr  Cys  Lys  Asp  Ile  Thr  Glu  Asp  Asp  Gly  Cys  Phe  Val  Thr  Ser  Phe
                       165                      170                      175

Ile  Thr  Glu  Leu  Val  Leu  Met  Leu  Leu  Phe  Leu  Thr  Ile  Leu  Ala  Phe
                  180                      185                      190

Cys  Ser  Ala  Val  Leu  Leu  Ile  Ile  Tyr  Arg  Ile  Gly  Gln  Glu  Phe  Glu
             195                      200                      205

Arg  Ser  Lys  Val  Pro  Asp  Asp  Arg  Leu  Tyr  Glu  Glu  Leu  His  Val  Tyr
        210                      215                      220

Ser  Pro  Ile  Tyr  Ser  Ala  Leu  Glu  Asp  Thr  Arg  Glu  Ala  Ser  Ala  Pro
   225                      230                      235                      240

Val  Val  Ser
```

(2) INFORMATION FOR SEQ ID NO:5:

(i) SEQUENCE CHARACTERISTICS:
        (A) LENGTH: 235 amino acids
        (B) TYPE: amino acid
        (C) STRANDEDNESS:
        (D) TOPOLOGY: linear (xi) SEQUENCE DESCRIPTION: SEQ ID NO:5:

```
   Met  Asp  Thr  Glu  Asn  Arg  Ser  Arg  Ala  Asp  Leu  Ala  Leu  Pro  Asn  Pro
   1                   5                        10                       15

Gln  Glu  Ser  Ser  Ser  Ala  Pro  Asp  Ile  Glu  Leu  Leu  Glu  Ala  Ser  Pro
                  20                       25                       30

Ala  Lys  Ala  Ala  Pro  Pro  Lys  Gln  Thr  Trp  Arg  Thr  Phe  Leu  Lys  Lys
             35                       40                       45

Glu  Leu  Glu  Phe  Leu  Gly  Ala  Thr  Gln  Ile  Leu  Val  Gly  Leu  Ile  Cys
        50                       55                       60

Leu  Cys  Phe  Gly  Thr  Ile  Val  Cys  Ser  Val  Leu  Tyr  Val  Ser  Asp  Phe
   65                       70                       75                       80

Asp  Glu  Glu  Val  Leu  Leu  Leu  Tyr  Lys  Leu  Gly  Tyr  Pro  Phe  Trp  Gly
                       85                       90                       95

Ala  Val  Leu  Phe  Val  Leu  Ser  Gly  Phe  Leu  Ser  Ile  Ile  Ser  Glu  Arg
                  100                      105                      110

Lys  Asn  Thr  Leu  Tyr  Leu  Val  Arg  Gly  Ser  Leu  Gly  Ala  Asn  Ile  Val
             115                      120                      125

Ser  Ser  Ile  Ala  Ala  Gly  Thr  Gly  Ile  Ala  Met  Leu  Ile  Leu  Asn  Leu
        130                      135                      140

Thr  Asn  Asn  Phe  Ala  Tyr  Met  Asn  Asn  Cys  Lys  Asn  Val  Thr  Glu  Asp
   145                      150                      155                      160

Asp  Gly  Cys  Phe  Val  Ala  Ser  Phe  Thr  Thr  Glu  Leu  Val  Leu  Met  Met
                       165                      170                      175

Leu  Phe  Leu  Thr  Ile  Leu  Ala  Phe  Cys  Ser  Ala  Val  Leu  Phe  Thr  Ile
                  180                      185                      190

Tyr  Arg  Ile  Gly  Gln  Glu  Leu  Glu  Ser  Lys  Lys  Val  Pro  Asp  Asp  Arg
             195                      200                      205

Leu  Tyr  Glu  Glu  Leu  Asn  Val  Tyr  Ser  Pro  Ile  Tyr  Ser  Glu  Leu  Glu
        210                      215                      220
```

```
Asp  Lys  Gly  Glu  Thr  Ser  Ser  Pro  Val  Asp  Ser
225                 230                           235
```